(12) United States Patent
Adachi

(10) Patent No.: US 6,458,404 B1
(45) Date of Patent: *Oct. 1, 2002

(54) DEHYDRATED GEL COMPOSITION FROM HYDRATED ISOLATED ACETYLATED GELLAN GUM

(75) Inventor: Norifumi Adachi, Toyonaka (JP)

(73) Assignee: San-Ei Gen F.F.I., Inc., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/242,806

(22) PCT Filed: Aug. 22, 1997

(86) PCT No.: PCT/JP97/02929
§ 371 (c)(1),
(2), (4) Date: May 19, 1999

(87) PCT Pub. No.: WO98/08399
PCT Pub. Date: Mar. 5, 1998

(30) Foreign Application Priority Data

| Aug. 27, 1996 | (JP) | 8-225614 |
| Sep. 13, 1996 | (JP) | 8-243471 |
| Oct. 18, 1996 | (JP) | 8-276216 |
| Oct. 29, 1996 | (JP) | 8-287138 |
| Nov. 22, 1996 | (JP) | 8-312466 |
| Nov. 25, 1996 | (JP) | 8-313680 |
| Dec. 2, 1996 | (JP) | 8-321703 |
| Dec. 6, 1996 | (JP) | 8-326506 |
| Dec. 11, 1996 | (JP) | 8-330644 |
| Dec. 27, 1996 | (JP) | 8-349412 |
| Dec. 27, 1996 | (JP) | 8-349414 |
| Dec. 27, 1996 | (JP) | 8-349417 |
| Dec. 27, 1996 | (JP) | 8-349431 |
| Dec. 27, 1996 | (JP) | 8-351161 |
| Feb. 4, 1997 | (JP) | 9-021294 |
| Feb. 17, 1997 | (JP) | 9-032371 |
| Mar. 6, 1997 | (JP) | 9-051649 |
| Mar. 7, 1997 | (JP) | 9-053601 |

(51) Int. Cl.[7] .................................. A23C 1/054
(52) U.S. Cl. ........................... 426/573; 426/473
(58) Field of Search .......................... 426/473, 573

(56) References Cited

U.S. PATENT DOCUMENTS

| 4,326,052 A |   | 4/1982 | Kang et al. |
| 4,326,053 A | * | 4/1982 | Kang et al. ............... 536/1 |
| 4,503,084 A | * | 3/1985 | Baird et al. |
| 4,746,528 A | * | 5/1988 | Prest et al. |
| 4,869,916 A | * | 9/1989 | Clark et al. |

(List continued on next page.)

FOREIGN PATENT DOCUMENTS

| JP | 62-115253 | 5/1987 |
| JP | 62-130671 | 6/1987 |
| JP | 62-244354 | 10/1987 |

(List continued on next page.)

OTHER PUBLICATIONS

Morita, Yasuyuki et al., "About the characteristics of native gellan gum and its application to food (in Japanese)" *Gekkan Food Chemical* (Mar. 1997), 13:3, pp. 110–114.

*Primary Examiner*—Nina Bhat

(57) ABSTRACT

The invention provides a native gellan gum-containing composition, and particularly based on the multifunctionality thereof, provides freeze/thaw-resistant gel compositions and dehydrated gels and jellies available therefrom, rice cake-like gels and rice cake substitutes, copy foods, cold retention compositions and cooling agents. The invention further provides the use of the above composition as additives for the expression of unique functions, for example a dispersion stabilizer, an additive for thickened compositions, a heat resistance-imparting agent, a syneresis inhibitor, a foam stabilizer, and a food palatability/body-improving agent.

8 Claims, 47 Drawing Sheets

U.S. PATENT DOCUMENTS

| | | | |
|---|---|---|---|
| 5,143,646 A | * | 9/1992 | Nochumson et al. |
| 5,277,915 A | * | 1/1994 | Provonchee et al. |
| 5,360,828 A | * | 11/1994 | Morrison |
| 5,387,423 A | * | 2/1995 | Emoto et al. |
| 5,549,921 A | * | 8/1996 | Robinson et al. |
| 5,718,931 A | * | 2/1998 | Walter et al. |
| 6,242,035 B1 | * | 6/2001 | Clark et al. ............ 426/573 |

FOREIGN PATENT DOCUMENTS

| | | |
|---|---|---|
| JP | 63-169950 | 7/1988 |
| JP | 63-169951 | 7/1988 |
| JP | 63-240796 | 10/1988 |
| JP | 63-248347 | 10/1988 |
| JP | 64-37258 | 2/1989 |
| JP | 64-40591 | 2/1989 |
| JP | 1-257434 | 10/1989 |
| JP | 2-16941 | 1/1990 |
| JP | 3-39058 | 2/1991 |
| JP | 3-272651 | 12/1991 |
| JP | 4-228042 | 8/1992 |
| JP | 4-228060 | 8/1992 |
| JP | 5-236892 | 9/1993 |

* cited by examiner

Synergistic Effect of
Tamarind seed gum + Native gellan gum
(pH 3.5)

Synergistic Effect of Glucomannan + Native gellan gum

Synergistic Effect of
Locust bean gum + Native gellan gum
(pH 3.5)

Synergistic Effect of
Pullulan + Native gellan gum
(pH 3.5)

Synergistic Effect of Tragacanth gum + Native gellan gum (pH 3.5)

Synergistic Effect of Microcrystalline cellulose + Native gellan gum (ph3.5)

Synergistic Effect of
SSHC + Native gellan gum
(pH 3.5)

Synergistic Effect of
Psyllium seed gum + Native gellan gum

Synergistic Effect of
Lamda-carrageenan + Native gellan gum
(pH 3.5)

Synergistic Effect of CMC + Native gellan gum

\* Curve of A or B shows A or B composition is gelating, not thickening

DEHYDRATED GEL COMPOSITION FROM HYDRATED ISOLATED ACETYLATED GELLAN GUM

FIELD OF THE INVENTION

The present invention relates to various new uses of native gellan gum which are based on its inherent characteristics.

BACKGROUND OF THE INVENTION

Being a macromolecular polysaccharide elaborated by microorganisms in culture, gellan gum is a current focus of interest and much research has already been undertaken into its physical properties, gel characteristics and potential applications (Food Chemical, Supplement to December 1986 issue, pp. 61–68; New Food Industry, 1996, Vol., 38, 11, pp. 21–31; Unexamined Japanese Patent Publication No.88051/1984). Gellan gum is derived from the mucilagenous secretions of *Pseudomonas elodea* (ATCC31461) and includes the deacetyl-gum which is obtainable by heating said mucilagenous secretions under weakly alkaline conditions for deacetylation and the pure deacetyl-gum which is available on further purification of said deacetyl-gum (Food Chemical 1986, Supplement to December 1986 issue, pp. 61–62).

The gels formed from this gellan gum are not only satisfactory in heat resistance, acid resistance and enzyme resistance but well amenable to the modification of gel strength by controlling the cation concentration to thereby provide various textures. For those reasons, gellan gum has been regarded as an important food material, particularly in food industry and culinary practice, and has been used in Japan since 1988 and in the United States of America since 1990.

On the other hand, native gellan gum which is a distinct grade of gellan gum, i.e. the crude acetyl-gum just elaborated by microorganisms, has attracted little attention and studies on this native product are trailing behind.

DISCLOSURE OF INVENTION

The inventors of the present invention scrutinized this native gellan gum, which is said distinct grade of gellan gum, and energetically exploring into its physical properties, gel characteristics, etc. for some time, found that native gellan gum is fundamentally different from the hitherto-known gelling agents and said gellan gum. The inventors further confirmed that multifunctional gel compositions can be formulated with it and the production processes for end products can be simplified by exploiting those unique characteristics of native gellan gum and that native gellan gum is useful as an additive by which new functions which could not be implemented in the past can be imparted to food and other end products. The present invention has been developed on the basis of the above findings.

The present invention, therefore, is directed to multifunctional compositions comprising native gellan gum (hereinafter referred to simply as functional compositions).

More particularly, the present invention is directed to said functional compositions which are gel compositions having the following various unique characteristics and to uses for the compositions.

(1) A freeze-thaw resistant gel composition
(2) Dehydrated gels and jellies prepared therefrom
(3) Rice cake-like gels and substitute foods for rice cakes
(4) Copy foods
(5) Cold retention compositions and cold-retaining agents The present invention is further directed to said functional compositions for use as an additive which expresses the following unique functions based-on the inherent characteristics of native gellan gum and to uses of said additives.

(6) A dispersion stabilizer
(7) A thickened composition additive
(8) A heat resistance-imparting agent:
(9) A syneresis inhibitor
(10) A foam stabilizer
(11) A food palatability and body-improving agent

BEST MODES OF CARRYING OUT THE INVENTION

Figure 1:
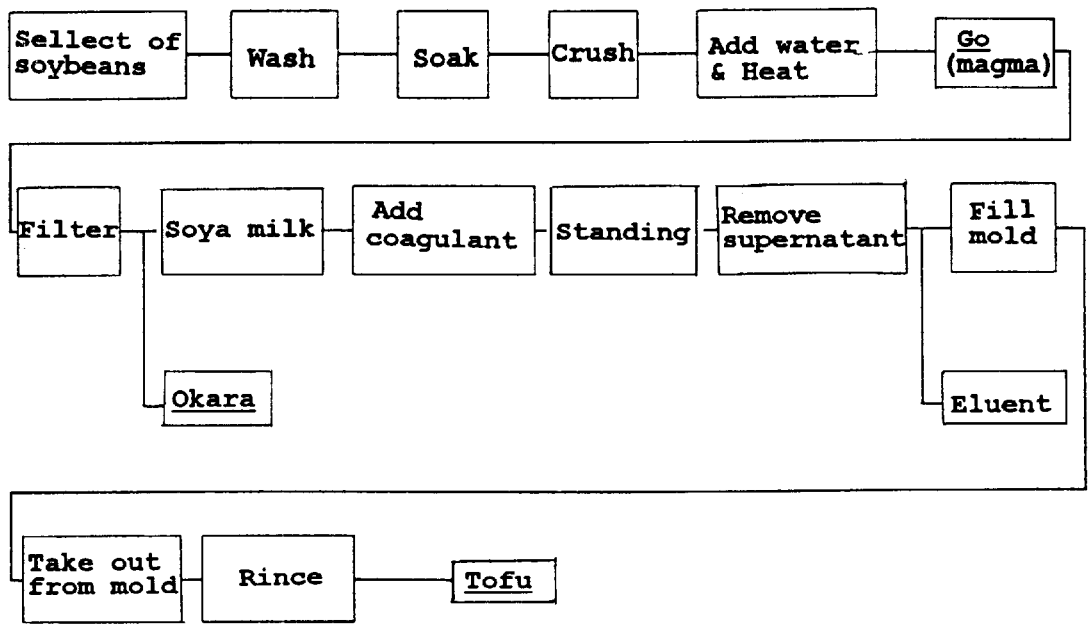
FIG. 1 is a diagram showing a general process for the production of momen tofu (coarse-texture soybean curd).

Native gellan gum for use in the present invention is a macromolecular polysaccharide of the microbial origin (melting point and solidification point: 65~70° C.) which is available as the pre-deacylation precursor of gellan gum, a polysaccharide (molecular weight: ca. 6~7×10$^5$) composed of glucose, glucronic acid and rhamnose in a molar ratio of 2:1:1 (Unexamined Japanese Patent Publication No.79397/1980).

This native gellan gum is generally produced by culture of microorganisms.

Specifically, a typical production technology comprises inoculating and growing *Pseudomonas elodea* ATCC31461 or an equivalent strain in a liquid medium containing 3% of glucose, 0.05% of $KH_4NO_3$, 0.01% of $MgSO_4.7H_2O$, 0.09% of $NH_4NO_3$, and a minor proportion of organic nitrogenous matter at about 30° C. under aerobic conditions for about 50 hours and isolating and recovering a mucilaginous substance produced on the cell surface from the resulting culture broth without deacylation (Unexamined Japanese Patent Publication No.79397/1980).

Since native gellan gum is of the natural origin, its structure may vary subtly according to the producer strain used and purification conditions. In this sense, the native gellan gum for use in the present invention is not categorically defined by any chemical formula (Sanderson, G. R., Food Gels, ed. Peter Harris, Elsevier Science Publishers Ltd., England, 1990, p. 204) but may be any substance having the properties of the native gellan gum produced by the above-mentioned technology using said stain of microorganism (ATCC31461).

The present invention comprising the various embodiments described in detail below has its footing on the discovery that such gellan gum either by itself or in the presence of other substances expresses specific and distinct properties.

The various embodiments of the invention are now described with reference to such properties.

(1) Freeze-thaw Resistant Gel Composition

The invention relevant to this embodiment was developed on the basis of the new finding that a gel composition prepared using native gellan gum has unique properties compared with gel compositions prepared using the conventional gelling agents, e.g. that it will retain its elasticity and dimensional stability even if it is frozen and then thawed, that substantially no separation of water is observed after thawing, that it has good palatability even when frozen, and that it regains the mouth-feel of the original gel composition upon thawing.

The gel composition according to the invention is not particularly restricted in regard to the formulating amount of native gellan gum as far as it contains native gellan gum and may optionally contain other and conventional gelling agents. Generally, the gel composition of the invention contains native gellan gum in a proportion of 0.1~3 weight %, preferably 0.15~2 weight %, based on 100 weight % of the whole gel composition.

There is no particular limitation on the method for production of the gel composition of the invention. A typical method may comprise putting the whole amount of native gellan gum in water, causing it to dissolve under agitation at 80° C. for 10 minutes, and cooling the solution to provide a gel composition.

The gel composition of this invention does not undergo any significant change in water content upon freezing and thawing. Therefore, the concentration of components (e.g. sugar concentration) contained therein is not altered, so that oversaturation and precipitation of such components seldom take place upon freeze-thaw.

The gel composition prepared using native gellan gum is safe to the human being and presents with a jelly-like texture or palatability. Therefore, in this invention, the above properties can be exploited in the production of various freeze-thaw-resistant jelly foods which may comprise adding sugars, fruit juices, milk ingredients, wine, cacao ingredients, and/or other flavoring matter so as to impart the desired sweetness, flavor and aroma or optionally formulating fruit pulps, boiled adzuki beans, etc.

The jelly thus produced has a good crisp mouth-feel in frozen condition and, therefore, if suited to one's taste, can be eaten as it is. Moreover, since the jelly retains its quality over a long time of freezer storage and, upon thawing, shows little change from the pre-freezing condition in gel strength, appearance, mouth-feel, and water-holding properties, it can be preserved in frozen state or distributed for marketing either in frozen condition or after thawing.

There is no particular limitation on the methods for freezing and thawing. Thus, for example, the freezing method which comprises freezing the gel composition (jelly) in a freezer at −18° C. and the method of allowing it to thaw spontaneously in the atmosphere at room temperature or thawing it rapidly in an electronic range can be employed.

(2) Dehydrated Gels and Jellies Prepared from the Gels

The invention relevant to this embodiment was developed on the basis of the finding that a hydrogel prepared using native gellan gum can be compacted by drying to allow long-term storage regardless of storage conditions and that this dehydrated gel can be easily reconstituted with water to reproduce the original elasticity and form.

The dehydrated gel according to this invention is prepared from a hydrogel obtained using native gellan gum.

There is no particular limitation on the method of preparing said hydrogel. A typical method may comprise dispersing generally 0.1~3 weight %, preferably 0.15~2 weight %, based on 100 weight % of the hydrogel to be provided, of native gellan gum in an aqueous medium, heating the dispersion for dissolving at about 80° C. for about 10 minutes, and cooling the solution.

The hydrogel may contain, in addition to native gellan gum and water, any other ingredient that does not separate out upon dehydration and redissolves readily in aqueous medium, virtually without restriction. Taking a hydrogel for food use as an example, said other ingredient includes sugars, high-performance sweeteners, fruit pulps, boiled adzuki beans, oily flavors, etc. which are intended to impart the desired sweetness, flavor and aroma.

Then, the hydrogel thus obtained can be dried to provide the dehydrated gel of the invention. The method for dehydration is not particularly restricted but includes drying in a hot air current and freeze-drying.

Preferably, the dehydrated gel of the invention is substantially free of moisture from the standpoint of shelf-life, convenience in transportation, etc. but this is not absolutely necessary. Thus, it may contain water in an amount of, for example, about 10~20% weight based on the water content of the original hydrogel.

When water is added to this dehydrogel and the mixture allowed to stand, the dehydrogel readily absorbs a large amount of water and swells to express physical properties (elasticity and stiffness) not much different from the properties of the original hydrogel prior to drying.

Therefore, this invention is further directed to the hydrogel available upon reimmersion of said dehydrated gel in water.

The hydrogel prepared using native gellan gum is safe to human health and has a jelly-like texture so that it is of use as a food gel, particularly for the production of jelly foods.

The present invention, thus, further includes edible dry jellies which can be obtained by dehydrating jellies prepared using native gellan gum and, further, jelly foods which can be conveniently prepared by allowing the dehydrated jellies to absorb water.

There is no particular limitation on the method for water reconstitution of such a dehydrated gel or jelly but it is sufficient that the gel or jelly be simply placed in water and allowed to stand as it is. In the preparation of jellies, the water for reconstitution may contain an alcohol, sweetener, acidulant, flavor, etc.

The jellies thus obtained retain the pre-drying properties, such as elasticity and firmness, and as satisfactory a texture as that of the pre-drying jellies, being little influenced by the dehydration procedure.

Thus, in accordance with the invention, there is provided a jelly which can be reduced in weight and size by dehydration and, hence, has an extended shelf-life and which, in addition, can be easily reconstituted for expression of the original palatability suited for ingestion.

(3) Rice Cake-like Gels

The invention relevant to this embodiment was developed on the basis of the finding that when native gellan gum and glutinous rice are used in combination, not only heat resistance can be imparted to native gellan gum which, by itself, is not heat-resistant but a viscoelastic gel simulating a rice cake can be produced.

Substitutes for rice cakes, which exploit gelling agents, have heretofore been proposed [Unexamined Japanese Patent Publication No.169954/1988, "Method for Producing Rice Cakes"; Unexamined Japanese Patent Publication No.60346/1989, "Method of Imparting Heat Resistance to Starch and Chemically Modified Starch", Unexamined Japanese Patent Publication No.236892/1993, "Rice Cake or Dumpling", and Unexamined Japanese Patent Publication No.261702/1994, "Konjak-Rice Cake"]. However, gelling agents such as carrageenan, xanthan gum and gelatin are generally lacking in heat resistance and presents the problem that substitutes for rice cakes obtained from them are dissolved or significantly macerated at temperatures not over 70° C. This invention solves this problem.

The invention is further based on the novel finding that native gellan gum significantly inhibits the aging, particularly hardening with time, of the starch component of glutinous rice.

The glutinous rice which can be used in this invention is not particularly restricted in form and other features only provided that it is glutinous rice as such or a preparation derived from glutinous rice but it is convenient to use milled glutinous rice for the preparation of rice cakes and shiratama (rice-flour dumplings). The milled glutinous rice includes a variety of flours such as shiratama-ko (alias kanzarashi-ko), mochi-ko (alias, gyuhi-ko), domyoji-ko, shinbiki-ko (alias naka-mizin), Jonan-ko (alias goku-mizin), koiro (alias kogashi mizin), mizin-ko (alias rakugan-ko), iri-mizin-ko, and kanbai-ko.

The gel of the invention and the composition for the preparation of the gel (both are collectively referred to hereinafter as gel composition) may be supplemented with other ingredients in addition to native gellan gum and glutinous rice. For example, nonglutinous rice and/or a preparation derived therefrom, which can be added to glutinous rice, can be incorporated. Furthermore, suitable starches and saccharides, coloring matter, flavors, emulsifiers, enzymes, oil and fat, preservatives, proteins, seasonings, gelling agents, thickeners, etc. can also be added.

The ratio of native gellan gum to glutinous rice in the gel composition of the invention is not particularly restricted but is generally 1:3–1:25 (dry solid weight ratio), preferably 1:5–1:13 (dry solid weight ratio), more preferably 1:7–1:10 (dry solid weight ratio). Generally when the formulating ratio of native gellan gum to glutinous rice in the gel or composition is larger than 1:3 (nateive gellan gum:glutinous, dry solid weight ratio), the heat resistance of the composition is so low that dissolution or maceration tends to take place when the composition is heated in water, for example in retort treatment, or in a hydrous environment. On the other hand, when the formulating ratio of native gellan gum to glutinous rice is lower than 1:25 (native gellan gum:glutinous rice, dry solid weight ratio), the rice cake-like viscoelasticity of the produce tends to be short-lived.

The gel composition of the invention is produced by heating native gellan gum and glutinous rice in the presence of water. The amount of water need only be within the range permitting co-molding of native gellan gum and glutinous rice and can be judiciously selected by one skilled in the art.

Taking the production of shiratama in accordance with this invention as an example, shiratama-ko (shiratama flour) and native gellan gum are blended in a ratio of 1:3 through 1:25 (dry solid weight ratio) and a suitable amount of water is added to the blend until an adequate consistency providing for an integral mass has been obtained. This mass is molded into balls with a diameter of about 2 cm or filled into molds. Then, such moldings can be directly heated or be put in water, shiruko (adzuki-bean meal soup) or zenzai (thick adzuki-bean soup) and heated. The heating means is not critical. The rice cake-like gel of the invention is stable even against rugged heating conditions such as retort treatment, not easily dissolving out or getting macerated.

Thus, this invention is particularly useful for the production of those foods which are required to show a lasting rice cake-like viscoelasticity and a sufficient heat resistance to withstand the heat treatment in water or in a hydrous environment. As an example of such food, a canned drink comprising an adzuki-bean soup containing shiratama balls can be mentioned.

Furthermore, this invention provides a low-calorie food, as a substitute for rice cakes, which is not degraded by aging and, when cooked into zoni (a soup containing rice balls), for instance, will not dissolve out or become sticky.

(4) Copy Food

The invention relevant to this embodiment was developed on the basis of the finding that a variety of mouth-feels can be expressed with native gellan gum by controlling its formulating amount.

The term "copy food" in the context of the invention means any food product available on substitution of a food material for another material and broadly encompasses foods not only for human consumption but also foods given to fish and animals such as dogs and cats. As specific examples, there may be mentioned Japanese style cakes manufactured by using starch as a part or the whole of the formulation, such as sakuramochi (cherry leaf-wrapped rice cakes) and kuzukiri (arrowroot noodles), simulated fishery products, teeth-hardening foods for infants and preschool children, pet foods with suitable biting resistance for dogs, and artificial baits for use in fishing.

The copy food mentioned above may be any food which comprises a native gellan gum-containing hydrogel composition of the invention and may be either solely or partially comprised of said hydrogel composition.

The hydrogel composition is a gelatinous composition prepared by dissolving native gellan gum in an aqueous medium which may contain seasonings, colors, flavors, etc. which are necessary for expression of desired food characteristics.

Generally foods containing less than 0.5 weight % of native gellan gum give gelatin-like mouth-feels, while those containing about 0.5~1 weight % of the gum are rice cake-like. At higher levels of addition, a conjak-like or boiled fish paste-like feel and even a jellyfish-like feel are expressed.

Taking a sakuramochi-style dessert food, among Japanese style cakes, as an example, the native gellan gum content is selected from the range of 0.3~2 weight % based on 100 weight % of the total food. In the case of kuzukiri desserts, the proportion is selected from the range of 0.5~1 weight % on the same basis.

Taking a copy squid simulating the mouth-feel of a squids among simulated fishery produces, the proportion of native gellan gum relative to 100 weight % of the whole food is selected from the range of 1~4 weight %. The same applies to artificial baits.

Taking a copy abalone having abalone-like mouth-feel, among simulated fishery produces, as an example, the formulating amount of native gellan gum relative to 100 weight % (total weight) of aqueous fraction is selected from the range of 14~20 weight %.

The term "abalone-like mouth-feel" in the context of the invention means a mouth-feel closely resembling that of a raw abalone, that is to say an elastic but firm and crisp mouth-feel. This abalone-like mouth-feel is the organoleptic quality which has never been simulated with the conventional polysaccharide, and this mouth-feel can be implemented only by controlling the formulating amount of native gellan gum to 14~20 weight % relative to water as mentioned above and heating the mixture in the presence of water.

In order that the gel having such an abalone-like mouth-feel may be provided in a form resembling an abalone morphologically as well, native gellan gum may be heated in the presence of water in a metal mold or the like or the gel prepared may be sculptured. When the gel having such an abalone-like mouth-feel is to be used as a food ingredient, the gel can be prepared or processed into a form suited for the intended food product. For example, when the gel having an abalone-like mouth-feel is to be used in sea-food sandwiches, the gel can be molded into a sheet. This is also an aspect of the invention which is superior to the use of a real abalone.

While the specific procedure for the production of each kind of copy food is detailed in the examples presented hereinafter, it should be understood that these are merely illustrative and the technology of the invention for the production of copy foods is not limited to the examples.

Native gellan gum is a diet fiber and, as such, has substantially no calorific value. Therefore, the copy food of the invention is particularly useful as a food material which enables persons under the restriction of calorie intake to enjoy a variegated dietary life equivalent to that available to persons under no such restriction.

The copy bait of the invention, which comprises native gellan gum and water, has the property that even if dehydrated, it reconstitutes itself quickly upon immersion in water. Therefore, it can be used in such a way that the copy bait previously dried to make it easy to carry about and handle is immersed in seawater or freshwater and used as a copy bait.

The copy food having an abalone-like mouth feel in accordance with the invention was implemented as the result of development of a new method of producing a gel composition containing native gellan gum dissolved uniformly and in a high concentration.

The invention, therefore, provides a method of producing a gel composition containing native gellan gum in a high concentration.

The conventional method of producing a gel composition generally comprises preparing a high-fluidity aqueous dispersion of the gelling agent in the first place and then heating it under constant stirring, for instance, to provide an aqueous solution. However, the maximum concentration that can be achieved by this method is not beyond the level at which gelation or an unmanageably high viscosity develops in the course of preparation (usually 4 weight %). In the case of native gellan gum, too, when its concentration is about 3 weight %, the dispersion develops a high degree of elasticity during heating and agitation in water to make further stirring difficult. Therefore, it has been considered impossible or unrealistic to prepare a gel composition containing 4 weight % or more of native gellan gum.

In accordance with the method of this invention, native gellan gum is heated in the presence of water, whereby a gel composition containing native gellan gum in a high concentration range of, for example 4~30 weight %, can be provided.

Here, the phrase "native gellan gum in the presence of water" means at least the condition in which native gellan gum is in contact with water, regardless of whether the gum has been dispersed in water or exists in a condition segregated from water, only excluding the case in which native gellan gum is spatially isolated from water. This is because when not in contact with water, native gellan gum cannot undergo gelation if heated. However, the condition in which native gellan gum is not in contact with liquid water but in contact with water vapor and, hence, able to form a gel is subsumed in the concept of "in the presence of water". In this case, the formulating amount of native gellan gum relative to water is calculated on the basis of the water which will have contacted with the gum and become a constituent of the gel. As rule of the thumb, the percentage of the weight of native gellan gum prior to contact with water relative to the weight of the gel is calculated as the formulating amount of native gellan gum.

Only provided that native gellan gum gives rise to a gel, the heating temperature and time and pH are not particularly restricted. Taking a simple system consisting exclusively of native gellan gum and water as an example and when the ratio of native gellan gum to water is 10:90, the heating temperature and time may for example be 80° C. and 10 minutes, respectively. The optimum conditions are dependent on the formulating amount of native gellan gum, the salt concentration of the system, and other concomitant ingredients but may generally be 75~100° C. under atmospheric pressure and 5~60 minutes. Those conditions can be properly selected and adjusted by one skilled in the art.

The gel of such high native gellan gum content may be supplemented with seasonings, acidulants, colors, flavors, etc. in the presence of water. Moreover, it may contain boiled adzuki-beans, fruit pulps and other food ingredients. When such food ingredients are added, the ingredients will be present randomly in the native gellan gum gel. To insure a uniform dispersion of food ingredients in the gel, the system can be kneaded during heating or immediately before heating.

(5) Cold Retention Composition and Cold Retaining Agent

The invention relevant to this embodiment was developed on the basis of the finding that a hydrogel prepared using native gellan gum consistently shows temperatures lower than room temperature by about 4~6° C., thus having a cold retention/cooling action, and further that this gel is possessed of useful properties such as shape-retention properties, water-holding properties, moisture releasing properties, viscosity, and good mold release properties.

The cold retention composition of this invention is characterized in that it contains native gellan gum and water as essential components. The term "cold retention" is used herein to mean the property of a substance which maintains itself at a temperature lower than the temperature of the ambient atmosphere.

The cold retention composition of the invention can be prepared basically by dissolving native gellan gum in water, homogenizing it with heating and agitation, and cooling the resulting gel. Where necessary, propylene glycol, glycerin, a sugar alcohol or a saccharide can be incorporated after agitation under heating. Particularly for protecting the product from being deformed by dehydration, propylene glycol is preferably added.

The sugar alcohol includes but is not limited to mannitol, erythritol and pentitol. The saccharide is not particularly restricted, either, but includes monosaccharides such as glucose, fructose, etc., disaccharides such as sucrose, trehalose, etc., and polysaccharides such as starch.

The cold retention composition of this invention can be prepared either in a gel form or in a sol form according to the properties of liquid components (water and liquid additives such as propylene glycol) used in its production.

For the production of a gel-like cold retention composition, for instance, a typical method may comprise dissolving 0.5~4 weight %, preferably 1~4 weight %, of powdery native gellan gum in water to make 100 weight %. When propylene glycol or the like is added, a typical method may comprise dissolving the above-mentioned amount of native gellan gum in 10~79 weight % of water and adding 20~50 weight % of propylene glycol to the solution to make a total of 100 weight %.

The cold retention composition thus produced loses its constituent water gradually when left standing in an open environment because of its own moisture-releasing properties but the present invention covers such a cold retention composition with reduced water content provided that it still possesses cold retention properties. In this connection, the critical water content of the composition at which a cold or cool sensation can be felt when it is applied against the skin is at least 20 weight % based on the total weight (100 weight %) of the composition.

When propylene glycol or the like is incorporated, its formulating amount is not particularly restricted but can be selected from the range of 20~50 weight % based on 100 weight % of the composition. However, in view of the fact that its amount is reflected in a commensurate decrease in water content, the formulating amount is preferably controlled within the range not adversely affecting the cold retention effect of the composition.

The cold retention composition, particularly cold retention gel composition, of this invention is particularly useful because, in addition to moisture-releasing and heat-absorbing properties and safety, it has such other unique properties as water-holding properties, resistance to aging of water-holding properties, shape-retaining properties, water-absorbing properties, stability against heat, resistance to freezing, and viscosity.

The "water-holding properties and resistance to aging of water-holding properties" mean the property of a substance to contain water therein in stable condition and does not allow oozing or exudation of water even on compression. The gel composition of the invention is capable of holding a maximum of about 200 times the weight of native gellan gum of water in a stable manner.

The term "shape-retaining properties" means the property of a substance which retains its shape without undergoing liquidation or collapsing and the gel composition of this invention has excellent shape-retaining properties even when it contains a comparatively large amount of water as mentioned above.

Furthermore, the cold retention gel composition of this invention has "water-absorbing properties", the property to swell and further absorb water with shape-retaining properties retained when contacted with water anew even when it is already in the condition of containing a large amount of water but not beyond said water content.

Furthermore, the gel composition of the invention has "stability against heat and freezing resistance". Thus, even when accommodated in a sealed container and stored in an incubator at 50 for at least 2 weeks, this gel composition retains its shape without showing any remarkable exudation of water which would normally occur due to syneresis. Moreover, even when it is left standing in the freezer at −18° C. for 24 hours, the composition does not lose the elastic property characteristic of the gel. Little water separation is observed, either, when the composition is housed in a sealed container and stored at −18° C. for at least 2 weeks. It is, thus, apparent that the gel composition of the invention fully withstands atmospheric-temperature distribution in a sealed condition and can be put to use as frozen or chilled or be stored frozen.

Moreover, as its further meritorious feature, the gel composition of this invention has "adhesive properties" of its own so that it can be bonded directly to the skin or other surface but leaves no residues after removal by peeling.

Regardless of whether it is a gel or not, the cold retention composition of the invention has moisture-releasing properties, that is to say the property to release water by evaporation from its surface with time. This evaporation of water deprives the composition of the latent heat of evaporation, with the result that the composition continues to show temperatures lower than ambient atmospheric temperature at all times. Thus, the cold retention composition of the invention has heat-absorbing and cooling properties.

Furthermore, the cold retention composition of the invention has an adequate degree of moisture releasing properties. This characteristic of the composition is advantageous in that while it functions a sort of humectant when applied to the human skin, it does not cause skin maceration, redness or rash at the application site.

Moreover, since the cold retention composition of the invention comprises native gellan gum, which can be even ingested safely as it is, as a major component, it can be affixed directly to the skin without health hazards.

In addition, this cold retention composition can be reduced in size by drying and the dehydrated composition is able to reconstitute itself into the initial gel composition in a brief time with good reproducibility when contacted with water again.

The present invention covers such a dehydrated composition, that is to say the composition available upon dehydration of said cold retention composition.

This dehydrated composition has no cold-retaining properties by itself but absorbs water to express cold-retaining properties. This composition is advantageous in that, because it is dry, it can be conveniently carried about or handled, does not take space for storage because of its compact form, and can be readily transformed into a cold retention or cooling composition by mere immersion in water as needed.

The dehydration treatment is not particularly restricted but can be carried out by the conventional method, such as heat treatment. The degree of dehydration is not particularly restricted but the composition is preferably dehydrated to the extent that it is substantially free of water.

The cold retention composition which can be submitted to such dehydration treatment is not particularly restricted but may be any kind of cold retention composition described hereinbefore. The preferred composition is a composition containing at least one member selected from the group consisting of propylene glycol, glycerin, sugar alcohol and saccharide in addition to native gellan gum and water. The more preferred composition is a composition comprising native gellan gum, water and propylene glycol. By including propylene glycol or the like, the deformation attributable to dehydration can be prevented.

Exploiting the above characteristics of the cold retention composition, the present invention further provides a cooling agent containing said cold retention composition or dehydrated cold retention composition.

The term "cooling agent" as used in this specification means any and all substances or artefacts which are used with cooling or cold retention as one of their objectives, thus including not only cooling/cold retention agents which are used with cooling or cold retention as a primary objective but also plasters, poultices, cosmetic packs, etc. which are used with cooling/cold retention as a secondary expected effect.

The cooling agent of this invention is not particularly limited to any specific form but may have a variety of forms suited to the object to be cooled. As a few typical examples, there can be mentioned (i) the cold retention gel composition described above, preferably in a sheet form.
(ii) an artefact comprising the cold retention composition disposed on a supporting layer or sheet.
(iii) an artefact comprising said cold retention composition as sealed in a sealable container or bag, such as a PVC bag, a moisture-proof aluminum pouch or the like.

However, the above is not an exhaustive list. The composition mentioned above may be said dehydrated composition which is available upon dehydration of the cold retention composition. The dehydrated composition, when dipped in water, is ready to function as a cooling agent.

The cold retention composition used in the above application (iii) may be any of a sol, a gel, or a liquid.

The cooling agent in the form (i) or (ii) finds application as cooling/cold retention sheets to be applied to the human body for the primary object of imparting coldness or coolness or mitigating hot flushes, as plasters or poultices to be applied with the expectation of medicinal efficacy, and as cosmetic packs applied for cosmetic effects, among other uses.

The cold retention composition for use in those applications may be supplemented with antiseptics/anti-bacterial agents such as benzethonium chloride, benzalkonium chloride, cetylpyridinium chloride, chlorhexidine gluconate, Biosol, etc., perfumes such as 1-menthol etc., coloring agents, and other additives. As to the cooling agent for medical use, it. may contain medicinally active ingredients according to the intended medical applications, for example local anesthetics such as dibucaine hydrochloride, prilocaine hydrochloride, benzocaine, lidocaine, etc., antiinflammatory agents such as cortisone, prednisolone, betamethasone, etc., antihistaminics such as chlorpheniramine maleate, diphenhydramine hydrochloride, guaiazulene sulfonate sodium, hemostatics such as naphazoline hydrochloride, ephedrine hydrochloride, etc., wound healing accelerators such as aloe, ichthammol, hinokitiol, glycyrrhizic acid, urea, etc.

The cooling agent adapted to serve cosmetic purposes as well may contain the ingredients which are generally used in cosmetic products, for example humectants (e.g. polyethylene glycol and its derivatives, polypropylene glycol and its derivatives, glycerin and its derivatives, monosaccharides, polysaccharides, etc.), emollient ingredients (e.g. liquid paraffin, squalene, olive oil, etc.), skin care/conditioners such as skin bleaches (e.g. vitamin C, placenta extract, etc.), antiinflammatory agents such as glycyrrhizinates etc., dyes, pigments and antibacterial agents.

The support for use in the form (ii) is not particularly restricted as far as it is capable of supporting and getting impregnated with said gel composition and has an adequate degree of moisture permeability so that the release of moisture from the gel composition will not be hindered. Thus, for example, woven and nonwoven fabrics made of natural fibers such as cotton, linen, wool, etc., cellulosic fibers such as rayon etc., or synthetic fibers such as nylon, acrylics, etc., and films of polyethylene, polypropylene and other plastics can be employed.

The thickness of the support is not critical, either, but can be judiciously selected taking the ease of use into consideration. However, when the cooling agent is to be applied to the skin, the support preferably has an adequate degree of flexibility so that it may easily conform to the skin surface at the application site.

This cooling agent can be applied to the forehead of a person in febrile condition and can also be used for the cooling of the eyelids, legs or feet or as a first-aid disposable cooling agent in the emergency management of bruises and distortions.

While the cooling agent of the above form essentially comprises said cold retention composition and said support, it may further comprise a peel sheet laminated on the surface of the cold retention composition. This peel sheet is removed in using the cooling agent but is useful for preventing dehydration of the cold retention composition, keeping it in a clean and sanitary condition, and improving the ease of handling.

For the manufacture of the cooling agent, the hitherto-known production methods can be selectively used. A preferred method comprises stirring native gellan gum, water and other components evenly to prepare a homogeneous solution and cooling it to provide a cold retention gel composition. The preferred proportion of the liquid fraction is 95~99 weight %.

Then, using an applicator, this gel composition is uniformly spread over the peel sheet and the support is superimposed thereon. In this procedure, the gel composition, which is adhesive by itself, attaches itself securely to the support but the laminate may be pressed with a roller to insure a firmer bond.

Meanwhile, the cooling agent in the form (iii) finds application typically as an agent for the cold storage of vegetables, fruits, drinks, desserts, and other articles which require preservation or as a cooling agent to be applied to the human body for the primary purpose of lowering the body temperature (antipyresis), imparting a cool sensation or controlling hot flushes. When used after temporary storage in the refrigerator, for instance, the cooling agent expresses an improved cooling effect, and after its cooling efficiency has deteriorated, the cooling agent can be refrozen and used again.

(6) Dispersion Stabilizer

The invention relevant to this embodiment was developed on the basis of the finding that native gellan gum is effective in improving the dispersibility of a solid phase (discontinuous phase or dispersoid) in a liquid phase (continuous phase or dispersing medium) and stabilizing the dispersion or improving and stabilizing a heterogenous system consisting of an oil phase and an aqueous phase which are incompatible. Thus, by means of native gellan gum, the uniform distribution of solids in a liquid composition can be maintained and the phase separation of a liquid composition comprising immiscible liquid components can also be inhibited to stabilize the dispersed or homogenized state of said liquid components.

Developed on the basis of the above finding, this invention is directed to the use of native gellan gum as a dispersion stabilizer and to a food processing composition and a processed food product, both stabilized by inclusion of said dispersion stabilizer.

The dispersion stabilizer of this invention is not particularly restricted as far as it contains negative gellan gum.

The dispersion stabilizer of the invention assists in the efficient dispersion of solid substances such as cacao powder, green tea powder, calcium, vegetable and fruit fibers, jelly grains, jelly slices, protein components, plastic beads, pigments, coatings, etc., in aqueous media or mixtures of aqueous media with water-miscible organic solvents and has the function to prevent their flocculation and precipitation.

Generally speaking, an aqueous component and an oily component are immiscible with each other and if a mixture of them is shaken or stirred to give a suspension, the suspension is ready to undergo phase separation. In contrast, when the dispersion stabilizer of this invention is used, the dispersion and homogeneity of an aqueous system containing various components can be maintained in a stable manner and even when an oleaginous component such as salad oil, olive oil, sesame oil or the like is added to such an aqueous system, it is possible to provide a homogeneous mixture by stirring with Homo-mixer or emulsification using a homogenizer and maintain the homogeneity of the mixture. Therefore, the dispersion stabilizer of this invention assists in the efficient dispersion and suspension of oily substances in an aqueous phase and stabilizes the dispersion or suspension to prevent early separation of the two phases.

Thus, the dispersion system to which the dispersion stabilizer of the invention is applicable is not particularly restricted as far as it is a system consisting of a liquid continuous phase and a solid or liquid discontinuous phase, thus including but not limited to food products, compositions for the preparation of food products, fragrance/cosmetic products, dye/pigment compositions, and cement and other industrial compositions.

As specific processed foods for use as substrates, there can be mentioned a variety of beverages such as cocoa drinks, calcium-enriched drinks, green tea powder-containing drinks, drinks containing vegetable or fruit juices, soya milk drinks, jelly-containing drinks, shiruko (adzuki-bean soup)-containing drinks, etc., various soups such as corn soup, potage, egg-containing soup, etc., miso (e.g. fermented bean paste) soup, dressings, tare or sauces and other liquid seasonings, ice cakes such as sherbet-on-a bar and soft cream, cakes, and bakery products such as fruit/nut-containing bread and steamed bread.

In the field of fragrance/cosmetic products, liquid cosmetics such as hair cosmetics, face cleaners, toilet waters, lotions, etc., which contain solid or oily ingredients, can be mentioned as examples. For example, lotions containing pearl powders, gold powders or calamine powders require shaking prior to use so as to liquidate sediments and there also is the problem that as the contents of the product are progressively decreased in repeated use, the solid fraction is increased or the composition of the product is otherwise altered from the original formulation. However, when the dispersion stabilizer of the invention is added, such solid ingredients can be kept uniformly dispersed in the liquid phase over a long time and the initial formulation can be maintained until the product has been completely consumed.

There is no particular limitation on the formulating amount of native gellan gum in such a dispersion system as far as the dispersion does not undergo gelation. Thus, a suitable proportion can be selected according to the type of the dispersion to be stabilized and its component materials. For prevention of the sedimentation of solids in the liquid phase or stabilization of the compatibility of immiscible liquid components, native gellan gum is used in a proportion of generally 0.001~0.15 weight %, preferably 0.005~0.12 weight %, more preferably 0.01~0.1 weight %, all based on 100 weight % of the dispersion system. Where necessary, the dispersion system can be provided with a suitable degree of viscosity by controlling the formulating amount of the dispersion stabilizer. Taking a cocoa drink as an example, when native gellan gum is formulated in an amount of about 0.005~0.1 weight % based on 100 weight % of the drink, a cocoa drink with a delicious taste is obtained and the dispersibility of cacao powder is improved to preclude sedimentation. If the level of addition exceeds 0.12 weight %, the cocoa drink undergoes gelation. Therefore, as far as a cocoa drink or the like is concerned, native gellan gum is preferably formulated in a proportion of about 0.005~0.1 weight % and when it is desired to impart viscosity for the expression of a full-bodied taste, native gellan gum is preferably used in a proportion of 0.1~0.12 weight %.

The dispersion stabilizer of this invention may contain microcrystalline cellulose in addition to native gellan gum.

The "microcrystalline cellulose" means an aggregate of cellulose crystallites which is substantially uniform in the degree of polymerization, which, can be obtained by acid hydrolysis or alkaline hydrolysis of cellulose and includes the grades meeting the definition given in Industrial and Engineering Chemistry, 42, 502–507 (1950). In order that the effect of the invention may be expressed in greater distinction, a microcrystalline cellulose containing at least 5 weight % of particles not greater than 1 microns in Stokes diameter is preferably used. Particularly preferred is a microcrystalline cellulose which can be uniformly dispersed as it is in water by means of a homogenizer or a high-speed mixer.

There may also be employed a preparation which can be obtained by milling microcrystalline cellulose and water soluble gum (e.g. karaya gum, xanthan gum, etc.), carboxymethylcellulose sodium or other optional substances in the presence of water and dehydrating the mixture (Examined Japanese Patent Publication No.112174/1965, Unexamined Japanese Patent Publication No.268129/1995, Unexamined Japanese Patent Publication No.173332/1995, etc.) or an aqueous suspension of finely-divided cellulose particles obtainable by milling a material cellulose in water (Unexamined Japanese Patent Publication No.100801/1981, Unexamined Japanese Patent Publication No.163135/1991, etc.). It is also possible, for convenience's sake, to use commercial products such as "Ceollus (trademark)" SC-42 and "Avicel (trademark)" RC-591, RC-N81, RC-N30, & CL-611 (Asahi Kasei Kogyo), among others.

In such cases, the dispersion stabilizer may contain generally 0.1~5000 weight %, preferably 1~1600 weight %, more preferably 2~50 weight %, of microcrystalline cellulose based on 1 weight % of native gellan gum (on a solid basis).

The relative formulating amounts of native gellan gum and microcrystalline cellulose in the dispersion stabilizer for addition to a dispersion system are dependent on the type and composition of the dispersion system to be stabilized but may generally range-from 0.0008 to 0.1 weight % of native gellan gum and 0.01 to 4 weight % of microcrystalline cellulose, preferably 0.005~0.07 weight % of native gellan gum and 0.07~0.8 weight %, more preferably 0.008~0.05 weight % of native gellan gum and 0.1~0.4 weight % of microcrystalline cellulose, all based on 100 weight % of the dispersion system. Within this range, the prevention of precipitation of solids in the liquid phase and the stabilization of the compatibility of liquid components can be successfully accomplished.

When the dispersion to be stabilized is a fragrance/cosmetic product, the formulating range of native gellan gum relative to 100 weight % of the product is 0.0008~0.1 weight % and that of microcrystalline cellulose is 0.05~1 weight % on the same basis, and significant effects can be expected within those ranges.

The dispersion stabilizer of the invention may contain pectin in addition to native gellan gum. Such a dispersion stabilizer can be used in systems containing high levels of salts and proteins without causing a viscosity gain or coagulation, thus providing homogeneous dispersions. Therefore, this invention is particularly useful as a dispersion stabilizer for implementing low-viscosity fluid foods containing salts and proteins.

The pectin includes both high-methoxy and-low-methoxy pectins and can be used regardless of its type.

Such a dispersion stabilizer may for example be a composition containing pectin in a proportion of generally 0.5~2 weight % (on a solid basis), preferably 0.6~1.6 weight %, more preferably 0.8~1.2 weight % based on 1 weight % of native gellan gum.

This dispersion stabilizer may further contain other polysaccharides such as locust bean gum., tamarind gum, and soya polysaccharide.

The dispersion stabilizer containing native gellan gum and pectin according to this invention, when the objective to be attained is an improvement in dispersibility and stabilization of a dispersion with sustained low viscosity, is preferably used in the presence of a salt.

The "salt" in the context of this invention means any and all salty substances which are generally contained in foods, thus including but not limited to neutral salts such as NaCl, KCl, $NH_4Cl$, NaBr, NaI, etc. and various other salts which are used as substitutes for sodium chloride, such as the sodium salts of malic acid, malonic acid and gluconic acid. The concentration of the salt in this application is not particularly restricted but can be judiciously selected. However, in a system (total: 100 weight %) including a dispersion stabilizer containing 0.4~0.8 weight % of native gellan gum and 0.6~1.6 weight % of pectin, for instance, the amount of the salt in terms of NaCl may for example be 3~20 weight %, more preferably 4~15 weight %.

With this dispersion stabilizer of the invention, food products comparatively rich in salty components, e.g. sodium chloride, for example liquid seasonings, can be maintained in a stable condition without entailing elevation of the intrinsic viscosity of food and regardless of their pH values and food systems rich in proteins and salts can also be maintained in a stable condition with improved and stabilized dispersibility of oil components. Therefore, in accordance with this invention, there can be provided low-viscosity salty foods presenting with light mouth-feels with improved dispersibility of proteineous ingredients which, in particular, have so far been hardly dispersed uniformly.

This invention provides food processing compositions and processed foods which are characterized by comprising native gellan gum alone, native gellan gum and microcrystalline cellulose, or native gellan gum and pectin. The invention further provides fragrance/cosmetic products, dyes and/or pigments, and industrial compositions such as cement, which contain native gellan gum either alone or in combination with microcrystalline cellulose or pectin.

The processed food in the context of this invention means any and all foods each comprising a dispersion of insoluble solid such as cacao powder, green tea powder, calcium, vegetable or fruit fiber, sap-containing endocarps, pulps and proteineous ingredients which are usually contained in soups or shiruko and liquid seasonings, and water-immiscible liquid components as dispersed in water, milk, fruit juices, etc. The processed food includs but not limited to the various drinks, soups, miso soup, liquid seasonings, cakes, and bread mentioned hereinbefore.

By virtue of the native gellan gum, native gellan gum plus microcrystalline cellulose or native gellan gum plus pectin contained, the processed foods of the invention can be shipped for distribution and/or stored for a long time without developing the trouble of settling or separation of solids from the liquid phase during distribution or storage, thus being retained in the original uniformly dispersed form, and can be ingested to enjoy the homogeneous textures and tastes without resort to swirling of the can or bottle or stirring the contents with a spoon, for instance.

The cocoa drink in the context of this invention means any and all food products that contain cocoa powder and are provided for ingestion by drinking. In addition to said dispersing agent, the cocoa drink of the invention may contain sugars, artificial sweeteners, milk components, oil and fat, flavors, emulsifiers, sodium chloride, and coloring materials. The so-called chocolate drink is also subsumed in the concept of cocoa drink. The cocoa powder which can be used in this invention is not particularly restricted. Thus, it does not matter whether it is natural cacao powder or alkali-treated cacao powder or whether or not it contains the fat fraction. For convenience's sake, commercial products which are usually available as dry powders can be utilized. The cocoa drink of the invention may contain cacao powder in a proportion of 0.01~10 weight %, preferably 0.5~5 weight %, based on 100 weight % of the drink.

As the milk component, whole milk, skim milk, the corresponding powdered milks and reconstituted milk can be mentioned by way of example. The cocoa drink of this invention may contain such a milk component in a proportion of 0~10 weight %, on a defatted milk solid basis, relative to 100 weight % of the drink.

When the cocoa drink of this invention contains native gellan gum as a dispersion stabilizer, the formulating amount of native gellan gum may be within the range of 0.005~0.12 weight % based on 100 weight % of the drink. When microcrystalline cellulose is used concomitantly, the preferred formulating amounts are 0.0008~0.1 weight % of native gellan gum and 0.05~1 weight % of microcrystalline cellulose, preferably 0.002~0.07 weight % of native gellan gum and 0.1~0.5 weight % of microcrystalline cellulose.

The calcium-enriched drink in the context of this invention means any drink containing the water-insoluble fraction of calcium. Based on 100 weight % of the drink, the proportion of such insoluble calcium or a calcium-containing compound is generally 0.01~5 weight %, preferably 0.02~3 weight %, in terms of calcium. To stabilize a dispersion containing insoluble calcium, it is sufficient to incorporate 0.005~0.12 weight % of native gellan gum based on 100 weight % of the drink. The level of native gellan gum in the case of using 0.05~1 weight % of microcrystalline cellulose in combination may range from 0.0008 to 0.1 weight %.

In the drink containing a vegetable or fruit juice according to this invention, the corresponding fruit fiber, sap-containing endocarps and/or pulp can be incorporated generally within the range of 0.01~80 weight % based on 100 weight % of the drink. The native gellan gum content of such a drink may be 0.005~0.12 weight % based on 100 weight % of the drink and, when 0.05~1 weight % of microcrystalline cellulose is concomitantly used, may be 0.0008~0.1 weight %.

The milled green tea content of the green tea powder-containing drink may generally range from 0.01~10 weight %, preferably 0.5 to 3 weight %, based on 100 weight % of the drink. For the improved dispersion and stabilization of milled green tea, 0.005 to 0.12 weight % of native gellan gum may be incorporated. When 0.05~1 weight % of microcrystalline cellulose is concomitantly used, the native gellan gum content of the drink may range from 0.0008 to 0.1 weight %.

The corn content of the corn soup according to the invention is generally within the range of 0.01~10 weight %, preferably 0.5~3 weight %, based on 100 weight % of the drink. For the improved dispersion and stabilization of corn, native gellan gum may be contained in a proportion of 0.005~0.12 weight %, and when 0.05~1 weight % of microcrystalline cellulose is used in combination, the proportion of native gellan gum may range from 0.0008 to 0.1 weight %.

The adzuki-bean component content of the shiruko soup is generally 0.01~10 weight %, preferably 0.5~3 weight %, based on 100 weight % of the soup. For the purpose of stabilizing the dispersion of adzuki-bean fragments and starch particles, it is sufficient to incorporate 0.005~0.12 weight % of native gellan gum, and when 0.05~1 weight % of microcrystalline cellulose is concomitantly used, the level of native gellan gum may be 0.0008~0.1 weight %.

The liquid seasoning includes dressings and the like which contain both an aqueous component and an oily component incompatible therewith and goma-dare (sesame-containing sauce) and the like which comprise dispersions of protein-derived insoluble solids in liquid media. In the former case, the native gellan gum content of the dispersion stabilizer not containing any concomitant component is 0.005~0.12 weight % based on 100 weight % of the aqueous fraction of the food. When microcrystalline cellulose is used concomitantly, the recommended levels are 0.0008~0.1 weight % for native gellan gum and 0.05~1 weight % for microcrystalline cellulose, preferably 0.002~0.07 weight % for native gellan gum and 0.1~0.5 weight % for microcrystalline cellulose. In the case of dressings based on salad oil, the preferred amount of salad oil is 0.01~50 volume parts based on 100 volume parts of the dressing but the oil level may be increased where needed.

In the latter case, particularly the case of a goma-dare which needs to have a thin fluid mouth-feel, the dispersion stabilizer comprising native gellan gum and pectin is used with advantage. The formula for this dispersion stabilizer may vary with different concentrations of the salt contained in foods but when the salt concentration is within the range of 4~10 weight %, the formulation of 0.08~0.4 weight % of native gellan gum and 0.6~1.6 weight % of pectin can be recommended. In this case, even when a sesame paste, which is an insoluble matter, is contained in the range of 10~20 weight %, the paste can be dispersed in a stable manner without sedimentation or coagulation.

The food processing composition in the context of this invention broadly includes the compositions for use in the production of said processed foods and the compositions which, regardless of the form of processed food, are each by themselves in the form of a dispersion of solid components in a liquid medium or incompatible liquid components in a liquid phase.

As the former compositions, cacao powder, shiruko powder, powdered drinks (milled green tea-containing drinks, calcium-enriched skim milk, etc.), and powdery or solid soups, all of which are commonly called instant foods (dry formulas), can be mentioned as typical examples. By incorporation of the dispersion stabilizer of this invention in those foods, early disintegration on saturation with cold water or hot water (boiling water) and improvements in dispersibility or suspendability can be expected and, moreover, the problem of separation of a thin supernatant or formation of bottom sediments at the time of ingestion can be avoided even if the prepared food is left standing for a while. In this respect, the dispersion stabilizer of this invention is of great use.

As to the latter case, concentrates of liquid drinks (e.g. cocoa drink, milled green tea drink, fruit juice drink) and compositions for the preparation of bread, steamed bread and cakes can be mentioned. The dispersion stabilizer of the invention is useful in that when it is incorporated, uniform dispersions of dispersoids can be obtained in such food processing compositions. Moreover, food products in which dispersoids are uniformly distributed with little variation in a stable manner can be produced.

The present invention is further concerned with a method of producing a processed food which comprises adding native gellan gum, native gellan gum plus microcrystalline cellulose, or native gellan gum plus pectin in the course of production of said food.

The processed food mentioned above includes the drinks, soups, seasonings and foods mentioned hereinbefore and preferably includes food products which are supplied in cans, bottles, or packs for distribution in sealed condition.

The method according to this invention comprises adding native gellan gum, native gellan gum plus microcrystalline cellulose, or native gellan gum plus pectin as a dispersion stabilizer to a raw material formula in the preparation of processed foods, specifically in the stage of formulation or in the mixing stage.

The level of addition of said dispersion stabilizer may vary with the type of food product but can be judiciously selected from the range in which the food is not caused to form gels by the addition of native gellan gum. The specific range may be the same as mentioned hereinbefore.

In case native gellan gum and microcrystalline cellulose are used in combination, too, their proportions are similarly selected from the range mentioned hereinbefore.

Preparation of a cocoa drink, for instance, can be carried out in the conventional manner except that the production process includes a step of formulating native gellan gum or formulating native gellan gum and microcrystalline cellulose. Specifically, the dispersing agent of the invention is first dissolved in an aqueous medium such as made-up water, milk or reconstituted milk at 20~100° C. and stirred. To this solution, an emulsifier, sugar, sweetener, etc. are added and admixed. Optionally milk components and oil/fat are further added. Thereafter, cacao powder is added and the mixture is homogenized by stirring. The mixture is then pasteurized or sterilized at about 140° C. for 2~3 seconds, at the end of which time it is cooled. By the above procedure there can be provided a cocoa drink having a rich flavor which can be distributed and stored at atmospheric or room temperature. When the formulating ingredients are powdery, it is possible to use the procedure which comprises preparing a premix in the first place by blending the cacao powder, sweetener, dispersant, powdered milk, etc., dissolving the premix in an aqueous medium such as made-up water to prepare a homogeneous solution, pasteurizing the solution and finally cooling it.

On the other hand, when a stabilizer comprising native gellan gum and pectin is used as said dispersion stabilizer, it is preferable that the production process include a step of adding a salt to an aqueous system containing the stabilizer at an elevated temperature.

The aqueous system mentioned above is not particularly restricted as far as it does not contain said salt. Thus, for example, it may be a solution containing food components other than the salt. The dispersion stabilizer of the invention can be easily dissolved by stirring it in an aqueous medium generally under heating or warming. The addition of the salt is performed at a temperature over a certain level, for example 75° C. or higher, preferably at 80~95° C., more preferably at 85~95° C. There is no particular limitation on the food products which can be produced by the above method but includes salty foods as preferred examples. The effect of the invention is expressed with particular prominence in systems rich in protein and salt. The more preferred substrate food products are low-viscosity, highly fluid foods.

The present invention is further concerned with a method of stabilizing dispersions which comprises using the above-mentioned dispersion stabilizer. Particularly, the dispersion stabilizing method of this invention is characterized in that when a stabilizer comprising native gellan gum and pectin is used as the dispersion stabilizer, the production process further includes a step of dissolving the stabilizer in an aqueous system in advance and adding a salt at an elevated temperature of 75° C. or higher, preferably 80~95° C., more preferably 85~95° C.

(7) Thickened Composition Additive

The invention relevant to this embodiment was developed on the basis of the finding that, in the presence of a certain polysaccharide such as xanthan gum or tamarind seed gum, native gellan gum acts as a synergist to remarkably enhance the thickening effect of the polysaccharide without causing gelation.

As the thickener for food and other products, polysaccharides such as xanthan gum, guar gum, locust bean gum, pectin, tamarind seed gum, carrageenan, and gellan gum have been conventionally used. However, when any of those substances is used in solution, the solution becomes too viscous to work with at its concentration of as low as 2-several weight %. Therefore, it has been virtually impossible to impart a required degree of viscosity to a substrate composition using a thickened solution of high concentration at a low addition level so as not dilute the substrate. Therefore, there has been a standing demand for the development of a thickened composition stabilizer by which the substrate composition might be thickened to a high viscosity level at a low level of addition without causing gelation or affecting the constitution of the substrate composition and which would be easy to handle or work with in commercial production lines.

The above-mentioned characteristics of native gellan gum meet this demand.

Based on the above-mentioned findings, this invention provides the use of native gellan gum as a thickened composition additive. The invention further provides a thickening method which comprises using native gellan gum under specified conditions and a thickened composition obtainable by using said thickened composition additive or said thickening method.

The additive according to this invention is intended for use in the preparation of thickened compositions. This thickened composition additive is characterized in that it is used in the presence of a specified polysaccharide or equivalent.

Here, the thickened composition to which the invention can be applied is a composition having a suitable degree of viscosity in one or another stage in the production process for an end product, i.e. regardless of stages of production, and, as such, it may be an end product itself or a composition for use in the production of an end product. Specifically, said thickened composition broadly includes those end. products which are required to have necessary degrees of viscosity and either starting compositions or intermediate compositions for which certain degrees of viscosity are required in one or another stage of production although the end products themselves need not necessarily be viscous.

More particularly, such end products as foods, paints, inks, concrete, etc. and the compositions used for the production of such end products can be mentioned. Preferred are drinks, confections, desserts, tare (sauce) and other foods and compositions for the production of such foods. In this specification, those end products and compositions are collectively referred to as thickened compositions or thickened food compositions.

The polysaccharide or equivalent which can be used in this invention includes tamarind seed gum, tara gum, glucomannan, xanthan gum, locust bean gum, pullulan, guar gum, iota-carrageenan, HM pectin, LM pectin, tragacanth gum, microcrystalline cellulose, PGA (propylene glycol alginate), SSHC (water-soluble soya polysaccharide), ghatti gum, methylcellulose, psyllium seed gum, and caccia gum, among others. Those polysaccharides and equivalents can be used each alone or in a combination of two or more dissimilar species.

While it depends on the objective and the substrate composition to be thickened, the preferred polysaccharides and equivalents from the standpoint of thickening power are tamarind seed gum, tara gum, glucomannan, xanthan gum, locust bean gum, pullulan, guar gum, tragacanth gum, microcrystalline cellulose, propylene glycol alginate, water-soluble soya polysaccharide, methylcellulose, psyllium seed gum and caccia gum. Particularly-preferred, among them, are tamarind seed gum, tara gum, glucomannan, xanthan gum, locust bean gum and pullulan.

The above-mentioned polysaccharides and equivalents are not limited by the degree of purification but may contain contaminants as far as the effect of the invention can be expressed. Taking glucomannan as an example, even low-purity konjak powder is subsumed in the concept of polysaccharide and equivalent insofar as the effect of the invention is expressed.

The above polysaccharides and equivalents are preferably used selectively according to the pH of the thickened composition. Generally speaking, polysaccharides and equivalents other than xanthan gum and cassia gum are used preferably for thickened compositions within the range of pH 2.5~8, preferably pH 3~7, more preferably pH 4~7. The use of xanthan gum alone is suited for thickened compositions within the range of pH 2.5~5 and the use of caccia gum alone is recommended for thickened compositions within the range of pH 5~8.

The combination and amount of polysaccharides and/or equivalents are not particularly restricted but can be judiciously selected and adjusted according to the kind and intended use of the thickened composition.

The phrase "used in the presence" as used in this specification means that as far as any of said specified polysaccharides and/or equivalents and native gellan gum are used in combination for a thickened composition the viscosity of which is to be increased, there is no limitation on the mode of use of this thickened composition additive. Thus, this thickened composition additive can be used by adding it to a substrate composition system already containing said polysaccharide and/or equivalent or adding it to the substrate system concurrently with the addition of said polysaccharide and/or equivalent, or even by blending it with said polysaccharide and/or equivalent and adding the mixture to the substrate system.

The amount of the thickened composition additive of the invention to be used in the presence of the polysaccharide and/or equivalent and the ratio of the additive to the polysaccharide and/or equivalent are not particularly restricted as far as the effect of the invention can be expressed and can be freely selected according to the kind and desired viscosity of the final thickened composition and the kind of polysaccharide or equivalent to be employed.

When the thickened composition is a food, the concentration ranges shown below for native gellan gum and polysaccharides (singular use mode) in Table 1 can be used as references.

TABLE 1

| | Concentration range in which a thickening effect can be obtained in aqueous solution* (wt. %) | Preferred concentration range (wt. %) |
|---|---|---|
| Native gellan gum | 0.01~0.1 | 0.05~0.7 |
| Tamarind seed gum | 0.05~0.1 | 0.1~0.5 |
| Native gellan gum | 0.01~0.1 | 0.05~0.1 |
| Tara gum | 0.05~0.5 | 0.05~0.4 |
| Native gellan gum | 0.01~0.1 | 0.05~0.3 |
| Glucomannan | 0.03~0.5 | 0.05~0.3 |
| Native gellan gum | 0.01~0.15 | 0.01~0.1 |
| Locust bean gum | 0.05~0.7 | 0.08~0.5 |
| Native gellan gum | 0.01~0.1 | 0.01~0.1 |
| Guar gum | 0.03~0.4 | 0.06~0.3 |
| Native gellan gum | 0.01~0.1 | 0.01~0.1 |
| Pullulan | 0.5~7 | 1~5 |
| Native gellan gum | 0.01~0.1 | 0.01~0.1 |
| Xanthane gum** | 0.01~0.5 | 0.03~0.3 |
| Native gellan gum | 0.01~0.1 | 0.01~0.1 |
| Iota-carrageenan | 0.01~0.4 | 0.03~0.3 |
| Native gellan gum | 0.01~0.1 | 0.01~0.1 |
| Tragacanth gum | 0.05~2 | 0.1~1.5 |
| Native gellan gum | 0.01~0.1 | 0.01~0.1 |
| Microcrystalline cellulose | 0.05~3 | 0.1~3 |
| Native gellan gum | 0.01~0.1 | 0.01~0.1 |
| PGA | 0.1~2 | 0.5~2 |
| Native gellan gum | 0.01~0.1 | 0.01~0.1 |
| SSHC | 0.1~10 | 0.1~5 |
| Native gellan gum | 0.01~0.1 | 0.01~0.1 |
| Ghatti gum | 0.05~2 | 0.3~1.8 |
| Native gellan gum | 0.01~0.1 | 0.01~0.1 |
| Methylcellulose | 0.01~2 | 0.1~1.5 |
| Native gellan gum | 0.01~0.1 | 0.01~0.1 |
| Psyllium seed gum | 0.1~1 | 0.2~0.7 |
| Native gellan gum | 0.01~0.1 | 0.01~0.1 |
| Cassia gum** | 0.05~1 | 0.1~0.5 |

*Deionized water is used.
**Adjusted to pH 3.5 with trisodium citrate

The concentration range for each polysaccharide or equivalent on a singular use mode in combination with native gellan gum are shown above but since the salt concentration and constitution of the substrate vary from one food to another, the above concentration ranges may not be optimal ranges for all kinds of foods. Therefore, the ratio of native gellan gum to the polysaccharide and/or equivalent should be determined in each case without being restricted by the above-mentioned ranges so that the desired viscosity may be obtained for each food using said ranges as references.

The thickened composition additive of the invention may be an additive comprising both native gellan gum and one or more species of said polysaccharide and/or equivalent.

The amounts and proportions of native gellan gum and said polysaccharide and/or equivalent in such an additive should vary according to the kind of thickened composition, among other factors, and are not particularly restricted as far as the desired thickening effect on the substrate composition can be expected. Preferably, with regard to the formulating ratio of native gellan gum to said polysaccharide and/or equivalent, the proportions shown in Table 1 can be used as references.

The thickened composition additive of this invention may contain other components without limitation only insofar as it contains native gellan gum, optionally native gellan gum and said polysaccharide and/or equivalent. Taking a thickened food composition additive as an example, it may contain other food components, preservatives for food use, and other additives such as flavors, antioxidants, coloring materials, etc.

This invention further provides a thickened food composition obtainable by processing a raw material batch in the presence of native gellan gum and one or more polysaccharides and/or equivalents selected from the group consisting of tamarind seed gum, tara gum, glucomannan, xanthan gum, locust bean gum, pullulan, guar gum, iota-carrageenan, tragacanth gum, microcrystalline cellulose, propylene glycol alginate, water-soluble soya polysaccharide, ghatti gum, methylcellulose, caccia gum, and psyllium seed gum.

Here, the thickened food composition of this invention not only includes foods which have been thickened as such but also preparations which have been thickened in the course of production of foods and compositions thickened for use in the production of end-product foods.

Thus, drinks, confections, desserts, tare (sauce) etc. can be mentioned by way of example. Moreover, said compositions for use in the production of thickened foods include but are not limited to sets of the assorted materials necessary for the preparation of thickened foods, which are blended, diluted with water or supplemented with sugar etc., and finally heated or chilled at home to serve as finished foods.

The amounts and formulating ratio of said polysaccharide and/or equivalent and native gellan gum in the thickened food composition of this invention vary according to the kind of thickened food composition, among other factors, and are not particularly restricted. Preferably, however, the formulating ratios indicated in Table 1 are used.

The present invention is further directed to a method of thickening foods which comprises causing at least one member selected from among the above-mentioned polysaccharides and equivalents and native gellan gum to be concurrently present in the system.

The method of thickening a food in accordance with this invention is not particularly restricted only if it is capable of insuring that native gellan gum and said specified polysaccharide or equivalent will be concurrently present in the food the viscosity of which must be increased. Thus, all that is necessary-is that native gellan gum and said polysaccharide or equivalent be formulated and incorporated to provide an effective viscosity within the range not causing gelation in the food or in the course of its production and there is no particular limitation on the timing or order of addition.

A preferred method comprises preparing a solution containing native gellan gum and said polysaccharide and/or equivalent ahead of time and adding the solution, as it is or together with water, to the substrate food. A still-more preferred method comprises preparing a solution of native gellan gum and a solution of said polysaccharide and/or equivalent independently in advance and adding them to the food.

The relative amounts of native gellan gum and said polysaccharide and/or equivalent can be judiciously selected and adjusted with reference to the proportions indicated in Table 1.

In accordance with the method of this invention, native gellan gum and said specified polysaccharide and/or equivalent, which are low in viscosity and easy to work with, are used to impart the desired high viscosity to a food through their synergistic action. Thus, unlike the conventional technology, the food-thickening method of this invention is free from the limitation imposed by the high viscosity of thickeners and, therefore, can be used conveniently and with good workability on a commercial scale.

(8) Heat Resistance-imparting Agent

The invention relevant to this embodiment was developed on the basis of the finding that native gellan gum has the property to impart heat resistance, particularly resistance to retort treatment, to foods. The retort treatment of tofu (soybean curd), among various foods, for sterilization not only induces separation of water-from tofu but also roughens its texture to jeopardize the inherent characteristics of tofu and, hence, detract from its unique mouth-feel and taste. Therefore, the retort technique has not been applied to this food.

However, developed on the basis of the findings mentioned above, this invention provides the use of native gellan gum as a heat resistance-imparting agent, particularly a retort resistance-imparting agent. The invention further provides tofu stabilized against retort treatment with said agent and heat-sterilized tofu which is obtainable by subjecting said stabilized tofu to retort or equivalent treatment and can therefore be stored for a long time at room temperature.

The phrase "tofu stabilized against retort treatment" in the above description means tofu whose properties (texture etc.) and palatability are not affected even by retort treatment to say the least, that is to say tofu which is resistant to retort treatment.

The retort treatment is a treatment applied to certain foods for allowing them to be stored for a long time or at room temperature and specifically a pasteurization or heat sterilization procedure carried out under atmospheric or higher atmospheric pressure can be mentioned. To be specific, it may for example be a method of treating foods at 1~2 kg/cm$^3$ and 110° C. ~130° C. for 10~30 minutes.

The retort-resistant tofu according to this invention can be manufactured by the conventional production technology using the ordinary main raw materials (beans, coagulant, etc.) which are commonly used in the industry except that it contains native gellan gum.

Taking momen-tofu (coarse-texture soybean curd) as an example, the tofu is generally manufactured by the following steps.

(1) Crush water-soaked soybeans with addition of water until a mushy consistency has been obtained.
(2) Add several volumes of water and heat to prepare go (magma).
(3) Filter the go through a cloth to provide soya milk.
(4) While the soya milk is still hot, add a coagulant [nigari (bittern), calcium sulfate or the like] (about 2~3% based on soybeans) suspended in water and allow to stand to let the protein be coagulated (this is referred to as a stock tofu preparation).
(5) Remove the supernatant, cast the coagulated protein in a mold, and put a weight thereon for drainage.
(6) Then, take out from the mold and rinse in running water to dissolve out the excess coagulant to provide tofu.

In the production of the tofu of this invention, regardless of its variety, e.g. said momen-tofu, kinukoshi (fine-textured)-tofu, or packed tofu, it is sufficient to add native gellan gum so that it will be contained in the stock tofu preparation prior to coagulation at latest in the above procedure. Thus, the gum may be added to soya milk before addition of the coagulant or as far as the tofu protein remains to become coagulated yet, it may be added after addition of the coagulant.

There is no particular limitation on the coagulant for use in this invention but may be any substance capable of causing coagulation of protein in the soya milk. As specific examples, calcium sulfate and magnesium chloride which are commonly used in the production of tofu can be mentioned. However, glucodeltalactone which is used as the coagulant for packed tofu is not desirable because it undergoes said pyrolysis.

The amount of native gellan gum occurring in the tofu of this invention is usually selected and controlled, within the range of 0.005~0.25 weight % based on 100 weight % of tofu, according to the desired taste, but when it is at least within the range of 0.0~0.12 weight %, the tofu expressing the effect of the invention while maintaining the ordinary mouth-feel of tofu can be obtained. The more preferred range is 0.02~0.11 weight % and the still more preferred range is 0.05~0.11 weight %.

When the amount of native gellan gum is less than 0.01 weight %, a change in mouth-feel is noted after retort treatment but even this mouth-feel is still superior to that of tofu prepared without addition of the gum. At concentrations over 0.12 weight %, the tofu itself is somewhat elastic, thus differentiating itself slightly from regular tofu in palatability. However, when an elastic grade of tofu is desired, it is rather preferable to add more than 0.12 weight % of the gum. Thus, its proportion should be adjusted according to the manufacturer's or consumer's taste.

The tofu of this invention can be ingested as it is to enjoy its savory taste but by exploiting its retort resistance characteristic, it can be further subjected to retort treatment and used as a tofu material for the production of tofu which withstands long-term and room temperature storage.

Therefore, this invention is further concerned with the tofu obtainable by subjecting said tofu material to pasteurization (heat sterilization) at atmospheric or higher atmospheric pressure.

The pasteurization treatment is not particularly restricted as far as it is a heat sterilization carried out at a high temperature under atmospheric or supra-atmospheric pressure but is preferably a retort sterilization or equivalent treatment. An exemplary pasteurization method comprises charging a mold or a deformable container such as a pouch with said tofu material with or without subsequent sealing and heat-sterilizing it under atmospheric or supra-atmospheric pressure (1~2 kg/cm$^3$) at a temperature over 100° C., preferably about 110~140° C., more preferably about 110~120° C., for about 10~30 minutes.

The tofu obtainable by the above method retains the properties and mouth-feel of the tofu material prior to pasteurization and yet can be stored for a long time and/or at room temperature, thus providing for large production and storage during distribution. Incidentally, the tofu of this invention in sealed condition-retains its quality fully at room temperature (23° C.) for at least 2 months.

Furthermore, the tofu having the above-mentioned characteristics can also be produced by a method which comprises filling a vessel with the tofu preparation obtained in the above-described production process, sealing the vessel, and directly pasteurizing it.

Therefore, the present invention provides a tofu withstanding long-term and/or room temperature storage as produced by the above method. Specifically, this tofu according to the invention can be produced by a production process which comprises adding native gellan gum to soya-milk in advance, heating the mixture at 85° C. with stirring for 10 minutes, adding a coagulant when said mixture has cooled spontaneously to about 60° C., filling the coagulated mixture into a retort-resistant vessel and subjecting it to said pasteurization treatment.

(9) Syneresis Inhibitor

The invention relevant to this embodiment was developed on the finding that native gellan gum has a unique property to entrap the liquid contained in a gel composition stably within the composition.

Developed on the above finding, this invention provides the use of native gellan gum as a syneresis inhibitor. Furthermore, this invention provides a method of inhibiting syneresis which comprises using native gellan gum and a gel composition inhibited against syneresis as produced with said inhibitor or by said syneresis inhibiting method.

The perennial problem of "syneresis", separation of water with time from gel-like foods inclusive of jellies, mizu-yokan (soft adzuki-bean jelly), jams, etc., which detracts from quality and appetizing potency,-has so far been frequently pointed out and the advent of a method for preventing or arresting syneresis has been awaited in earnest. This invention meets this demand.

The "gel composition" in the context of this invention means a composition which contains a large amount of liquid but retains its shape without loss of liquid under its own weight and which is entirely or partially composed of a gelling agent. The gelling agent mentioned just above means a gel-forming polysaccharide such as, for example, agar, carrageenan, gellan gum, starch, pectin, curdlan, gelatin, and furcellaran.

The syneresis in the context of this invention means the phenomenon that the liquid held in a gel oozes out from the gel with time.

The "liquid" mentioned in the above description of the "gel composition" and "syneresis" means an aqueous component inclusive of water and includes both of "water" and "any liquid obtainable by dissolving or emulsifying in water a sugar, polysaccharide, preservative, flavor, dye, condiment, emulsifier and/or the like which can be dissolved or emulsified in water".

The substrate for this invention may be any gel composition in which syneresis is abhorred, thus including a broad range of substrates in the fields of food, daily necessities such as toothpastes, and architectural materials such as paints and cement.

Specifically, the food to which this invention is applicable includes but is not limited to the following.
(1) Fish and meat products pumped or impregnated with a gelling agent such as a pickle (for example, sausages, hams, pork cutlets, hamburgers, etc.)
(2) Meat buns and sandwiches containing a gelling agent
(3) Kneaded products such as horseradish paste, mustard paste, ginger paste, etc.
(4) Yoghurts containing a gelling agent
(5) Agar products such as mizu-yokan (soft adzuki-bean jelly), jams such as strawberry jam, marmalade, etc., and jellies such as wine jelly, coffee jelly, fruit jelly, etc.

All of the above-mentioned products are foods which tend to suffer from syneresis during storage, for instance, and the marketability of which is decreased from the standpoint of appearance and taste.

The gel composition of this invention is useful in that the separation of water can be significantly inhibited without detracting from the inherent characteristics of the gel composition, e.g. elasticity, strength, taste and flavor, to thereby uphold the quality of the food.

For example, an orange jelly as the gel composition inhibited against syneresis according to this invention shows no evidence of syneresis even after 1 week's storage in the refrigerator at 5° C. but retains the freshness, mouth-feel and smoothness observed immediately after production.

Furthermore, a toothpaste as the gel composition inhibited against syneresis according to this invention, for instance, does not reveal separation of water around the lip of a tube similar to the tube used for commercial toothpastes even after one month of ordinary use at room temperature but retains the quality fresh from production. At the same time, this toothpaste is free from the stickiness which is normally observed when polysaccharides are added, thus giving a pleasing feel in use.

The amount of native gellan gum in such a gel composition of the invention should vary according to the kind of food or other product, the kind of gelling agent used, and the water content of the product but it can be judiciously selected from the range of generally 0.1~200 weight %, preferably 1~100 weight %, more preferably 2~100 weight %, all based on 100 weight % of the gelling agent in the gel composition.

Specifically when kappa-carrageenan is used as the gelling agent, the preferred amount of native gellan gum relative to 100 weight % of this gelling agent is generally 1~100 weight %, particularly 5~50 weight %.

When the gelling agent is agar, the preferred amount of native gellan gum relative to 100 weight % of agar is generally 1~100 weight %, preferably 2~50 weight %.

When the gelling agent is gellan gum, the preferred amount of native gellan gum relative to 100 weight % of gellan gum is generally 1~100 weight %, particularly 10~100 weight %.

When the gelling agent is starch, the preferred amount of native gellan gum relative to 100 weight % of starch is generally 0.1~200 weight %, preferably 1~100 weight %, more preferably 2~100 weight %.

When the gelling agent is pectin, the preferred amount of native gellan gum relative to 100 weight % of pectin is generally 1~200 weight %, particularly 1~100 weight %.

When the gelling agent is gelatin, the preferred amount of native gellan gum relative to 100 weight % of gelatin is generally 0.1~200 weight %, preferably 1~100-weight %, more preferably 1~20 weight %.

This invention is further concerned with a method of inhibiting syneresis of gel compositions which comprises incorporating native gellan gum. This method is carried into practice by adding or formulating native gellan gum as one of the starting materials in the production of a gel composition. Therefore, from a different point of view, this method may be regarded as the above-mentioned method of producing a gel composition inhibited against syneresis.

The formulating amount of native gellan gum should vary according to the kind of gel composition, the kind of gelling agent used, and the water content of the composition but can be judiciously selected from the range of generally 0.1~200 weight %, preferably 1~100 weight %, more preferably 2~100 weight %, all based on 100 weight % of the gelling agent in the gel composition. The specific procedure is the same as that described hereinbefore.

(10) Foam Stabilizer

The invention relevant to this embodiment is based on the new finding that native gellan gum has the property to stabilize foams, particularly foams derived from proteins, and sustain them for a long time and provides the use of native gellan gum as a foam stabilizer, particularly a meringue stabilizer. Furthermore, the invention provides a method of stabilizing a meringue, meringues stabilized by the method, and chiffon cakes obtainable using said meringue.

Cakes and other products prepared by utilizing meringues have fluffy, soft mouth-feels originating from the characteristics of meringues. Moreover, the delicate fineness of a meringue is a determining factor in the delicately palatable texture of the cake. Therefore, the fluffy and delicate cellular structure of meringues is indispensable for the making of delicious cakes. However, meringues in general are ready to have the cellular structure liquidated and undergo syneresis, thus having the drawback of poor foam stability. Therefore, it has been essential to quickly submit the meringue to further processing, for example immediate baking or mixing with a cake batter and baking. It is for this reason that meringues are conventionally prepared in small batches. Moreover, in the production of chiffon cakes with high egg white contents, the loss of bulk after beating and/or the so-called kama-ochi (oven shrinkage) phenomenon in baking is liable to occur owing to the poor foam stability of the meringue. Therefore, to prevent the above phenomenon, it is generally unavoidable to incorporate an additional amount of solid matter (wheat flour etc.) with the result that it has been not easy to make soft, ready-to-melt, fluffy chiffon cakes.

This invention has solved this problem.

The foam stabilizer of this invention is a stabilizer which is capable of sustaining the delicate cellular structure of a meringue prepared by beating a formula containing egg white, optionally as well as sugar, very stiff and inhibiting the separation of water, which stabilizer is characterized by containing native gellan gum as an active ingredient.

This foam stabilizer, as far as it contains native gellan gum, is not particularly restricted in form or shape but is preferably an aqueous solution containing native gellan gum. This aqueous solution, as far as it contains native gellan gum dissolved therein, is not restricted in the method for preparation but is generally prepared by dispersing powdery native gellan gum in water and heating the dispersion up to 90° C. to dissolve the powder.

The amount of native gellan gum in the foam stabilizer is not particularly restricted as far as it can be admixed with egg white and other components when, for example, the foam stabilizer is an aqueous solution, and can be judiciously selected according to the amount of egg white and other components used in the preparation of a meringue. Thus, based on 100 weight % of water, native gellan gum is used in a proportion of preferably 0.01~2 weight %, more preferably 0.05~2 weight %. The foam stabilizer conforming to the above formulation and egg white are preferably used in a weight ratio of 1:4 through 1:1 (stabilizer:egg white).

The foam stabilizer of this invention should contain native gellan gum as an essential component and may further contain other components.

As said other components, a variety of additives in common use in foods and confections can be used as far as the stabilizing effect on the cellular structure of a meringue is not compromised, thus including but not limited to (1) gelatin, starch, modified starch, carrageenan, pectin (high-methoxy pectin, low-methoxy pectin), gums (locust bean gum, xanthan gum, guar gum, karaya gum, tragacanth gum, gum arabic) and (2) plant proteins or plant protein hydrolysates.

When used in combination with native gellan gum, the former components (1) stabilize the cellular structure of a meringue and improve its sustenance, while the latter components (2) enhance the beating effect (bulkiness) on egg white.

This invention is further directed to a meringue characterized by containing said foam stabilizer, that is to say native gellan gum.

The formulating amount of said foam stabilizer relative to egg white is preferably as mentioned above. Thus, when the foam stabilizer is an aqueous solution containing 0.01~2 weight %, preferably 0.05~2 weight %, of native gellan gum based on 100 weight % of water, the egg white foam stabilizer ratio is preferably within the range of 4:1~1:1 (by weight).

The meringue of this invention is not restricted by the method for preparation. The usual method comprises adding said foam stabilizer to egg white and beating them together or adding said foam stabilizer to beaten egg white and stirring the mixture or beating it again.

The meringue to which this invention is applicable is a meringue obtainable by beating egg white very stiff.

The egg white for use in this meringue is not limited to raw egg white but may be a processed egg white such as, for example, frozen egg white and egg white powder.

The meringue of this invention may be optionally supplemented with sugar. The sugar which can be used is not particularly restricted but can be judiciously selected according to the intended use of the meringue. Thus, for example, sucrose (powder sugar, granulated sugar, etc.), glucose, liquid sugar, starch syrup, and sugar alcohols can be mentioned and those sugars can be used each alone or in a combination of two or more species. The formulating amount of sugar, if used in the meringue, is not particularly restricted but can be judiciously selected according to the intended use of the meringue. The upper limit is generally about 60 weight % based on 100 weight % of the meringue containing the sugar.

This invention is further concerned with a method of producing a meringue having a stabilized cellular structure which comprises a step of beating egg white or mixing it with other components under stirring in the presence of said foam stabilizer.

This method is carried into practice by preparing a meringue in the presence of said foam stabilizer, that is to say native gellan gum. For example, in the process for meringue production, the beating of white egg or the mixing of a meringue with other components under stirring is carried out in the presence of native gellan gum.

The formulating amount of said foam stabilizer or native gellan gum based on egg white is as mentioned hereinbefore.

In accordance with this invention, as typically shown in Example (10-1), a meringue having a stable cellular structure showing no synthesis even after at least 48 hours can be produced, with the result that a finished meringue can be kept standing till use. Therefore, in the commercial production of meringues, the batch size can be increased to enhance the operation efficiency.

Furthermore, since stable meringues can be supplied as mentioned above, the phenomenon of "kamaochi (oven shrinkage)" can be obviated even when the solid contents of meringues are low so that very light and soft cakes, particularly chiffon cakes with further reduced solid contents can be manufactured.

This invention, therefore, is directed to cakes, particularly chiffon cakes, which are obtainable with said meringue.

The chiffon cake in the context of this invention includes all kinds of foods generally called chiffon cakes and is not restricted by raw materials or formulation. Preferred, however, are chiffon cakes such that, in the recipe or formulation of raw materials, wheat flour accounts for about 10~19 weight %, preferably about 14~19 weight %. Formerly, in order to maintain the light mouth-feel characteristic of chiffon cakes and yet avoid said kamaochi (oven shrinkage) phenomenon, it was necessary to formulate a solid component (wheat flour component) in a proportion of not less than 19 weight % based on the total formula but in accordance with this invention light, soft and yet form-retaining chiffon cakes can be provided even if the solid content (amount of wheat flour) is 19 weight % or less. However, cakes containing more than 19 weight % of wheat flour in terms of formulating amount are not excluded but fall within the scope of the invention.

(11) Palatability/Body-improving Agent

The invention relevant to this embodiment was developed on the basis of the finding that native gellan gum has the property to improve the intrinsic characteristics of various foods, improve their mouth-feels or impart new mouth-feels to foods. As such, this invention provides the use of native gellan gum as a palatability/body-improving agent.

The substrate food is not particularly restricted but includes the following, among others.

(a) Foods containing dairy materials and a gelling agent (b) Fried foods (c) Ice cakes (d) Hard candies (e) Noodles The application of native gellan gum to those foods and the consequent effects are now described.

(a) Foods Containing Dairy Materials and Gelling Agents

Foods containing dairy materials and gelling agents, particularly chilled desserts such as mousse, bavarois, puddings, jellies, etc. are required to have slick and smooth textures or mouth-feels.

Therefore, much research has been undertaken for the purpose of providing foods free from "roughness", uniform in composition, and delicate and fine in mouth-feel, and in order to prevent at least the phenomenon of "roughening", which detracts drastically from the palatability and body, a quenching step following pasteurization has been considered essential. However, this quenching step has the problem that it complicates the production process and increases the cost of production. Moreover, in (i) foods containing large amounts of calcium such as calcium-enriched foods, (ii) foods containing a black tea, coffee or other extract, (iii) cacao-containing foods, (iv) milled green tea-containing foods, and (v) foods containing a strawberry, orange, or other fruit juice, "roughening" takes place even if they are quenched so that it has been difficult to provide high-quality products.

Developed in this state of the art, this invention provides the use of native gellan gum as a palatability/body-improving agent for foods containing dairy materials and gelling agents, particularly a "roughening" inhibitor. This invention further provides a food containing dairy materials and gelling agents which is free from "roughness", uniform in composition and delicate and fine in texture and still further a method of producing said food.

When native gellan gum is incorporated in a food containing dairy materials and gelling agents in accordance with this invention, a highly marketable food article completely free from "roughness", uniform in composition, glossy, and delicate in mouth-feel can be consistently provided by spontaneous cooling instead of interposing a quenching step which has heretofore been considered essential in the production process.

Furthermore, this effect of formulation of native gellan gum is significantly expressed even in Ca-enriched foods, foods containing a black tea or other extract, cocoa, or milled green tea, and fruit juice-containing foods, the "roughening" of which has been hardly obviated by quenching.

Moreover, even in those kinds of foods containing dairy materials and gelling agents which have never presented with the "roughening" problem in the past, incorporation of native gellan gum results in a more uniform and stable dispersion of dairy and other materials to give a more delicate texture of improved palatability.

The "roughening" and "roughness" in the context of this invention mean the phenomenon that the homogeneity of a composition is impaired by coagulation of the protein derived form the dairy ingredients and the condition of such impaired homogeneity. Consequently, the "roughened" food shows a coarse texture apparently attributable to the coagulation, clouding and suspension of ingredients and gives a heterogeneous taste owing to sedimentation of the coagulated ingredients.

The food to which this invention is applicable is a food containing at least a diary component and a gelling component and is not particularly restricted as far as those components are contained.

The diary component that may be contained includes milk, soya milk, and processed matters derived therefrom. The processed matters may for example be condensed whole milk, condensed nonfat milk, powdered whole milk, and powdered nonfat milk, among others. Those may be contained each alone or in a combination of two or more species. When nonfat or skim milk is contained, oil components such as butter, raw cream, coconut oil, palm oil, etc. may be concomitantly contained. The proportion of the diary component is not particularly restricted but, in terms of nonfat milk solids, may range from 0.1~30 weight %, preferably 0.3~15%, more preferably 0.5~8 weight %, all based on 100 weight % of the food. In the case of puddings, the range of 3~8 weight % is particularly preferred.

The gelling component (agent) which can be used in this invention is not particularly restricted but includes various substances which are conventionally used in foods, that is to say the substances capable of converting a food from a liquid to a solid. Thus, it includes but is not limited to a variety of natural gums such as carrageenan, locust bean gum, xanthan gum, furcellaran, alginic acid, alginates, pectin, guar gum, gum arabic, gellan gum, pullulan, agar and gelatin. Those substances may be contained each independently or in a combination of two or more species.

The proportion of the gelling agent should be selected according to the kind of gelling agent and the kind of product food and cannot be defined in general terms. However, taking puddings as an example of product, the proportion of the gelling agent relative to 100 weight % of the food may for example be 0.05~4 weight %, preferably 0.1~2 weight %, more preferably 0.2~1.5 weight %.

The food to which this invention can be applied is a food available upon solidification of the main fraction composed of said diary materials with said gelling agent but is preferably a semi-solid food and more preferably a food required to have a more delicate, slick and smooth texture or eating quality. Among specific foods of this type are the so-called chilled desserts such as puddings, mousse, bavarois, jellies and annin-tofu. The still more preferred are puddings, particularly milk puddings.

The chilled desserts may each contain an extract of black tea, coffee or the like, any of such ingredients as cacao powder, milled green tea, etc., and/or strawberry, orange and other fruit juices or may have been artificially calcium-enriched. This invention is particularly useful for those foods, in which its inhibitory effect on "roughening" is prominently expressed.

The calcium-enriched food in the context of this invention is a food containing 0.09~3 weight %, preferably 0.09~1 weight %, more preferably 0.18~1 weight %, of calcium based on 100 weight % of the food.

The term food in the context of this invention covers not only processed foods such as those mentioned above but also a broad variety of food compositions used in the production of such processed foods. The food compositions mentioned above include but are not limited to compositions for the production of chilled desserts such as puddings, mousse, bavarois, jellies, annin-tofu, etc. and compositions for the production of tofu and related foods, and there is no particular limitation on their forms, namely powders, granules, fluids, etc.

This invention is concerned with foods containing said diary materials and gelling agents, characterized in that native gellan gum has been incorporated therein.

The most outstanding feature of this invention is that the above-mentioned effect of native gellan gum remains unaffected regardless of the cooling mode used in the production process. Thus, for the sole reason that native gellan gum is included in the batch formula, the food expressing the above-mentioned merits of the invention can be manufactured in a simplified production flow dispensing with the hitherto-essential quenching step and, hence, at reduced costs and with reproducible quality.

The formulating amount of native gellan gum in the food of this invention is dependent on the kind and constitution of food, and the kinds and amounts of dairy ingredients and gelling agent contained, among other factors, and cannot be stated in general terms. However, taking puddings as an example, the proportion of native gellan gum relative to 100 weight % of the product pudding may for example be generally 0.005~0.3 weight %, preferably 0.005~0.1 weight %, more preferably 0.01~0.05 weight %.

If the proportion of native gellan gum is too small, "roughening" will not be sufficiently inhibited. On the other hand, if the upper limit of 0.3 weight % is exceeded, a pasty mouth-feel with increased elasticity will result. However, when it is intended to enhance the gel strength of foods and impart an elastic mouth-feel, native gellan gum may be formulated in excess of the above range.

The food of this invention may contain, in addition to the above-mentioned components, the sugars, flavors, neutralizers, caramel, emulsifiers, sodium chloride, edible oil and fat, stabilizers, antioxidants, preservatives, colors, and acidulants which are broadly used in the food industry. Furthermore, the processed food products and food compositions according to this invention preferably have been adjusted to the pH range of pH 3~8, more preferably pH 4~8, most preferably pH 5~7.5.

This invention further provides a method of producing highly marketable foods which are uniform and steady in composition, pleasing to the eye, and delicate in mouth-feel without the incidence of "vroughening".

Here, the same food items as mentioned hereinbefore can be mentioned. Preferred, however, are chilled desserts such as puddings, bavarois, mousse, jellies, annin-tofu, etc., and those chilled desserts which required quenching for production because of the incidence of "roughening" in the past are particularly preferred.

The conventional protocol for the production of puddings, for instance, is as follows.
(i) Disperse and dissolve milk, dairy products, sugar, egg and a gelling agent, and add a flavor, color, etc. to prepare a food composition.
(ii) Homogenize (100~150 kg/cm$^2$)
(iii) Sterilize or pasteurize (100~150° C., several seconds).
(iv) Cool (60~70° C.)
(v) Fill into containers
(vi) Add a caramel sauce
(vii) Seal the cover material
(viii) Quench ($\leqq 10°$ C.)
(ix) Package Among those steps, the quenching step (viii) in particular is an indispensable step for the production of puddings free of "roughening". Moreover, since "roughening" is a very sensitive phenomenon which occurs or does not occur depending of the cooling rate, the cooling velocity is rigorously controlled.

On the other hand, the production method of this invention is characterized in that, in the course of production of a food product containing a dairy component and a gelling agent, a food composition containing said dairy component, gelling agent and native gellan gum is used as a pre-solidification composition for production of the food, and the final food product is manufactured by cooling the above composition for solidification. According to this method, a food product free from the "roughening" defect, delicate and fine in texture, and uniform in composition can be manufactured conveniently without resort to so rapid a cooling procedure. The cooling procedure according to this invention is by no means restricted by cooling conditions. For example, the cooling temperature may be the gelation temperature of the gelling agent used and the solidification time is not restricted, either. Therefore, any cooling method such as air cooling, spontaneous cooling, or water cooling can be liberally selected without limitation.

The cooling step (iv) in the above production flow is required partly for lowering the temperature of the system so that the system may be rapidly chilled in said step (viii). In this invention, this precooling step may be optionally omitted.

Thus, the production method of this invention does not call for critical temperature control except in the pasteurization or sterilization step and, therefore, is of great utility value in that high-quality foods free from said "roughening" defect can be produced expediently, at low cost, and with high reproducibility. Moreover, the production method of this invention can be regarded as a method of inhibiting the "roughening" of foods containing dairy components and gelling agents, such as puddings and bavarois.

The formulating amount of native gellan gum should be judiciously selected according to the variety of food to be produced, for instance, and cannot be stated in general terms, although the range defined above can be typically utilized.

(b) Fried Foods

Fried foods, particularly deep-fried foods, are required to quickly drain of frying oil, present with a least stodgy, crispy mouth-feel immediately after frying, and retain the crispy surface texture for several hours after cooking. Particularly in the commercial production of prepared-dishes for boxed luncheons and frozen foods, fried foods with the appetite-whetting bulk and retaining good palatability despite an elapse of time after frying or insuring a faithful reproduction of the initial palatability on reheating.

Developed in the above state of the art, this invention is directed to a fried food obtainable with a binding agent or a fry batter, which is characterized in that it contains native gellan gum as a palatability/body-improving agent.

The fried food according to this invention is characterized in that it has a good bulk, i.e. the high volume which is appetite-whetting, and a light, crispy mouth-feel, and further in that it drains quickly of the excess frying oil. When this agent is used as the binder for a roasted or baked food such as a hamburg steak, a delicious food retaining the internally sizzling quality with little absorption of excess frying oil can be obtained. Moreover, even if this fried food has been dehydrated after cooking, it reconstitutes itself quickly in hot water. When frozen, it does not: lose its satisfactory palatability. Therefore, this invention can be broadly applied to instant foods such as frozen foods and dehydrated foods.

The "fried food" in the context of this invention means any food that is cooked by heating with oil, particularly a food obtainable by heating a food material in high-temperature oil, generally at about 120~200° C. or a processed food containing such a food as an ingredient. Therefore, the "fried food" according to this invention includes not only deep-fried foods cooked by immersing food materials in large quantities of hot oil but also foods prepared by frying or roasting with small amounts of oil.

The "deep-fried food" can be roughly classified into su-age (bare-fried food) and koromo-age (coat-fried food). The su-age is a food fried in the uncoated condition. The koromo-age is a food fried after coating with wheat flour, starch or the like. According to another classification, a food fried (koromo-age) with a low-water-content coat, inclusive of kara-age, and a food fried with a high-water-content coat, e.g. tempura, shozin-age, fritter, etc., can be mentioned. The panko-age, a food coated with wheat flour, stirred egg and bread crumbs and, then, fried, is intermediate between the above two foods.

The fried food according to this invention includes any and all foods cooked with a binding agent or fry batter either comprising or containing native gellan gum, regardless of whether it has experienced heating previously or not.

Among fried foods, Hamburg steaks and tsumire (milled fish flesh supplemented with a binder such as egg and starch and boiled in water) are prepared by adding native gellan gum as a binding agent to raw materials and cooking. In the case of croquette, native gellan gum may be used as a binder or be formulated into a fry batter containing soft flour or the like for cooking. Furthermore, in the case of deep-fried foods, this gum may be formulated into a fry batter based on soft flour or katakuri-ko (starch obtained from roots of *Erythronium japonicum*) and particularly in the case of kara-age (uncoated fry), the food surface can be grazed with a solution of native gellan gum within a certain concentration range before cooking. Thus, dices or strips of a vegetable (potato, edible burdock, carrot, etc.) can be bound, several per bundle, and fried without a thick coat.

Insofar as the effect of this invention can be expressed, the binding agent or the fry batter may contain, in addition to native gellan gum, various other polysaccharides such as tamarind seed gum, xanthan gum, guar gum, locust bean gum, pullulan, soybean polysaccharide, karaya gum, tragacanth gum, and gum arabic.

The optimum amount and use concentration of native gellan gum for the preparation of the fried food according to this invention are dependent on the kind and size of food material and the mode of use, for example as a binder or a component of a fry batter, and can be judiciously selected and adjusted by one skilled in the art. Generally speaking, the concentration should be such that food ingredients may be held in a three-dimensional form or be bound to each other and dispersed well as a unit. The preferred proportion is 0.08~2 weight % based on water and to insure the ease with which food ingredients may be coated, the preferred range is 0.5~1.5 weight %.

It is sufficient that the concentration of native gellan gum be as defined above just before cooking and, moreover, the gum need not necessarily have been dissolved but only need be in swollen state.

Among the conditions of heat-cooking for the fried food of this invention, the oil temperature is not particularly restricted but can be selected and adjusted by one skilled in the art according to the kind and size of food material and the objective mouth-feel. Generally, a temperature between 120° C. and 180° C. is preferred and from the standpoint of improved oil drainage and increased crispness, the range of 140~180° C. is preferred. The heating time is not particularly restricted, either, but can be judiciously selected and adjusted by one skilled in the art. Generally, in the case of deep-fried food, a heating time of 30~180 seconds is preferred, and from the standpoint of good oil drainage and increased crispness, the range of 60~120 seconds is preferred.

(c) Ice Cakes

Ice cakes inclusive of ice flakes or shavings and ice sticks (sherbet-on-a bar) are required to have a crispy mouth-feel, ease of ingestion, and the ease of piercing with a spoon despite the frozen state. In addition, there has been the problem that, while eating, a concentrated syrup is pooled in the bottom layer, with the upper layer getting watery.

Developed in view of the above situation, this invention is concerned with an ice cake containing native gellan gum as a palatability/body-improving agent.

The ice cake of the invention, thanks to inclusion of native gellan gum, is characterized in that, unlike the conventional product which, on melting of ice, gives a watery top layer with the syrup concentrated and pooled in the bottom layer, its formulated composition is consistently maintained with little change in the distribution of ingredients. Furthermore, even in frozen condition, a spoon may easily pierce through the body of the food and the food presents with a crispy mouth-feel characteristic of, for example, freshly shaved ice.

The ice cake in the context of this invention means any and all foods that comprise or contain frozen water and specifically includes but is not limited to ice shavings, sherbet-on-a-bar, and crushed ice.

The formulating amount of native gellan gum, relative to 100 weight % of the ice product, is 0.01~0.2 weight %, preferably 0.02~0.1 weight %. When the level of addition is below 0.01 weight %, the above-mentioned effects of constancy in composition even on melting, ease of piercing the body of ice with a spoon and crispy mouth-feel are somewhat sacrificed. On the other hand, if the upper limit of 0.2 weight % is exceeded, the premature gelation of the native gellan gum composition prior to addition will interfere with operation, thus presenting a production problem. However, the above upper limit is imposed in consideration of workability only and if this problem can be solved, the above range need not be strictly adhered to.

The method of producing an ice cake according to this invention is not restricted as far as native gellan gum can be formulated as a component of the ice cake but the conventional technology can be generally used. An ordinary procedure comprises adding native gellan gum to a syrup to be applied to ice shavings or flakes, mixing the syrup with ice flakes, and freezing the mixture.

(d) Hard Candies

Regarding hard candies, the conventional products have the drawback that a great force is required for biting at first or while they can be bitten rather easily at first, the resistance is soon lost to cause dissatisfaction. Therefore, the so-called gummy candies which feature a sustained good biting quality are widely accepted by the consumer. Under the circumstances, the development of hard candies having a crispy mouth-feel and not requiring an extraordinary biting force but maintaining a sustained good biting quality has been demanded in earnest.

Developed in view of the above situation, this invention provides a hard candy containing native gellan gum as a palatability/body-improving agent.

This invention further provides the use of native gellan gum as a crispness-imparting agent for hard candies.

The hard candy of this invention, which contains native gellan gum, can be bitten without requiring an extraordinary biting force and features a sustained crispy mouth-feel with adequate biting resistance. Stated differently, this is a candy which can be bitten with enjoyment, not to speak of the pleasure of licking.

The hard candy in the context of this invention means any hard candy that has been boiled down to the degree of "hard crack" and is not particularly restricted by its form and kind.

The formulating amount of native gellan gum relative to 100 weight % of the candy is 0.01~2 weight %, preferably 0.05~0.3 weight %. When the proportion of native gellan gum is smaller than 0.01 weight %, the above-mentioned effect of supple mouth-feel and crispy biting quality is somewhat sacrificed. When 2 weight % is exceeded, the premature gelation of the native gellan gum composition itself interferes with operation and presents a production problem just as pointed out hereinbefore for sherbets. Therefore, here again the upper limit is imposed from workability points of view and as far as this problem can be solved, the above-mentioned range need not be strictly adhered to.

The hard candy of this invention is manufactured by including native gellan gum in the batch formula in otherwise the same manner as in the conventional production process. Thus, there is no particular limitation on the method of production.

Furthermore, insofar as native gellan gum is contained, the candy of this invention may further contain other components in addition to the basic formula.

(e) Noodles

Noodles such as udon (Japanese style noodles), chuka-men (Chinese noodles) and pasta are generally better accepted when they have firm bodies. On the other hand, dehydrated noodles and the like are required to have the conflicting property, namely the ease of reconstitution.

Developed in view of the foregoing, this invention provides a noodle containing native gellan gum as a palatability/body-improving agent.

The invention further provides the use of native gellan gum as a body-imparting agent for noodles.

Because it contains native gellan gum, the noodle of this invention is characterized by full-bodied, adequate biting resistance qualities and, in the case of the dehydrated noodle, is characterized by rapid reconstitution in water or hot water in addition to the above qualities.

Here, the noodle includes a broad variety of noodles and equivalents such as chuka-men, udon, kishimen (ribbon-shaped shaped Japanese style noodle), pasta (spaghetti, macaroni, etc.) and soba (buckwheat noodle), regardless of whether they are raw, semi-raw, dehydrated, or LL (long life).

The formulating amount of native gellan gum can be judiciously selected from the range of 0.01~0.1 weight % based on 100 weight % of the wheat, buckwheat or other flour used. When the proportion of native gellan gum is smaller than 0.01 weight %, the above-mentioned effect of firm body and good biting quality is somewhat sacrificed. On the other hand, when 0.1 weight % is exceeded, the product assumes a taste or texture dissimilar to that of ordinary noodles. Therefore, if there is no objection to the palatability of ordinary noodles or equivalents, the above-mentioned range need not be considered to be a hard-and-fast rule. Thus, the proportion may be increased or decreased to suit one's taste.

The noodle of this invention is manufactured by adding native gellan gum to the usual formulation for noodles and there is no particular limitation on 'the method of manufacture.

EXAMPLES

The following examples pertaining to the above embodiments (1) ~(11) are intended to illustrate the present invention in further detail and should by no means be construed as defining the scope of the invention.

Example 1

Freeze-thaw Resistant Jellies

Example (1-1)

To 80 weight % of water were added 1 wt. % of native gellan gum, 12 wt. % of sugar and 0.2 wt. % of citric acid, and the mixture was stirred for dissolving at 80° C. for 10 minutes and made up with water to a total of 100 weight %. This mixture was poured into a container and cooled to 10° C. to provide a jelly.

This jelly was frozen once in the freezer at −18° C. overnight and, then, allowed to stand for thawing at room temperature. This procedure was repeated 10 times but the jelly showed no change in strength or palatability and substantially no separation of water was observed, either.

Comparative Example (1-1)

Using 0.5 wt. % of gellan gum and 0.3 wt. % of calcium lactate in lieu of native gellan gum, the procedure of Example (1-1) was otherwise repeated to provide a jelly. When this jelly was subjected to one freeze-thaw cycle, a large quantity of water amounting to more than one-third of the total weight separated out and the texture of the jelly was disrupted so extensively that it was ready to collapse. Moreover, a marked degradation of eating quality was observed.

Comparative Example (1-2)

Using 1 wt. % of kappa-carrageenan in lieu of native gellan gum, the procedure of Example (1-1) was otherwise repeated to provide a jelly. When this jelly was subjected to one freeze-thaw cycle, a large quantity of water amounting to more than one-quarter of the total weight separated out and the texture of the jelly was disrupted so extensively that it was ready to collapse. Moreover, a marked degradation of eating quality was observed.

Example 2

Dehydrated Gels

Example (2-1)

To 80 wt. % of water were added 1 wt. % of native gellan gum, 12 wt. % of sorbitol and 0.2 wt. % of citric acid, and the mixture was stirred for dissolving at 80° C. for 10 minutes and made up with water to a total of 100 weight %. This mixture was poured into a vessel and cooled to 10° C., whereupon a gel was obtained. This gel was dried in a hot-air dryer to provide a dehydrated gel which weighed 20% of the pre-dehydration weight.

This gel was placed in a vessel and water was added, whereupon the gel regained the pre-dehydration size, form, strength, and mouth-feel in 5 minutes.

Example (2-2)

To 80 wt. % of water was added 1 wt. % of native gellan gum, and the mixture was stirred for dissolving at 80° C. for 10 minutes and made up with water to 100 weight %. This solution was poured into a vessel and cooled to 10° C. whereupon gel balls with a diameter of 10 mm were obtained. The gel balls were dried in a hot-air dryer to provide dehydrated gel balls which weighed 2% of the pre-dehydration weight.

The above gel balls were placed in a cup and shiruko (a sweetened adzuki bean soup) prewarmed to 70° C. was poured over the balls. As a result, the gel balls regained their pre-dehydration size, form, strength and mouth-feel in 5 minutes so that they could be ingested as a savory substitute for shiratama (white glutinous rice balls).

Comparative Example (2-1)

Using 0.5 wt. % of gellan gum and 0.3 wt. % of calcium lactate in lieu of native gellan gum, the procedure of Example (2-2) was otherwise repeated to prepare a gel. When this gel was dehydrated and placed in water, it failed to reconstitute itself even after 30 minutes, and the disrupted, hard texture indicated degradation.

Example (2-3)

To 80 wt. % of water was added 2 wt. % of native gellan gum, and the mixture was stirred for dissolving at 80° C. for 10 minutes and made up with water to a total of 100 weight %. This solution was poured into a rice-grain mould and cooled to 10° C. to prepare gel grains simulating rice grains. The gel grains were dried in a hot-air dryer to provide dehydrated gel grains which weighed 3% of the pre-dehydration weight.

The above gel grains were placed in rice bowl and a suitable amount of green tea extract prewarmed to 80° C. and wasabi (horseradish) flavor were added. As a result, the gel regained the pre-dehydration size and mouth-feel so that the food could be ingested as a substantially calorie-free substitute for wasabi chalzuke (horseradish-spiced boiled rice in green tea).

Example 3

Rice Cake-like Gels

Example (3-1)

Preparation of a Canned Shiratama Zenzai

To 68 wt. % of water were added 30 wt. % of shiratamako (glutinous rice flour) and 2 wt. % of native gellan gum, and the mixture was evenly kneaded and molded into a couple of shiratama balls 2 cm in diameter each. The shiratama balls and 66 g of a mixture of commercial boiled adzuki-beans (raw materials: sugar, adzuki-beans, starch, NaCl) (manufacturer: Imuraya Seika K.K.) (62 wt. %) and water (32 wt. %) were placed in a cylindrical can 6 cm in diameter and 2.5 cm high, followed by sealing. This sealed cylindrical can was subjected to retort treatment at 121° C. for 20 minutes to provide a canned shiratama zenzai (a thick adzuki-bean soup containing shiratama as a solid ingredient).

Despite the retort sterilization, the shiratama balls in the product had not dissolved out or become macerated but remained to be fully satisfactory in appearance, resembling rice balls in mouth-feel as well. Moreover, when ingested one week after production, the shiratama balls were found to fully retain the rice cake-like viscoelasticity without hardening with time.

Comparative Example (3-1)

Except that shiratama balls were prepared according to the following recipe, the procedure of Example (3-1) was otherwise repeated to provide a canned shiratama zenzai [comparative product (3-1)].

* Recipe for shiratama: To 45 wt. % of water was added 55 wt. % of siratama-ko (a kind of glutinous rice flour), and the mixture was evenly kneaded and molded into two shiratama balls 2 cm in diameter each.

This comparative product (3-1) began to harden due to aging only after 1 day of storage in the refrigerator and, because of the hardened core, was not easy to ingest. After 2 days of storage, it was still harder and unsuited for eating.

Example (3-2)

Preparation of Yakimochi (Baked Rice Cake)

To 68 wt. % of water were added 30 wt. % of mochiko (a kind of glutinous rice flour), and 2 wt. % of native gellan gum, and the mixture was evenly kneaded and molded into a rice cake measuring 2 cm square×1 cm in thickness and weighing about 6 g. This rice cake was steamed in a steamer and using a portable burner, its surface was scorched to provide the objective yakimochi (baked rice cake).

This baked rice cake showed no hardening due to aging even when stored in the refrigerator for 1 week but fully retained the viscoelastic mouth-feel of the freshly baked rice cake. When the baked rice cake prepared as above was heated in an electronic range, wrapped around with a wafer of seasoned layer, dipped in sugar-soy, and ingested, the mouth was immediately filled with the savory aroma of baked rice cakes and the palatability characteristic of baked rice cakes could be enjoyed. On the other hand, when a baked rice cake prepared in the same manner and a shiruko soup (adzuki-bean soup) separately prepared were filled into a can, subjected to retort treatment, and chilled in the refrigerator, a cold shiruko was obtained. Despite its coldness, the rice cake was soft and delicious.

Example (3-3)

Preparation of Rice Cakes with a rice Cake-making Machine

First, 490 wt. % of water and 10 wt. % of native gellan gum were heated together at 90° C. under agitation with a stirring machine (Shinto Kagaku, Type 3000H) for 10 minutes to prepare a native gellan gum solution. This solution was incubated at about 90° C. Separately, 500 wt. % of glutinous rice rinsed with water was set in the rice cake-making machine AFC-166 (manufactured by Toshiba), in which it was steamed for about 30 minutes and pounded for 10 minutes. Then, 500 wt. % of the above-prepared native gellan gum solution was added and the mixture was further pounded with the rice cake-making machine for another 10 minutes to provide a rice cake.

The above rice cake was packed into a cylindrical can 6 cm in diameter and 4 cm deep up to its capacity of about 95 g, followed by sealing, and stored in the refrigerator for 30 days. As a result, no hardening due to aging was noted and the rice cake retained the initial viscoelastic consistency.

The rice cake prepared as above (about 100 g) and water (about 100 g) were packed into a 500 g retort pouch under vacuum and this vacuum-packed pouch was subjected to retort treatment at 121° C. for 20 minutes. As a result, the rice cake did not dissolve out or become macerated. When this same rice cake was stored in the refrigerator for 1 week, it showed no hardening due to aging but retained the satisfactory viscoelasticity which is characteristic of the genuine rice cake.

Example 4

Copy Foods

Example (4-1)

Abalone-like Rood-1

A mixture of 6 wt. % of water and 1 wt. % of native gellan gum was filled into a degassed 30 mm-dia. polyvinyl chloride casing up to a length of 100 mm and heated at 85° C. for 20 minutes to provide a low-calorie food tasting like abalone. This food was sliced to 2 mm thickness and added to a salad to prepare a sea-food salad. This food had exactly the same biting resistance as that of an abalone and when dressed with a shellfish-flavored dressing and ingested, the food was felt as if it were a true abalone.

Example (4-2)

Abalone-like Food-2

Using a roller, a mixture of 7 wt. % of water, 1 wt. % of native gellan gum, and 0.1 weight %; of abalone flavor was rolled to a thickness of 3 mm and cut. The resulting sheet, 100 mm×100 mm×3 mm, was vacuum-packed and subjected to retort treatment at 121° C. for 20 minutes to provide a food sheet. This food sheet was sandwiched to provide an abalone sandwich. Even in the form of a sandwich, the palatability of abalone was prominent and the unique biting quality different from that of hams, cheese, etc. could be enjoyed in eating.

Example (4-3)

Sakuramochi-like Dessert (1) Preparation of the Bottom Layer Jelly

To 30 wt. % of water was added 30 wt. % of nama-an (paste of cooked beans), followed by addition of 0.5 wt. % of native gellan gum and 30 wt. % of granulated sugar. The mixture was stirred at 80° C. for 10 minutes and 0.1 wt. % of flavor was added. The whole mixture was made up with water to 100 weight % and a portion of it was filled into a vessel and cooled in the refrigerator to provide a bottom layer jelly.

(2) Top Jelly

To 70 wt. % of water were added 1 wt. % of native gellan gum and 20 wt. % of granulated sugar, and the mixture was stirred at 80° C. for 10 minutes. Then, 0.05 wt. % of flavor and 0.02 wt. % of color were added and the whole mixture was made up to 100 wt. % with water to provide a top jelly.

(3) Sakuramochi-like Dessert

A cherry leaf was placed on the bottom layer jelly prepared in (1) and the top jelly was dispensed on top of the leaf. After the obtained jelly was placed in a vessel and the vessel was sealed, the assembly was subjected to retort sterilization at 121° C. for 20 minutes and cooled to provide a sakuramochi-like dessert.

Example (4-4)

Kuzukiri-like Dessert (1) Preparation of a Syrup

To 70 wt. % of water was added 10 wt. % of reducing maltose syrup, followed by addition of 0.8 wt. % of gum arabic, 0.085 wt. % of pullulan and 15 wt. % of granulated sugar. The mixture was stirred for dissolving and 0.3 wt. % of calcium lactate, 0.35 wt. % of citric acid (crystals), 0.2 wt. % of trisodium citrate and 0.1 wt. % of flavor were added. The whole mixture was made up with water to 100 wt. % to provide a syrup.

(2) Preparation of a Kuzukiri-like Dessert

To 70 wt. % of water was added 10 wt. % of reducing maltose syrup, followed by addition of 15 wt. % of granulated sugar, 0.7 wt. % of native gellan gum, 0.2 wt. % of gellan gum and 0.12 wt. % of trisodium citrate. The mixture was stirred for dissolving at 85° C. for 10 minutes, after which 0.3 wt. % of calcium lactate and 0.1 wt. % of flavor were added. The whole mixture was made up with water to 100 wt. % and cooled in the refrigerator. The product was cut into ribbons and placed together with the syrup in a container. After sealing of the container and pasteurization at 85° C. for 30 minutes, the product was cooled in the refrigerator to provide a kuzukiri-like dessert.

Example (4-5)

Copy Squid

Native gellan gum, 3 wt. %, was placed in water and dissolved by stirring at 90 for 10 minutes. The solution was poured into a vessel, 50 mm×200 mm×6 mm high, and cooled to 20° C. to provide a copy squid. This copy squid was translucent and white and had a plump feel closely resembling a genuine squid in appearance and mouth-feel. This copy squid was cut into filaments 50 mm long and 5 mm wide to prepare ikasomen (squid fine noodles). When this ikasomen was dipped in a soy containing grated horseradish dissolved therein and ingested, it resembled a genuine squid so closely in both appearance and palatability that the two could not be easily discriminated. Since it is a non-calorie, non-cholesterol food, this copy squid can be ingested with gusto and without care about calorie intake and cholesterol level.

Example (4-6)

Copy Bait

Native gellan gum, 4 wt. %, was placed in water and dissolved by stirring at 90° C. for 20 minutes. The solution was poured into an "earthworm" mold comprising a metal cylinder measuring 10 mm in diameter and 110 mm long and rounded at either end, which had been preheated to 90° C., and was then allowed to cool to provide a copy bait simulating an earthworm. This copy bait is not hazardous to fish and fowls, if ingested, and will be readily biodegraded in the sea, for instance. Therefore, fishing can be enjoyed without the risk for adverse effects on ecology.

Example 5

Cooling Agent

Example (5-1)

To 196 g of water was added 4 g (2%) of native gellan gum, and mixture was stirred for dissolving at 85° C. for 5 minutes. This solution was poured into a vessel 85 mm in diameter to a height of 17 mm and left standing at room temperature to provide a cold retention gel composition for use as a cooling agent.

Figure 2:
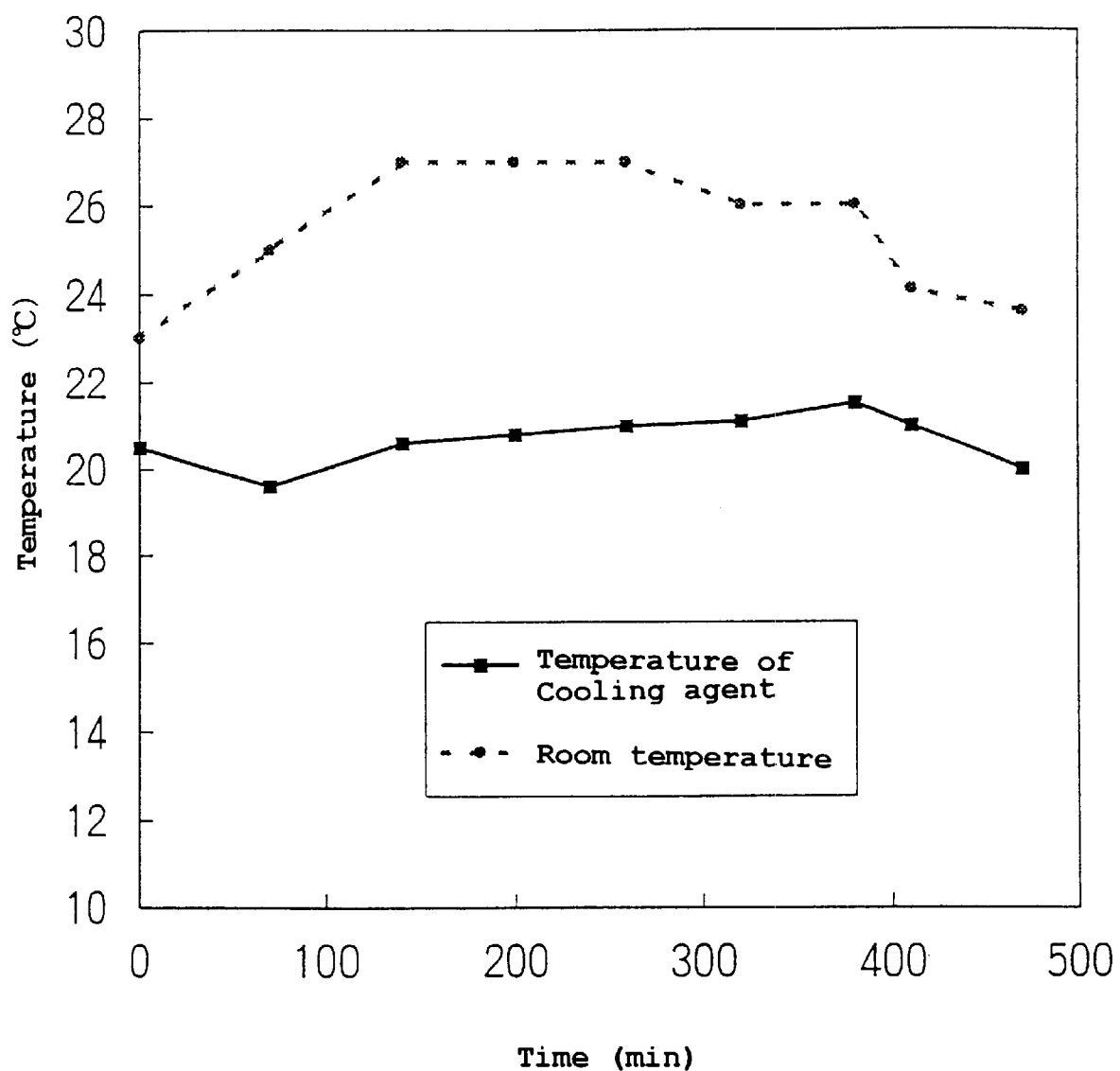
FIG. 2 is a diagram showing the time-course of the relation between the temperature of a cold-retaining agent of the invention as prepared in Example (5-1) and room temperature (external temperature).

A temperature probe was inserted into the center of this cooling agent and the temperature was serially measured and compared with the ambient; atmospheric temperature. The data are shown in FIG. 2. It was found from the data that the cooling agent of this invention consistently shows temperatures lower than atmospheric temperature by 4~6° C. at all times.

Example (5-2)

To 156 g of water was added 4 g of native gellan gum, and the mixture was stirred for dissolving at 85° C. for 5 minutes.
(A) Then, 40 g of propylene glycol was added to 160 g of the above solution and the mixture was stirred or
(B) 40 g of water in lieu of propylene glycol was added to 160 g of the above solution and the mixture was stirred. Each mixture was poured into a vessel 85 mm in diameter to a height of 6 mm and while it was held stationary in a horizontal position, dried at 50° C. for 6.5 hours to provide a compact cooling agent.

Figure 3:
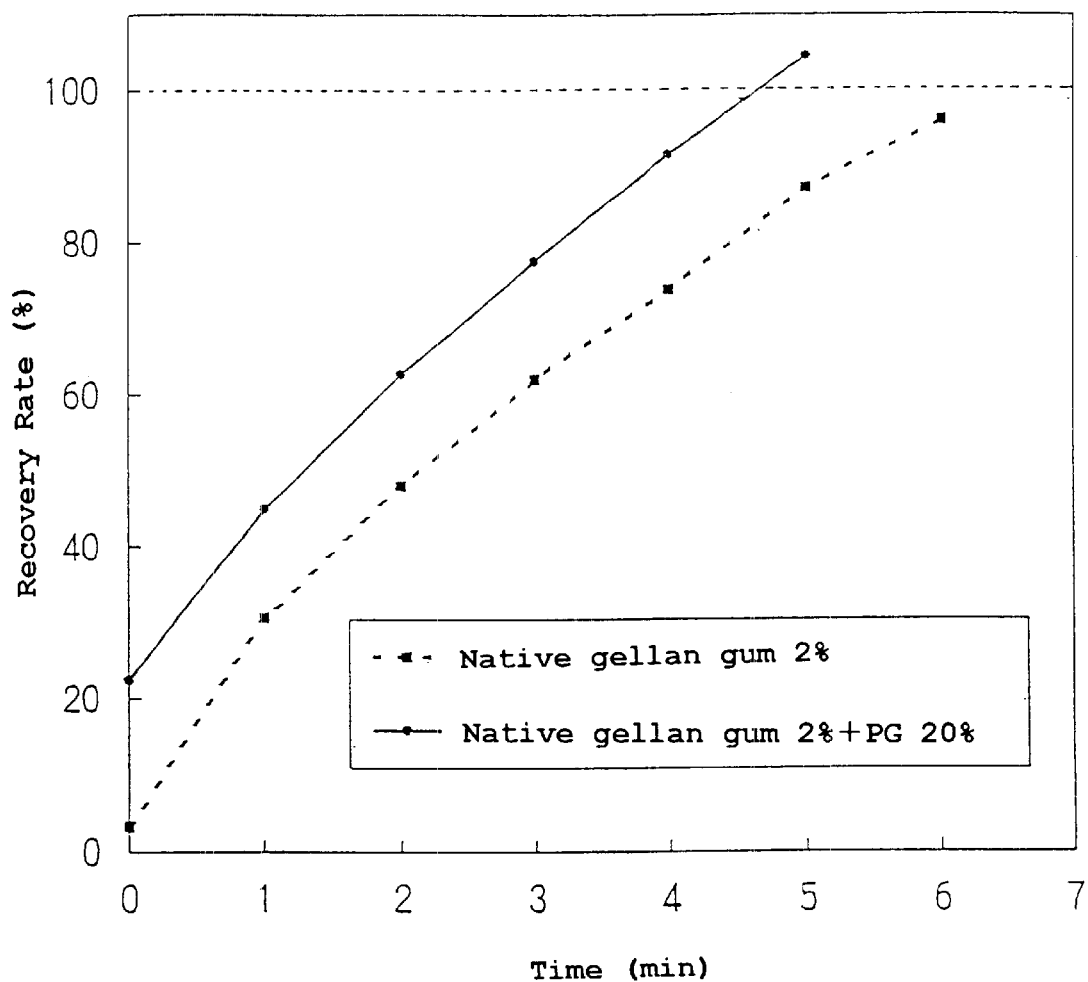
FIG. 3 is a diagram showing the relative time course of the recovery on reimmersion in water to pre-drying condition of the dehydrated compositions obtained by drying a cold retention composition comprising native gellan gum and water and a cold retention composition comprising native gellan gum, water and polyethylene glycol (PG), respectively [Example (5-2)].

As a result, A was reduced in weight to 19.4% of the pre-dehydration weight and B to 1.2% of the pre-dehydration weight. Substantially no change was found in diameter. The height of A decreased to 1.16 mm and that of B to 0.07 mm. A was highly flexible, showed good shape-retaining properties, and even in this condition, expressed a cooling effect. B was not as flexible as A but could be folded. Then, A and B were immersed in tap water (23° C.) to check for the rate of reconstitution. As shown in FIG. 3, a complete recovery to the pre-dehydration weight occurred in 4~6 minutes. The reconstituted cooling agents were both as effective as the cooling agents prior to dehydration.

Example (5-3)

To 312 g of water was added 8 g of native gellan gum, and the mixture was stirred for dissolving at 85° C. for 5 minutes. To this solution, 320 g, was added 80 g of propylene glycol, and the mixture was stirred to prepare a cold retention gel composition. This gel composition was placed in a polyvinyl chloride pouch and the opening was sealed by fusion to provide a cooling agent. This cooling agent was frozen in the freezer at −20° C. for 6 hours and then placed in a polystyrene foam box 150 mm×230 mm×150 mm. The box was covered and, after an elapse of 2 hours, the internal temperature of the box was measured and found to be 8° C. The cooling agent was then taken out, thawed in tap water, refrozen under the same conditions as above, and after an elapse of 2 hours the internal temperature was measured in the same manner as above. This procedure was repeated 10 times during a total of 20 days but no change whatever was found in the cooling efficiency of the cooling agent. The elasticity and tactile quality of the gel taken out from the pouch were also compared with those of a control sample which had not undergone the above treatment but no difference at all was found.

Example (5-4)

To 156 g of water was added 4 g of native gellan gum, and the mixture was stirred for dissolving at 85° C. for 5 minutes. Then, 40 g of propylene glycol and 0.01 g of 1-menthol were added to the solution prepared above (160 g), followed by stirring, and the mixture was poured into vessels, 30 mm×80 mm each, up to a height of 3 mm and cooled at 5° C. for 2 hours to provide cooling sheets.

Ten monitors were urged to lie in supine position with the cooling agent placed on the forehead for 2 hours. As a result, no residues remained on the forehead after removal of the agent at the end of the 2-hour trial session and all the 10 monitors reported that they consistently felt cool and comfortable during use.

Moreover, neither a complaint of sticky skin nor skin rash was found.

Example 6

Dispersion Stabilizer

Examples (6-1) ~(6-4), Comparative Examples (6-1) ~(6-3)

Cocoa Drink Composition

The cocoa compositions shown in Table 2 were prepared and each was dispersed in sufficient water to make 100 weight %. This dispersion was stirred with Homomixer at an elevated temperature of 70° C. This mixture was homogenized using a homogenizer at a primary pressure of 150 kg/cm$^2$ and a secondary pressure of 50 kg/cm$^2$ and the resulting homogenate was filled into a glass vessel (35 mm in diameter and 130 mm high), which was then stoppered, and sterilized by autoclaving at 120% for 20 minutes to provide a cocoa drink. The cocoa drinks prepared in the above manner were stored in the incubator at 5° C. and 35° C. and the pattern of precipitation of cacao powders were serially monitored. The microcrystalline cellulose as a component of the dispersant was Ceollus (trademark) SC-42.

The results inclusive of those of the sensory evaluation are presented in Table 2.

TABLE 2

| | | Example 6 | | | | Comparative Example 6 | | |
|---|---|---|---|---|---|---|---|---|
| | | 1 | 2 | 3 | 4 | 1 | 2 | 3 |
| Formula | Cacao powder | 1 | 0.5 | 3 | 1 | 1 | 1 | 1 |
| | Sugar | 5 | 5 | 5 | 5 | 5 | 5 | 5 |
| | Milk | 10 | 10 | 10 | 10 | 10 | 10 | 10 |
| | Sucrose fatty acid ester HLB16 Dispersant | 0.05 | 0.05 | 0.05 | 0.05 | 0.05 | 0.05 | 0.05 |
| | Native gellan gum | 0.06 | 0.06 | 0.06 | 0.03 | | | |
| | Microcrystalline cellulose (SC-42) | | | | 0.3 | | | |
| | Gellan gum | | | | | 0.06 | | |
| | Carrageenan | | | | | | 0.1 | |
| | Locust bean gum | | | | | | | 0.2 |
| dispersion stability | 4° C. After 1 month' standing After 3 months' standing 35° C. After 1 month' standing After 3 months' standing | No precipitation occurred under any storage conditions, indicating good dispersibility. | | | | Precipitation invariably occurred within 1 month. | | |

TABLE 2-continued

|  | Example 6 | | | | Comparative Example 6 | | |
| --- | --- | --- | --- | --- | --- | --- | --- |
|  | 1 | 2 | 3 | 4 | 1 | 2 | 3 |
| Sensory evaluation | Delicious cocoa drinks with a full-bodied flavor and no gritty mouth-feel. | | | | 1: No bodied flavor 2: Highly viscous and even threading 3: More highly viscous, even stuck to the throat and swallowable only with resistance. | | |

The results presented in Table 2 indicate that the cocoa drinks according to Examples were invariably acceptable in appearance, taste, flavor and body, showing no sediments of cacao particles. Thus, all were delicious cocoa drinks reflecting well-stabilized dispersions which had never been achieved in the past. In contrast, the cocoa drinks according to Comparative Examples (6-1) ~(6-3) formed sediments and were not palatable because of insufficient body and trailing viscous after-taste.

Example (6-5)

Shiruko Drink

To 25 wt. % of adzuki-bean fragments soaked in 50 wt. % of water were added 30 wt. % of aka-koshian (red-colored bean jam prepared from the cellular fraction of beans), 8.5 parts of sugar, 0.05 wt. % of native gellan gum, and 0.2 wt. % of microcrystalline cellulose Ceollus (trademark) SC-42, and the mixture was boiled to a total of 100 weight % and placed in a vessel. The filled vessel was covered and subjected to retort sterilization at 121° C. for 30 minutes to provide a shiruko drink. This shiruko drink formed no sediments even when left standing at room temperature for 4 weeks. Thus, the adzuki-bean fragments and other insoluble matter had been uniformly dispersed in the liquid phase.

Example (6-6)

Orange Juice Drink

To 69 wt. % of water were added 20 wt. % of high fructose corn syrup, 0.03 wt. % of trisodium citrate and 0.03 wt. % of native gellan gum, and the mixture was stirred for dissolving at 50° C. for 15 minutes. Then, 10 wt. % of concentrated (⅕) orange juice, 0.3 wt. % of orange flavor, and 0.3 wt. % of citric acid (crystals) were added to the above solution and the mixture was bottled and homogenized with a homogenizer (pressure 50 kg/cm) to provide a 50% orange juice drink. When this drink was left standing for 2 months, no sedimentation of orange pulp or other solid matter was found, indicating that the dispersion of pulp was well stabilized.

Example (6-7)

Chocolate Drink

First, 10 wt. % of comminuted granulated sugar, 2 wt. % of cacao powder and 0.02 wt. % of native gellan gum were blended in powdery form to provide a instant chocolate dry powder. To this powder was added 100 wt. % of milk, and the mixture was stirred for 30 seconds to prepare a chocolate drink. A control chocolate drink was prepared without addition of native gellan gum under otherwise the same conditions.

Whereas the chocolate drink not containing native gellan gum formed a sediment in tens of seconds, the chocolate drink containing native gellan gum showed no sedimentation even after 2 hours of standing.

Example (6-8)

Calcium-enriched Milk Drink 0.03 g of native gellan gum and 0.3 g of microcrystalline cellulose Ceollus (trademark) SC-42 were dispersed in sufficient water to make 11 wt. % and the dispersion was stirred for dissolving at 90° C. for 15 minutes. To 20 wt. % of this solution were added 20 wt. % of water, 40 wt. % of a milk fraction containing 10% nonfat solid and 0.48 wt. % of calcium carbonate, and the mixture was homogenized with a homogenizer (pressure 150 kg/m$^2$) to provide a calcium-enriched milk drink.

As a control, a calcium-enriched milk drink was prepared without addition of native gellan gum and microcrystalline cellulose under otherwise the same conditions. The milk drinks were stored in the refrigerator and monitored for the time course of change. As a result, whereas the control drink prepared without addition of native gellan gum and cellulose formed a deposit of calcium in 5 minutes, the drink prepared with addition of native gellan gum etc. showed no calcium precipitation at all even after 4 weeks. Moreover, the flavor and taste of the test drink was as satisfactory as the control drink.

Example (6-9)

Dressing

To 52.1 wt. % of water were added 3 wt. % of sugar, 2 wt. % of salt, 5 wt. % of soy sauce, and 0.07 wt. % of native gellan gum, and the mixture was stirred for dissolving at 90° C. for 10 minutes. Then, 5 wt. % of fermentation process vinegar, 5 wt. % of apple vinegar, 5 wt. % of lemon vinegar and 22.5 wt. % of corn salad oil were added to the above solution. The resultant dressing was a stable suspension without a tendency toward separation into oil and aqueous phases and could be used without swirling the bottle beforehand.

Example (6-10)

Adzuki-bean Candy

To 47.7 wt. % of water were added 6 wt. % of 75% starch syrup and 5 wt. % of high fructose corn syrup, and the mixture was stirred for dissolving at 60~70° C. Then, 5 wt. % of sugar, 0.05 wt. % of salt and 0.05 wt. % of native gellan gum were added and the mixture was stirred for dissolving at 80° C. for 15 minutes and cooled at 5° C. Then, 20 wt. % of boiled adzuki-beans, 15 wt. % of aka-namaan (paste of cooked red-colored beans), color and flavor were added, followed by mixing. This mixture was filled into a mould and frozen to provide an adzuki-bean candy comprising a uniform dispersion of adzuki-beans.

Example (6-11)

Soft Cream Nix

To 60 wt. % of water were added 3.1 wt. % of 75% starch syrup and 13.9 wt. % of granulated sugar, and the mixture was stirred for dissolving at 60~70° C. Then, 5.7 wt. % of skim milk powder, 6.2 wt. % of purified coconut oil, 0.3 wt. % of glycerin fatty acid ester, 0.05 wt. % of sucrose fatty acid ester, 0.03 wt. % of locust bean gum, 0.02 wt. % of carrageenan and 0.02 wt. % of native gellan gum were added. The mixture was made up to 100 wt. % and stirred for dissolving at 80° C. for 15 minutes. The solution was homogenized using a homogenizer at a primary pressure of 150 kg/cm$^2$ and a secondary pressure of 50 kg/cm$^2$ and cooled at 5° C. to provide a soft cream mix.

Whereas the control soft cream mix not containing native gellan gum (corresponding to the conventional product) underwent phase separation when left standing at 25° C. for 4 days, the test soft cream mix showed no separation even after one month, indicating that coconut oil could be dispersed in the water phase in a quite stable manner.

Example (6-12)

Soft Cream

Using the soft cream mix prepared in Example (6-11), a soft cream was produced in the conventional manner. This was a delicious soft cream with satisfactory overrun.

Example (6-13)

Cocoa-baked Pudding-1

To 40 wt. % of water were added 0.03 wt. % of native gellan gum, 20 wt. % of milk, 13 wt. % of sugar, 1.5 wt. % of cacao powder (fat 23%) and 4 wt. % of powdered whole milk, and the mixture was stirred for dissolving at 80° C. for 10 minutes and cooled to 60° C. Then, 20 wt. % of raw egg and 0.1 wt. % of flavor were added to the solution and the mixture was adjusted to a total of 100 wt. % and stirred. This preparation was filled into a heat-resistant vessel and treated in an oven at 180° C. for 1 hour to provide a cocoa-baked pudding.

This cocoa-baked pudding was attractive in appearance and palatability, indicating a uniform dispersion without aggregation or sedimentation of cacao particles.

Comparative Example (6-4)

Cocoa-baked Pudding

Using xanthan gum in lieu of native gellan gum, the procedure of Example (6-13) was otherwise repeated to provide a cocoa-baked pudding. The addition level of xanthan gum was varied within the range of 0.01 wt. % to 0.1 wt. % but the aggregation and sedimentation of cacao particles were found at all addition levels and the puddings were poor in appearance, showing the so-called "roughened" condition. Those "roughened" puddings showed a sediment composed of many cacao particles in the bottom layer and had a heterogeneous taste.

Example (6-14)

Cocoa-baked Pudding-2

To 40 wt. % of water were added 0.02 wt. % of native gellan gum, 0.05 wt. % of guar gum, 20 wt. % of milk, 13 wt. % of sugar, 1.5 wt. % of cacao powder (fat 23%) and 4 wt. % of powdered whole milk, and the mixture was stirred for dissolving at 80° C. for 10 minutes and cooled to 60° C. Then, 20 wt. % of raw egg and 0.1 wt. % of flavor were added to the above solution and the mixture was made up to 100 wt. %. The mixture was stirred, filled into a heat-resistant vessel, and treated in an oven at 180° C. for 1 hour to provide a cocoa-baked pudding.

This cocoa-baked pudding had an attractive appearance and a delicious taste reflecting a uniform dispersion without flocculation or sedimentation of cacao particles.

Example (6-15)

Ice Candy (with Fruit Pulp)

To 47.7 wt. % of water were added 6 wt. % of 75% starch syrup and 5 wt. % of high fructose corn syrup, and the mixture was stirred for dissolving at 60~70° C. Then, 5 wt. % of sugar, 0.05 wt. % of salt and 0.05 wt. % of native gellan gum were added, and the whole mixture was stirred for dissolving at 80° C. for 15 minutes and cooled at 5° C. Then, 20 wt. % of concentrated (⅕) pulp-containing mixed citrus fruit juice, color and flavor were added. This mixture was stirred, filled into a mould and frozen to provide a fruit pulp-containing ice candy. The fruit pulp had been evenly dispersed throughout this ice candy.

Example (6-16)

Frozen Cocoa Drink

A cocoa drink composition was prepared according to the recipe: native gellan gum 0.06 wt. %, cacao powder 3 wt. %, sugar 5 wt. %, HLB16 sucrose fatty acid ester 0.05 wt. %, and milk 10 wt. %. This composition was dispersed in water to make a total of 100 wt. % and treated with Homo-mixer at an elevated temperature of 70° C. Then, using a homogenizer, the dispersion was homogenized at a primary pressure of 150 kg/cm$^2$ and a secondary pressure of 50 kg/cm$^2$. The resulting homogenate was filled into a pressure-resistant glass vessel (35 mm in diameter, 130 mm high), which was then stoppered, and sterilized by autoclaving at 120° C. for 20 minutes. After cooling, the product was frozen at −20° C. to provide a frozen cocoa drink.

This cocoa drink remained to be a uniform dispersion without sedimentation of cacao particles both during freezing and after thawing and was very acceptable in appearance, taste, flavor and body.

Comparative Example (6-5)-(6-7)

Frozen Cocoa Drinks

Except that (1) 0.06 wt. % of gellan gum [Comparative Example (6-5)],
(2) 0.1 wt. % of carrageenan [Comparative Example (6-6)], and
(3) 0.2 wt. % of locust bean gum [Comparative Example (6-7)]

were respectively used in lieu of native gellan gum, the procedure of Example (6-16) was otherwise repeated to provide frozen cocoa drinks.

Those cocoa drinks began to form a sediment even before freezing and all the frozen products showed a definite difference in cacao powder content between the upper and lower layers. After thawing, the sediment of cacao particles was still more remarkable. Thus, there was a marked difference in dispersion stability between the frozen cocoa drink of Example (6-16) and any of the above cocoa drinks.

Example (6-17)

Jelly Grain-containing Drink

<Preparation of Jelly Grains>

To 80 wt. % of water were added 0.4 wt. % of gellan gum, 0.2 wt. % of sodium citrate, 15 wt. % of sugar, 0.2 wt. % of color, and 0.1 wt. % of flavor, and the mixture was stirred for dissolving at 80° C. for 10 minutes. The solution was made up with water to a total of 100 wt. % and added dropwise into a 5% solution of calcium lactate separately prepared in advance, further kept immersed therein for 30 minutes, and rinsed with water to provide jelly grains.

<Preparation of a Jelly Grain-containing Drink>

To 80 wt. % of water were added 0.03 wt. % of native gellan gum, 0.05 wt. % of HM pectin and 8 wt. % of sugar, and the mixture was stirred for dissolving at 85° C. for 10 minutes. Then, 6 wt. % of concentrated (1/5) mixed citrus fruit juice, 0.2 wt. % of citric acid (crystals) and 0.1 wt. % of flavor were added and the whole mixture was adjusted with water to make a total of 100 wt. %. This solution and the jelly grains prepared separately as above were filled, in a ratio of 9:1 by weight, into a container and, after closure, was pasteurized by heating to 93° C. (ultimate temperature). This container was gently swirled to disperse the jelly grains to provide a jelly grain-containing drink. Compared with the conventional drink of the type, this jelly grain-containing drink reflected a definitely superior dispersion stabilizing effect and no settling of jelly grains occurred after shaking.

Example (6-18)

Dairy Component-containing Coffee Drink

In 30 wt. % of water were placed 0.03 wt. % of native gellan gum, 6 wt. % of sugar and 0.03 wt. % of sugar ester, and the mixture was stirred for dissolving at 85° C. for 10 minutes. Then, 50 wt. % of a coffee extract supplemented with 1 wt. % of 10 wt. % sodium hydrogencarbonate solution was added, further followed by addition of 10 wt. % of milk. The mixture was homogenized at 70° C. and 150 kg/cm$^2$, filled into a can, and pasteurized at 120° C. for 20 minutes. The resultant milk-containing coffee drink showed no sedimentation.

Example (6-19)

Mayonnaise-style Dressing

In 50 wt. % of water was placed 0.2 wt. % of native gellan gum, and the mixture was stirred for dissolving at 85° C. for 10 minutes. Then, 6 wt. % of fermentation process vinegar, 0.5 wt. % of seasoning, 8 wt. % of egg yolk and 35 wt. % of salad oil were added and the mixture was adjusted with water to 100 wt. %. This mixture was pre-emulsified with Homo-mixer and further emulsified with a colloid mill to provide a stable mayonnaise-style dressing showing no floating oil.

Example (6-20)

Emulsion Type Dressing-1

To 40 wt. % of water were added 0.03 wt. % of native gellan gum, 0.3 wt. % of xanthan gum and 5 wt. % of sugar, and the mixture was stirred for dissolving at 80° C. for 10 minutes. Then, 12.5 wt. % of fermentation process vinegar (acidity 8%), 0.6 wt. % of sodium L-glutamate, 0.2 wt. % of seasoning and 3 wt. % of salt were added and the whole mixture was further stirred at 80° C. for 10 minutes. The mixture was made up to 65 wt. % with water and cooled to 40° C. Then, 35 wt. % of corn salad oil was added and the mixture was emulsified with Homo-mixer to provide a stable emulsion type dressing.

Example (6-21)

Emulsion Type Dressing-2

To 40 wt. % of water were added 0.03 wt. % of native gellan gum, 0.3 wt. % of xanthan gum and 5 wt. % of sugar, and the mixture was stirred for dissolving at 20° C. for 10 minutes. Then, 12.5 wt. % of fermentation process vinegar (acidity 8%), 0.6 wt. % of sodium L-glutamate, 0.2 wt. % of seasoning and 3 wt. % of salt were added and the mixture was further stirred at 80° C. for 10 minutes and made up to 65 wt. % with water. After cooling to 40° C., 35 wt. % of corn salad oil was added and the mixture was emulsified with Homo-mixer to provide a stable emulsion type dressing.

Example (6-22)

Concentrated Drink Base

To 70 wt. % of water were added 0.03 wt. % of native gellan gum, 1 wt. % of water-soluble soybean polysaccharide (trade name, SM-700, San-eigen F. F. I.) and 20 wt. % of sugar, and the mixture was stirred for dissolving at 80° C. for 10 minutes. Then, 2 wt. % of 50% lactic acid and 2 wt. % of concentrated (1/5) pulp-containing mixed citrus fruit juice were added and made up with water to a total of 100 wt. % to provide a concentrated drink base.

When this concentrated drink base was blended with milk in a ratio of 1:1, a milk drink containing the fruit pulp dispersed in a stable condition was obtained.

Example (6-23)

Separate-type Dressing

To 40 wt. % of water were added 0.03 wt. % of native gellan gum, 0.1 wt. % of xanthan gum and 5 wt. % of sugar, and the mixture was stirred for dissolving at 85° C. for 10 minutes. Then, 12 wt. % of fermentation process vinegar, 1 wt. % of seasoning and 3 wt. % of salt were added to the above solution and the mixture was further stirred for dissolving at 85° C. for 10 minutes. The mixture was made up to 65 wt. % with water and cooled to room temperature. This mixture and 35 wt. % of salad oil were filled together into a vessel to provide a separate type dressing. Although this dressing consisted of discrete layers, viz. an oil layer and a water layer, but the ingredients in the aqueous phase had been uniformly dispersed.

Unlike the dressing prepared by intense stirring with Homo-mixer or homogenization with a homogenizer or the like (cf. Example (6-20) and Example (6-21)), the dressing obtained by the above method does not form a homogeneous mixture even when the vessel is shaken by hand but soon undergoes phase separation on standing.

Example (6-24)

Soy-boiled Layer

A soy-boiled layer was prepared in the per se known manner using 78 wt. % of soy, 0.5 wt. % of native gellan gum, 0.3 wt. % of tamarind seed gum, 6 wt. % of starch syrup, 11 wt. % of sugar, 8 wt. % of layer and 0.3 wt. % of seasoning.

This soy-boiled layer, when put into the mouth, is readily separated into individual wafers of layer in the presence of saliva and, at the same time, the flavor of layer diffuses throughout the mouth. Moreover, the layer wafers are not agglomerated in the mouth and the product shows a delicious taste free from the solid foreign body feel which is a disadvantage of the conventional soy-boiled layer.

Example (6-25)

Dragon Fruit Drink

To 50 wt. % of water were added 20 wt. % of high fructose corn syrup, 0.3 wt. % of citric acid (crystals) and 0.05 wt. % of native gellan gum, and the mixture was stirred for dissolving at 85° C. for 10 minutes. Then, 10 wt. % of dragon fruit seeds and 0.3 wt. % of flavor were added and the mixture was adjusted to 100 wt. % to provide a drink having an appearance resembling the pulp of dragon fruit and in which the seeds had been uniformly dispersed in a stable manner.

Example (6-26)

Coffee Cream

To 70 wt. % of water were added 0.08 wt. % of native gellan gum, 4.5 wt. % of skim milk powder, 3 wt. % of casein sodium, 0.5 wt. % of sugar ester, 0.2 wt. % of disodium phosphate and 0.06 wt. % of carrageenan, and the mixture was stirred for dissolving at 85° C. for 10 minutes. Then, 15 wt. % of coconut oil and 0.05 wt. % of flavor were added under stirring with Homo-mixer and the mixture was adjusted to 100 wt. % with water, homogenized at 50 kg/cm$^2$ and finally cooled to 10° C. to provide a cream characterized by good emulsion stability.

Example (6-27)

Fruit Pulp-containing Carbonated Drink

Using water, 0.04 wt. % of native gellan gum, 12 wt. % of sugar and 1 wt. % of concentrated (⅕) pulp-containing mixed citrus fruit juice were made up to 50 wt. % and the mixture was pasteurized at 85° C. for 10 minutes. This mixture was blended with 50 wt. % of carbonated water to provide a carbonated drink containing the fruit pulp uniformly dispersed without sedimentation.

Example (6-28)

Insoluble Calcium-containing Drink

Using water, 0.05 wt. % of native gellan gum, 0.2 wt. % of calcium carbonate, 5 wt. % of sweetener, 0.01 wt. % of color and 0.1 wt. % of flavor were made up to 100 wt. %, filled into a container, and subjected to retort sterilization at 121° C. for 20 minutes to provide a drink containing insoluble calcium dispersed in a stable manner.

Example (6-29)

Goma-dare (Sesame Sauce)
(1) Preparation of Dispersion Stabilizer
The dispersion stabilizer of the invention in the form of a powder was prepared by formulating 0.2 wt. % of native gellan gum and 0.26 wt. % of pectin.
(2) Preparation of Goma-dare
To water were added 10 wt. % of vinegar, 13 wt. % of kneaded sesame, 7 wt. % of starch syrup and 4 wt. % of mirin (saccharification product of rice starch) and the mixture was thoroughly stirred. Then, 10 wt. % of sugar and 0.55 wt. % of the powdery dispersion stabilizer prepared in (1) were added and the mixture was stirred under heating at 80° C. for 10 minutes.

Then, using care not to allow the liquid temperature to fall below 80° C., 20 wt. % of prewarmed soy was added in small portions. Then, a mixture of 2.4 wt. % of salt, 1.5 wt. % of seasoning, and 1 wt. % of trisodium citrate, dissolved in a small amount of hot water in advance, was added and the whole mixture was stirred for dissolving. After this solution was heated to 90° C. with constant stirring, a sufficient amount of water was added to compensate for the evaporation loss and make a total of 100 wt. %. This solution was filled into a container when hot to provide a goma-dare (sesame sauce) (½ concentrate, pH 4.8, Brix 37°).

The resultant goma-dare contained sesame in a stably dispersed state and, when measured with a Type B viscometer (temperature 20° C.), showed a viscosity of 450 cps. Even after this goma-dare was diluted two-fold with water, a stable dispersion of sesame was maintained, indicating a high dispersion stabilizing effect.

Example 7

Thickened Composition Additive

Example (7-1)

The materials shown in Table 3 were blended in one operation and dissolved by heating at 80° C. for 10 minutes (hereinafter referred to as batch). Meanwhile, 0.5 g of native gellan gum was placed in 50 g of water and dissolved by stirring at 80° C. for 10 minutes (hereinafter referred to as NGG solution).

Separately, 2.5 g of tamarind seed gum was placed in 49 g of water and dissolved by heating at 80° C. with stirring for 10 minutes (hereinafter referred to as TM solution).

The NGG solution and TM solution were added to the batch and the mixture was stirred to provide a tare (sauce) for baked meat (invention product 7-1). The concentration of native gellan gum in this tare (i.e. the final concentration in the food) was 0.05 wt. % and that of tamarind seed gum was 0.25 wt. %.

TABLE 3

| Recipe | Amount (g) |
| --- | --- |
| Soy | 282 |
| Red wine | 210 |
| Starch syrup | 50 |
| Honey | 28 |
| Raw garlic | 10 |
| Onion powder | 2 |
| Sugar | 270 |
| Salt | 12 |
| Citric acid (crystals) | 2 |
| Sodium L-glutamate | 2 |
| Ground sesame | 2 |
| Sesame oil | 8 |
| Beef extract | 10 |
| Flavor & spice | 10 |

Example (7-2)

A powder blend of 0.5 g of native gellan gum and 2.5 g of tamarind seed gum was placed in 99 g of water and dissolved by heating at 80° C. with constant stirring for 10 minutes. Then, the batch according to Example (7-1) was added, followed by stirring, to provide a tare for baked meat (invention product 7-2).

Comparative Example (7-1)

Several kinds of tare for baked meat were prepared by repeating the procedure of Example (7-1) except that (1) gellan gum was used in lieu of native gellan gum (comparative product 7-1);

(2) tamarind seed gum was used in lieu of native gellan gum (i.e. tamarind seed gum alone was used) (comparative product 7-2);

(3) water was used in lieu of tamarind seed gum (i.e. native gellan gum alone was used) (comparative product 7-3);

(4) xanthan gum, the conventional thickener, was used in lieu of native gellan gum and tamarind seed gum (comparative product 7-4); provided, however, that since this gum could not be dissolved in water to any concentration over 2 wt. % because of the high viscosity developed, 2 g of xanthan gum was dissolved in 100 g of water and the batch was added to this solution under stirring; or (5) water was used in lieu of native gellan gum and tamarind seed gum (comparative product 7-5).

The tare sauces according to Examples (7-1) and (7-2) [invention products (7-1) and (7-2)] and the tare sauces according to Comparative Example (7-1) ~(1 through 5) [comparative products (7-1) ~(7-5)] were respectively applied to baked meat to evaluate their utility as tare.

In addition, invention products (7-1) and (7-2) and comparative products (7-1) ~(7-5) were left standing at 35° C. for one month to evaluate their stability.

As a result, invention product (7-1) adhered in a sufficient amount, indicating a satisfactory viscosity. Moreover, even when left standing for 1 month, it showed no separation of contents attesting to the dispersion stabilizing effect due to the thickening method used. Invention product (7-2) also gave an effect comparable to the effect obtained with invention product (7-1).

In contrast, comparative product (7-1) formed gels on baked meat and was not useful. The gels could be disintegrated and eaten together with the baked meat but this way of injection is clearly at odds with the definition of tare. Comparative products (7-2), (7-3) and (7-5) had little viscosity and, when applied to baked meat, dripped down from the meat immediately so that they could not serve as tare. After 1 month of standing, the oil separated out on the surface, indicating poor stability. Comparative product (7-4) performed best of all, among comparative products, but still was insufficient in viscosity and had room for improvement for use as tare. It was also poor in stability, showing settling of sesame seeds.

Example (7-3)

The following ingredient materials were blended in one step and stirred at 90° C. for 5 minutes.

| | |
|---|---|
| Cream cheese | 45 wt. % |
| Sweetened condensed whole milk | 13 |
| Plain yoghurt | 8 |
| Egg white powder | 3 |
| Gelatin | 1 |
| Starch | 1 |

| -continued | |
|---|---|
| Margarine | 6 |
| Sugar | 3.5 |
| Lemon juice | 1.5 |
| Flavor | 0.1 |
| Native gellan gum | 0.15 |
| Locust bean gum | 0.2 |
| Water | Balance |
| Total | 100 wt. % |

This solution was poured into a star-shaped mould, 1.5 cm square and 4 cm high, to a height of 1 cm and then cooled to 5° C. to provide a star-shaped cheese style food.

The solution had been evenly distributed throughout the mould cavity even to the apices of the asterisk and, when released from the mould, gave a neat cheese-style food.

Example (7-4)

All the following materials were blended, stirred at 90° C. for 5 minutes, and further boiled down to 100 wt. % to provide a full-bodied custard cream.

| | |
|---|---|
| Corn starch | 2 wt. % |
| Sugar | 16 |
| Skim milk powder | 4 |
| Starch syrup | 7 |
| Condensed skim milk | 3 |
| Salt-free margarine | 6.5 |
| Whole egg | 9.8 |
| Flavor | 0.5 |
| Gellan gum | 0.2 |
| Native gellan gum | 0.05 |
| Locust bean gum | 0.2 |
| Water | 56 |
| Total | 107.25 wt. % |

Example (7-5)

All the following materials were blended, stirred at 90° C. for 5 minutes, and further boiled down to 100 wt. % to provide a well-bodied flour paste.

| | |
|---|---|
| Sugar | 20 wt. % |
| Corn starch | 3 |
| Soft flour | 3 |
| Skim milk powder | 6.25 |
| Margarine | 10 |
| Starch syrup | 8 |
| Color | 0.05 |
| Flavor | 0.12 |
| Native gellan gum | 0.05 |
| Tamarind seed gum | 0.1 |
| Water | 58 |
| Total | 108.57 wt. % |

Example (7-6)

The materials were blended according to the following recipe, stirred and filtered to provide a water-based ink for the ball-point pen.

| | |
|---|---|
| Water black 187 (Orient Chemical) | 7 wt. % |
| Propylene glycol | 30 |
| Native gellan gum | 0.05 |
| Guar gum | 0.1 |
| Potassium oleate | 0.5 |
| Omadine sodium | 0.1 |
| Urea | 1 |
| Water | Balance |
| Total | 100 wt. % |

Example (7-7)

The materials were blended according to the following recipe and dispersed in a ball mill for 12 hours to provide a silver-colored water-based metallic color ink for the ball-point pen.

| | |
|---|---|
| IRIODIN 103 (Merck) | 10 wt. % |
| Propylene glycol | 20 |
| Native gellan gum | 0.07 |
| Locust bean gum | 0.7 |
| Potassium oleate | 0.5 |
| Omadine sodium | 0.1 |
| Urea | 1 |
| Water | Balance |
| Total | 100 wt. % |

Example (7-8)

According to the recipe shown below, the materials were stirred with a laboratory mixer for 1 hour to provide a silver-colored water-based metallic ink for the ball-point pen.

| | |
|---|---|
| Aluminum paste WB0230 (Toyo Aluminum) | 10 wt. % |
| Propylene glycol | 10 |
| Native gellan gum | 0.07 |
| Guar gum | 0.3 |
| Glycerin | 10 |
| Polyoxyethylene (10) nonylphenyl ether | 1 |
| Antiseptic | 0.1 |
| Water | Balance |
| Total | 100 wt. % |

Example (7-9)

According to the following recipe, a water-based paint (resin solids 30 wt. %) was prepared by the conventional procedure.

| Component | Dry basis (g) |
|---|---|
| Hydrafine (pigment: J. M. Huber) | 100 |
| Dow 620 (binder: styrene-butadiene latex) (Dow Chemical) | 13 |
| Native gellan gum | 0.19 |
| Pullulan | 9.5 |
| Flowco 501 (calcium stearate dispersion) (Mallinckrodt) | 0.5 |
| Hercules 831 (defoamer: Hercules) | 0.2 |

Example (7-10)

According to the following recipe, a water-based paint was prepared by the conventional procedure.

| | |
|---|---|
| Cyanine Green | 0.6 wt. % |
| Titanium dioxide | 5.5 |
| Barium sulfate | 22 |
| Polymethylolmelamine, 60% aq. sol. | 38 |
| Native gellan gum 0.1% (Guar gum, 0.5% aq. sol.) | 33.9 |
| Total | 100 wt. % |

Example (7-11)

According to the following recipe, a concrete was prepared by the conventional procedure.

| | | | |
|---|---|---|---|
| Max. size of coarse aggregate | | | 20 mm |
| Water/binding component ratio | | | 30% |
| Percentage of fine aggregate | | | 41% |
| Unit weight (kg/m³) | Water | | 150 |
| | Cement | | 150 |
| | Blast furnace slag | | 150 |
| | Fly ash | | 200 |
| | Fine aggregate | | 663 |
| | Coarse aggregate | | 940 |
| | Admixture (wt. % relative to binding component) | Water-reducing agent | 5 (1.0%) |
| | | A–E agent | 0.75 (0.15%) |
| | | Gum mixture | 0.5 (0.1%) |

Water-reducing agent: naphthalenesulfonic acid-formaldehyde polycondensate
A–E water-reducing agent: ligninsulfonic acid compound-polyol complex
Gum mixture: native gellan gum-tara gum (1:4)

Example (7-12)

According to the following recipes, materials for each of the black tea pudding, milk pudding and coffee pudding components were respectively blended, stirred for dissolving at 80° C. for 15 minutes, and allowed to cool. When the temperature had dropped to 65° C., equal portions of the respective mixtures were concurrently poured into a pudding cup and cooled to solidify at 10° C. to provide a column-wise tri-color pudding.

| | |
|---|---|
| <Black tea pudding component> | |
| Sugar | 10 wt. % |
| Milk | 30 |

-continued

| | |
|---|---|
| Skim milk powder | 5 |
| Kappa-carrageenan | 0.2 |
| Locust bean gum | 0.1 |
| Glycerin fatty acid ester | 0.1 |
| Black tea extract | 6 |
| Flavor | 0.1 |
| Native gellan gum | 0.1 |
| Water | Balance |
| Total | 100 wt. % |
| <Milk pudding component> | |
| Sugar | 10 wt. % |
| Milk | 30 |
| Skim milk powder | 5 |
| Butter | 3 |
| Kappa-carrageenan | 0.1 |
| Locust bean gum | 0.2 |
| Glycerin fatty acid ester | 0.1 |
| Flavor | 0.1 |
| Native gellan gum | 0.1 |
| Water | Balance |
| Total | 100 wt. % |
| <Coffee pudding component> | |
| Sugar | 10 wt. % |
| Milk | 30 |
| Skim milk powder | 5 |
| Kappa-carrageenan | 0.1 |
| Locust bean gum | 0.1 |
| Gellan gum | 0.05 |
| Glycerin fatty acid ester | 0.1 |
| Coffee extract | 5 |
| Flavor | 0.1 |
| Native gellan gum | 0.1 |
| Water | Balance |
| Total | 100 wt. % |

In the above production process for the tricolor pudding, the respective column-forming compositions remained to gel as yet in the filling stage but had been sufficiently thickened by the synergistic action of native gellan gum and locust bean gum. Therefore, those compositions did not intermingle in this filling stage so that the product tricolor pudding presented with a well-defined interface between columns. Moreover, even though this pudding contained black tea and coffee extracts, it showed no roughness around the interfaces and had a delicious taste.

It was found that in accordance with this invention, a high-quality tricolor pudding characterized by clear interfaces and freedom from cohesion defects can be provided by an expedient procedure of pouring the column-forming compositions concurrently into a pudding cup.

Comparative Example (7-2)

Except that native gellan gum only was omitted from the recipes shown in Example (7-12), the procedure of Example (7-12) was otherwise repeated to provide a tricolor pudding. In this case, however, a pudding could be obtained at any rate but because of insufficient viscosity, the column-forming compositions intermingled so that the interfaces were ill-defined and the product assumed a commercially unacceptable dirty appearance.

Example (7-13)

In the procedure of Example (7-12), at the stage of filling the black tea, milk and coffee pudding component compositions into a pudding cup, the cup was rotated gently in a horizontal direction about its central axis, whereby a tricolor pudding with a well-defined eddy pattern was obtained. A pudding showing a similar eddy pattern could also be obtained when the cup was held stationary and the nozzle plate was rotated horizontally about the centerline of the cup with the relative position of the nozzle orifices for dispensing the respective compositions being unchanged.

Example (7-14)

The materials for the black tea pudding, milk pudding and coffee pudding components according to the recipes shown in Example (7-12) were respectively prepared and stirred for dissolving at 80° C. for 15 minutes and allowed to cool. When the temperature had fallen to 65° C., the respective compositions were serially filled into a pudding cup each in an amount equal to one-third of the capacity and, then, cooled to solidify at 10° C., whereby a tricolor pudding consisting of three horizontal layers was obtained. This pudding showed well-defined interfaces between layers.

It was found that, in accordance with this invention, a tricolor pudding with well-defined borders can be produced without cooling the respective components to solidify every time each component has been poured into the cup.

Example (7-15)

In the procedure of Example (7-12), when the black tea pudding, milk pudding and coffee pudding components were poured, the respective components were held at 65° C. and serially filled into the cup, one volume part each, and every time the filling operation for each part was completed, the cup was rotated through 15 degrees about its centerline while being held in a horizontal position or the nozzle means was rotated through 15 degrees about the centerline of the cup to provide a pudding having a staggered pattern.

Example (7-16)

According to the following recipe, the materials for the orange jelly component and lemon jelly component were respectively blended and stirred at 80° C. for 10 minutes. When the temperature had dropped to 65° C., those compositions were concurrently poured, in equal portions, into a cup to provide a two-colored jelly with a well-defined vertical interface.

| | |
|---|---|
| <Orange jelly component> | |
| Sugar | 20 wt. % |
| Kappa-carrageenan | 0.3 |
| Locust bean gum | 0.2 |
| Xanthan gum | 0.05 |
| Trisodium citrate | 0.15 |
| Citric acid | 0.25 |
| Concentrated (1/5) orange juice | 6 |
| Flavor | 0.1 |
| Native gellan gum | 0.1 |
| Water | Balance |
| Total | 100 wt. % |
| <Lemon jelly component> | |
| Sugar | 20 wt. % |
| Kappa-carrageenan | 0.2 |
| Locust bean gum | 0.2 |
| Xanthan gum | 0.05 |
| Trisodium citrate | 0.15 |
| Citric acid | 0.1 |
| Lemon juice | 2 |

-continued

| | |
|---|---|
| Flavor | 0.1 |
| Native gellan gum | 0.1 |
| Water | Balance |
| Total | 100 wt. % |

In this production process for a two-color jelly, the respective compositions remained to gel as yet in the filling stage but had been well thickened by the synergistic action of native gellan gum, locust bean gum and xanthan gum. Therefore, those compositions did not intermingle in the filling stage so that the resultant jelly showed a well-defined interface.

It was found that, in accordance with this invention, a two-color jelly having a well-defined interface can be prepared by an expedient procedure of filling the component compositions concurrently into jelly cup.

Comparative Example (7-3)

Except that native gellan gum only was excluded from the recipes shown in Example (7-16), the procedure of Example (7-16) was otherwise repeated to provide a two-color jelly. In this case, however, although a jelly could be obtained at any rate, the compositions intermingled to give a jelly having an ill-defined borderline and, hence, the product assumed a dirty appearance which was not commercially acceptable.

Example (7-17)

In the procedure of Example (7-16), at the stage of filling the components into the jelly cup, the respective compositions were serially poured each in an amount equal to one-half of the capacity to provide a two-color jelly having a well-defined horizontal interface. This jelly showed a neat interlayer borderline.

It was found that, in accordance with this invention, a two-color jelly having a well-defined interface can be provided without resort to cooling-solidifcation upon completion of a filling operation for each composition.

The following experiment examples illustrate the invention relevant to embodiment (7) in further detail.

Experiment Example (7-1)

Figure 4:
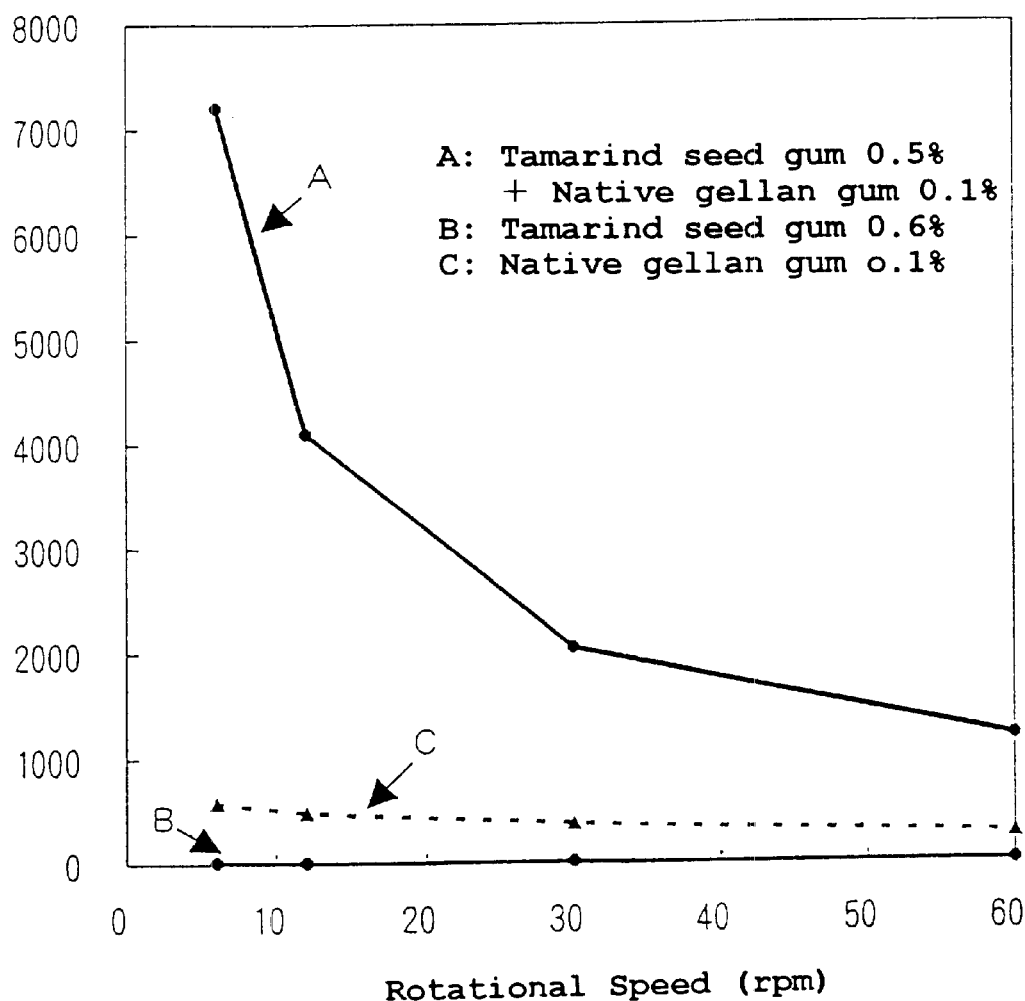
FIGS. 4–46 are diagrams showing the results of Experiment Example (7-1) Experiment Example (7~24), respectively.

To 50 g of water was added 0.1 g of native gellan gum, and the mixture was heated for dissolving at 80° C. for 10 minutes. Separately, 0.5 g of tamarind seed gum was placed in 50 g of water and heated for dissolving at 80° C. for 10 minutes. The two solutions were mixed together and the viscosity was measured. The viscosity measurement was carried out with a Type B viscometer (Tokyo Instrument) at 20° C. (This applies to viscosity measurements referred to hereinafter). The results are shown in FIG. 4. Thus, the lower the rotational speed was, the higher was the viscosity reading and a very high viscosity value of 7200 cps was noted at the rotational speed of 6 rpm. Moreover, this solution showed no gelation at all.

On the other hand, the viscosity of a 0.1 wt. % solution of native gellan gum alone and the viscosity of a 0.6 wt. % solution of tamarind seed gum alone were respectively measured but neither solution showed a sufficiently high viscosity.

Experiment Example (7-2)

Figure 5:
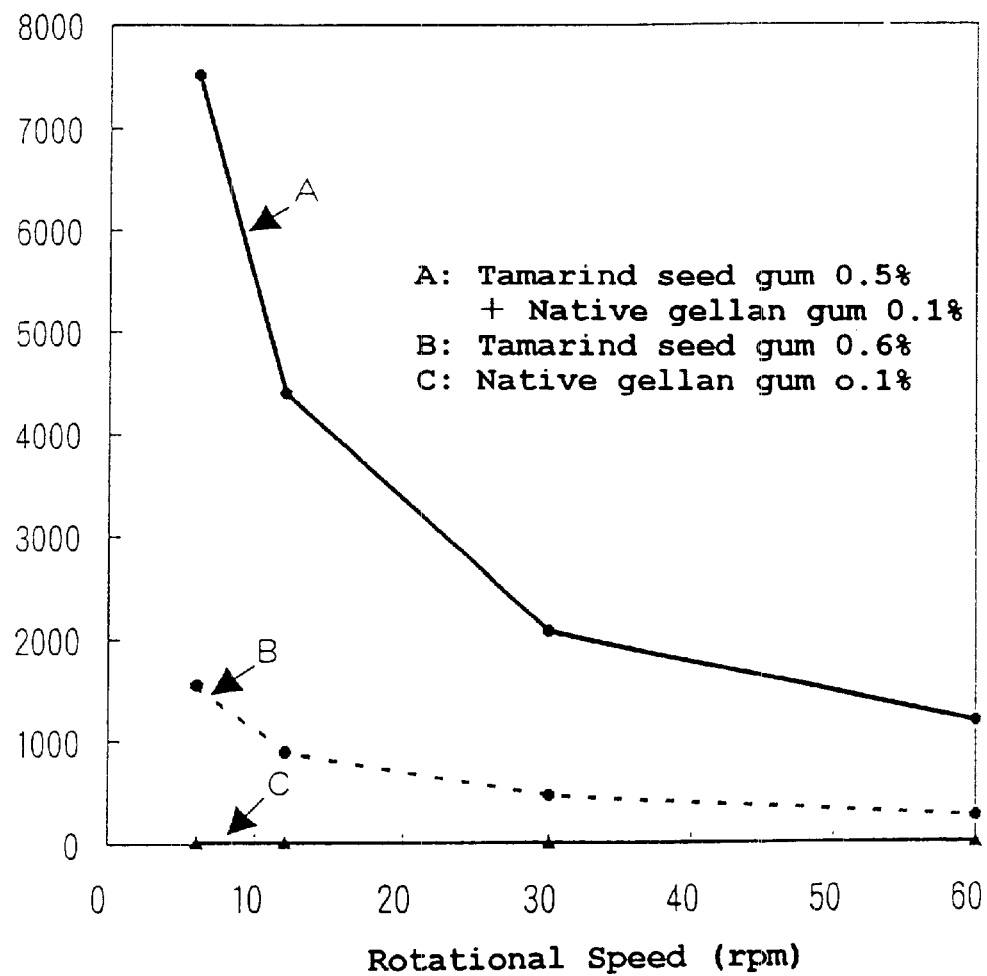

To 50 g of water was added 0.1 g of native gellan gum, and the mixture was heated for dissolving at 80° C. for 10 minutes and adjusted to pH 3.5. Separately, 0.5 g of tamarind seed gum was placed in 50 g of water and heated for dissolving at 80° C. for 10 minutes and adjusted to pH 3.5. The two solutions were admixed and the viscosity of the combined solution was measured. As shown in FIG. 5, the lower the rotational speed was, the higher was the viscosity reading and a viscosity of 7520 cps, higher than the value obtained in Experiment Example (7-1), was recorded at the rotational speed of 6 rpm. In addition, this solution showed no evidence of gelation at all.

On the other hand, the viscosity of a 0.1 wt. % solution of native gellan gum alone (pH 3.5) and that of a 0.6 wt. % solution of tamarind seed gum alone (pH 3.5) were measured but neither solution showed a sufficient degree of viscosity.

Experiment (7-3)

Figure 6:
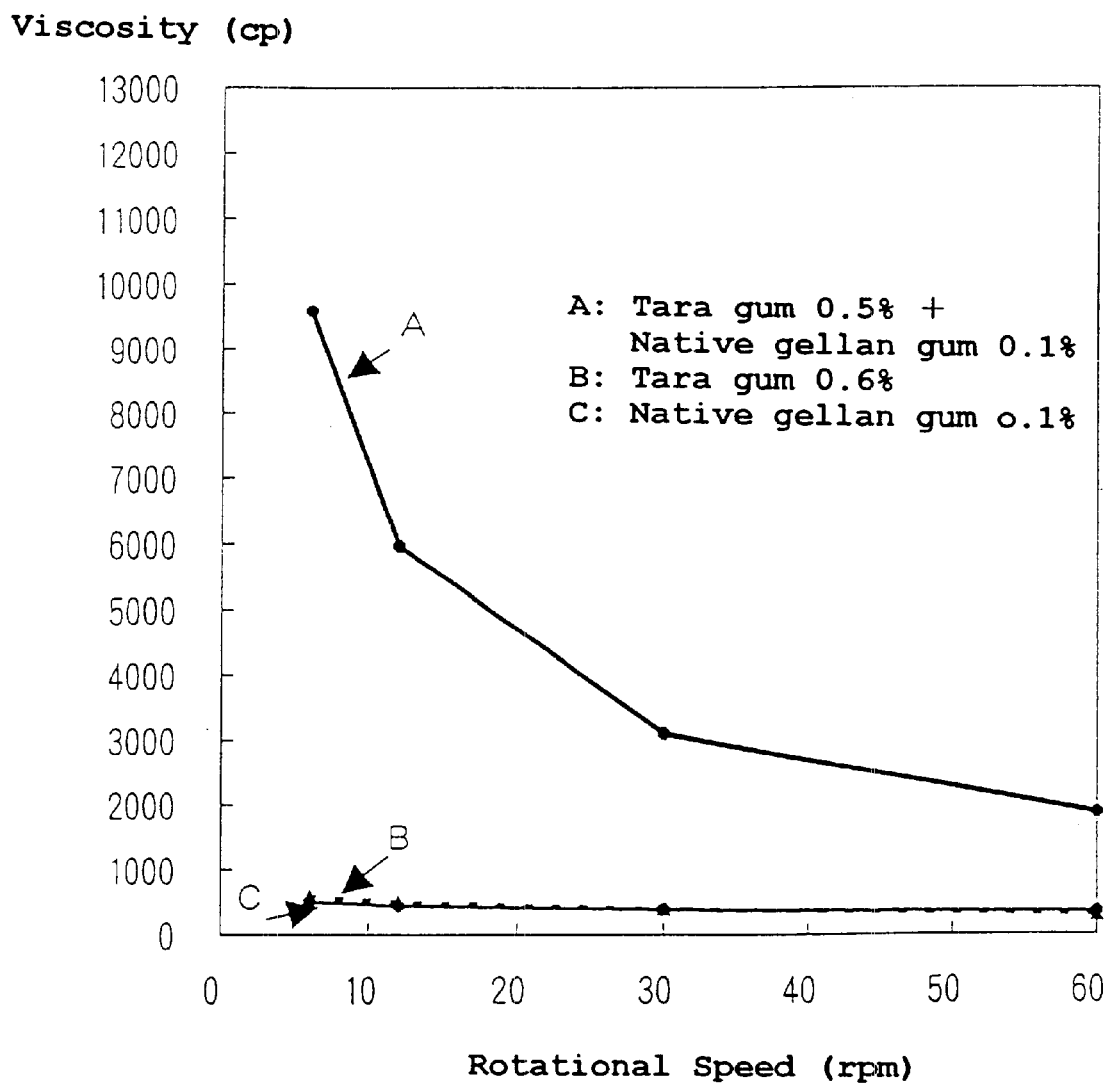

To 50 g of water was added 0.1 g of native gellan gum, and the mixture was heated for dissolving at 80° C. for 10 minutes. Separately, 0.5 g of tara gun was placed in 50 g of water and heated for dissolving at 80° C. for 10 minutes. The two solutions were admixed and the viscosity of the combined solution was measured. As shown in FIG. 6, the lower the rotational speed was, the higher was the viscosity reading, and a viscosity value of as high as 9580 cps was recorded at the rotational speed of 6 rpm. This solution showed no evidence of gelation at all.

Figure 7:
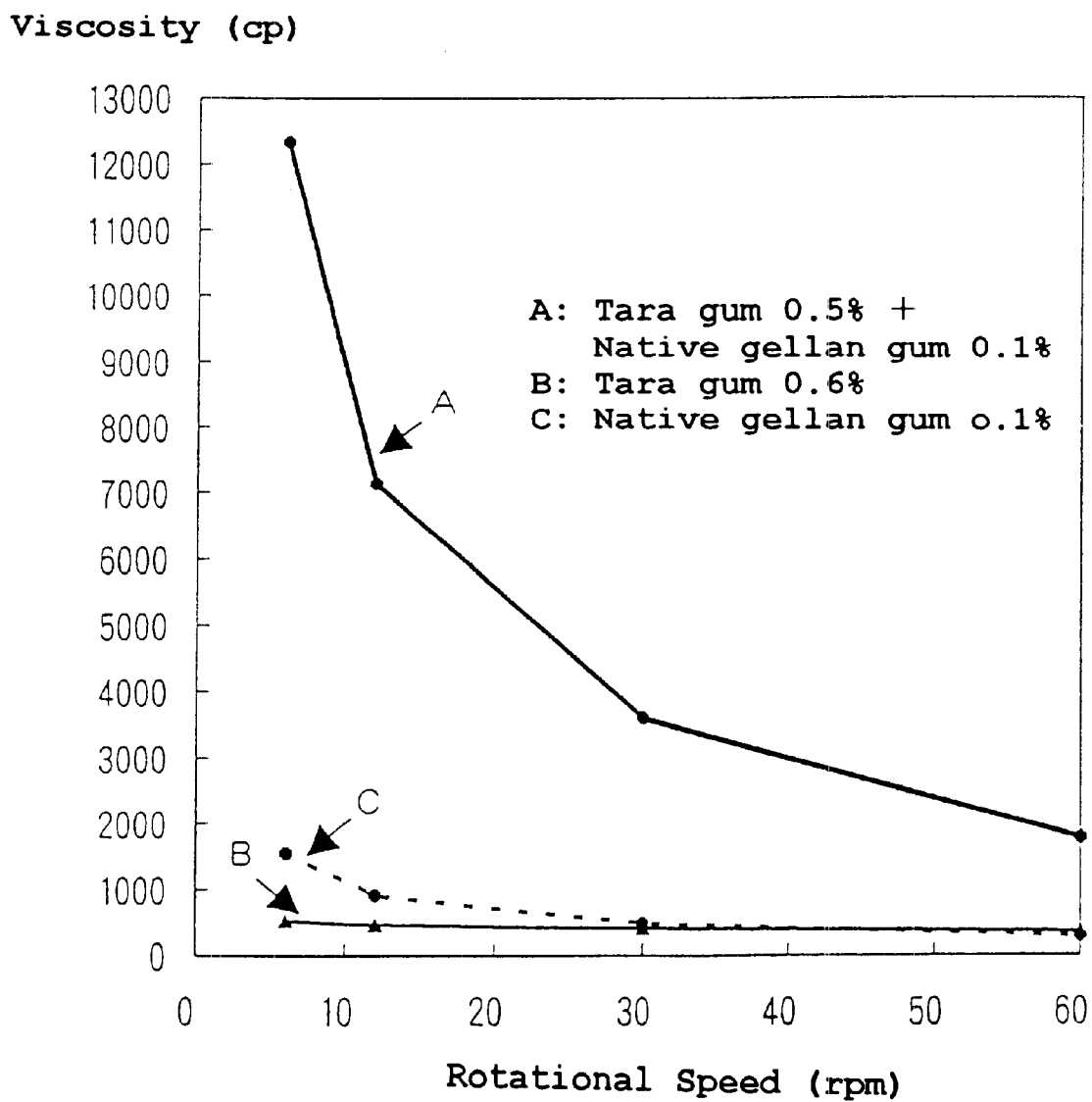

Furthermore, as in Experiment Example (7-2), the solutions adjusted to pH 3.5 were prepared and admixed and the viscosity of the combined solution was measured. As shown in FIG. 7, the lower the rotational speed was, the higher was the viscosity reading, and a viscosity value of as high as 12320 cps was recorded at the rotational speed of 6 rpm. This solution showed no evidence of gelation at all.

As controls, in the respective cases mentioned above, the viscosity of a 0.1 wt. % solution of native gellan gum alone and that of a 0.6 wt. % solution of tara gum alone were measured but neither solution showed a sufficient degree of viscosity.

Experiment Example (7-4)

Figure 8:
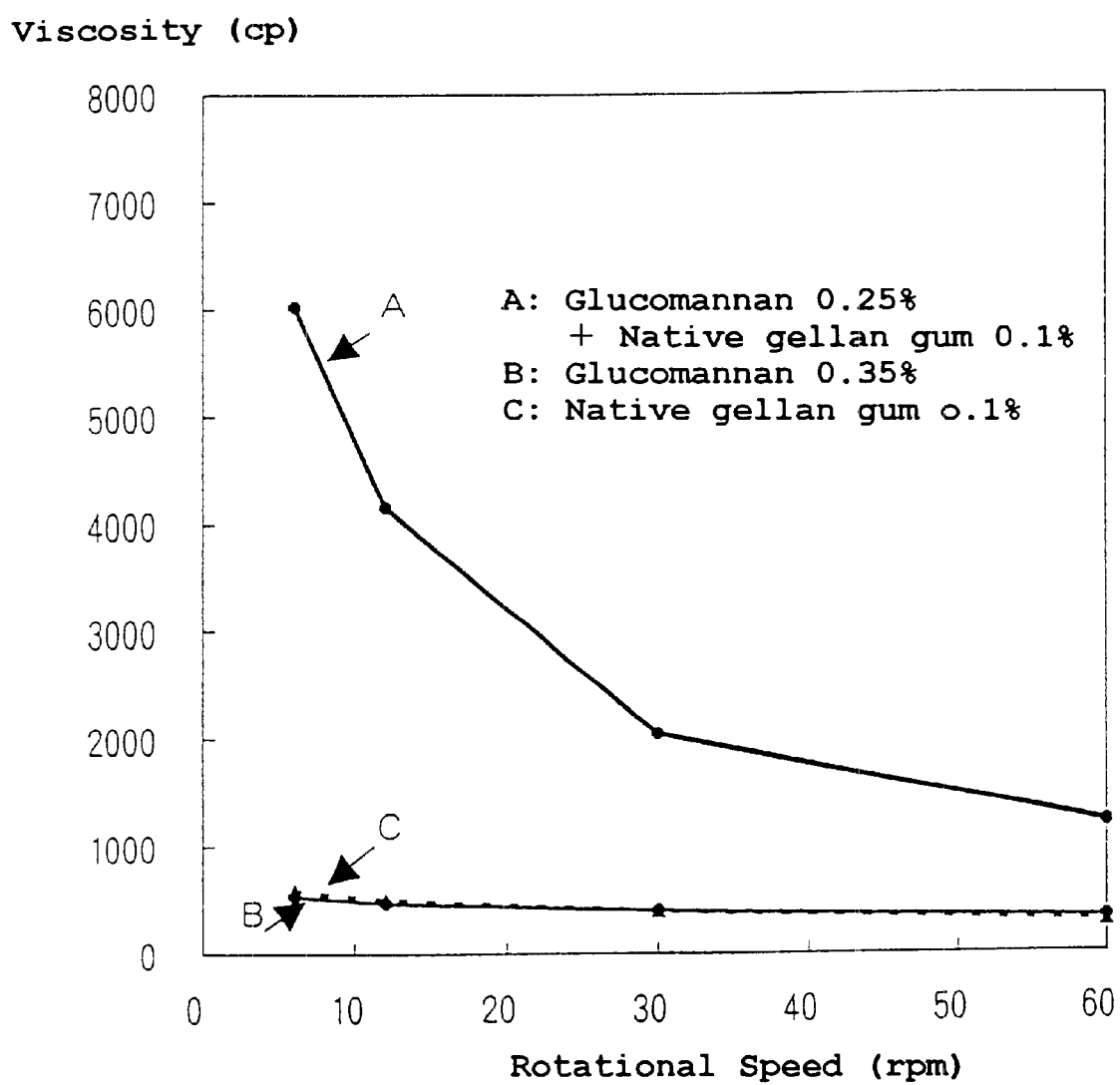

To 50 g of water was added 0.1 g of native gellan gum, and the mixture was heated for dissolving at 80° C. for 10 minutes. Separately, 0.25 g of glucomannan was placed in 50 g of water and heated for dissolving at 80° C. for 10 minutes. The two solutions were admixed and the viscosity was measured. As shown in FIG. 8, the lower the rotational speed was, the higher was the viscosity reading, and a viscosity value of as high as 6020 cps was recorded at the rotational speed of 6 rpm. This solution showed no evidence of gelation at all.

Figure 9:
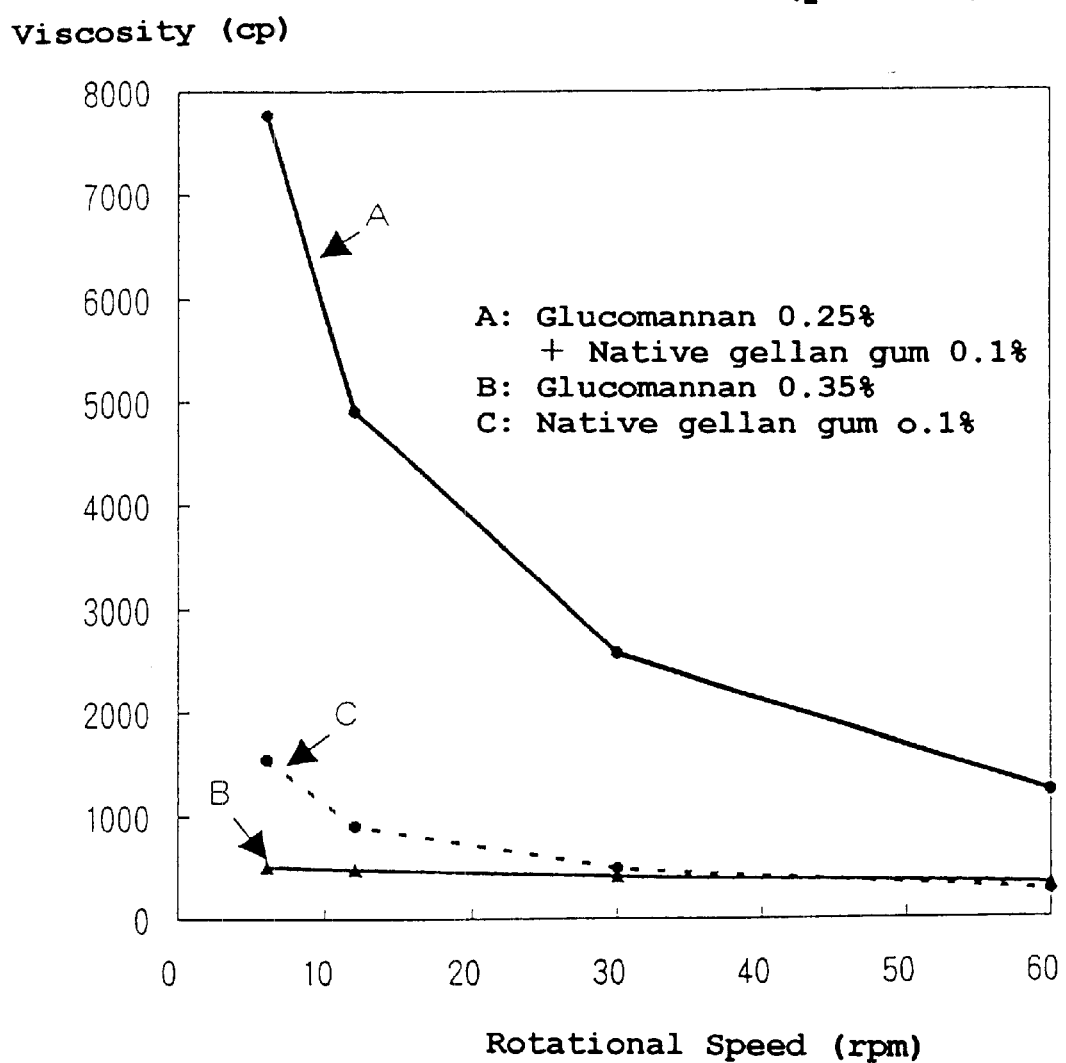

Furthermore, as in Experiment Example (7-2), the solutions adjusted to pH 3.5 in advance were admixed and the viscosity of the combined solution was measured. As shown in FIG. 9, the lower the rotational speed was, the higher was the viscosity reading, and a viscosity value of as high as 7760 cps was recorded at the rotational speed of 6 rpm. This solution showed no evidence of gelation at all.

As controls, in the respective cases mentioned above, the viscosity of a 0.1 wt. % solution of native gellan gum alone and that of a 0.35 wt. % solution of glucomannan alone were measured but neither solution showed a sufficient degree of viscosity.

Experiment Example (7-5)

Figure 10:
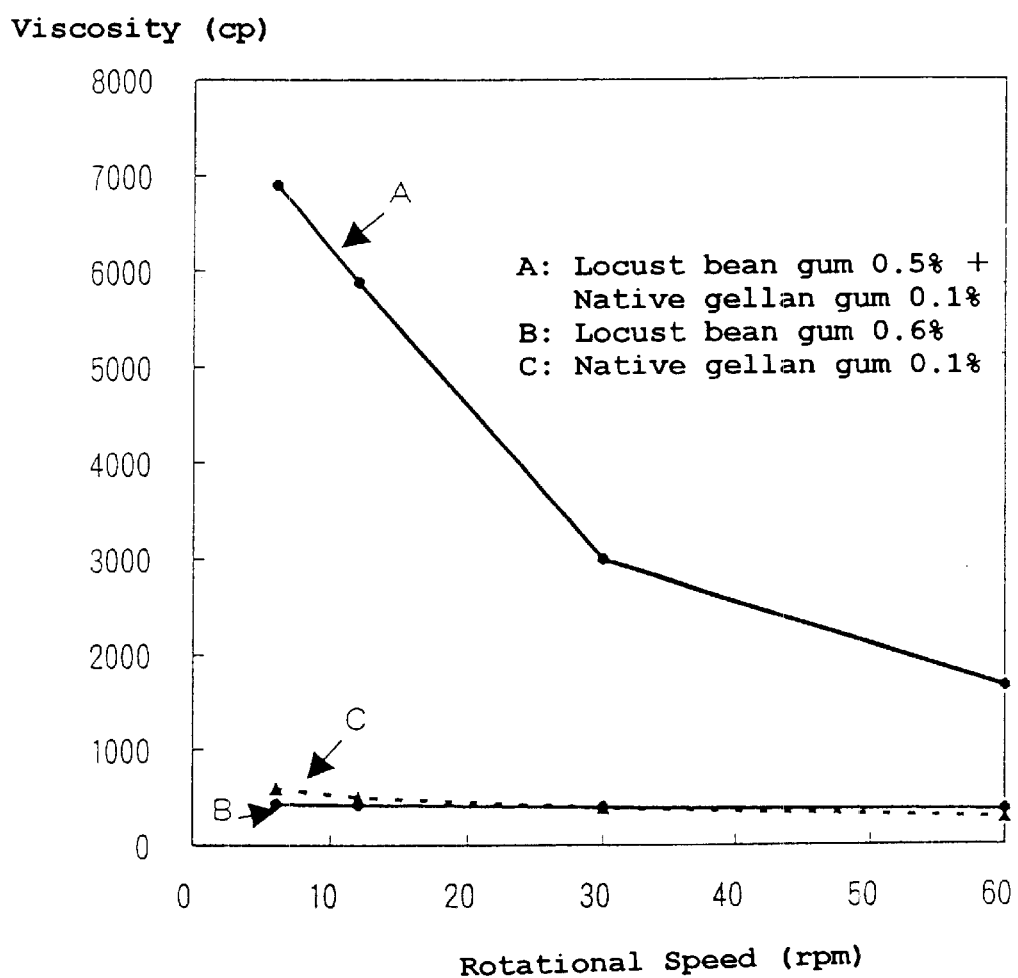

To 50 g of water was added 0.1 g of native gellan gum, and the mixture was heated for dissolving at 80° C. for 10 minutes. Separately, 0.5 g of locust bean gum was placed in 50 g of water and heated at 80° C. for 10 minutes. The two solutions were admixed and the viscosity of the combined solution was measured. As shown in FIG. 10, the lower the rotational speed was, the higher was the viscosity reading, and a viscosity value of as high as 6900 cps was recorded at the rotational speed of 6 rpm. This solution showed no evidence of gelation at all.

Figure 11:
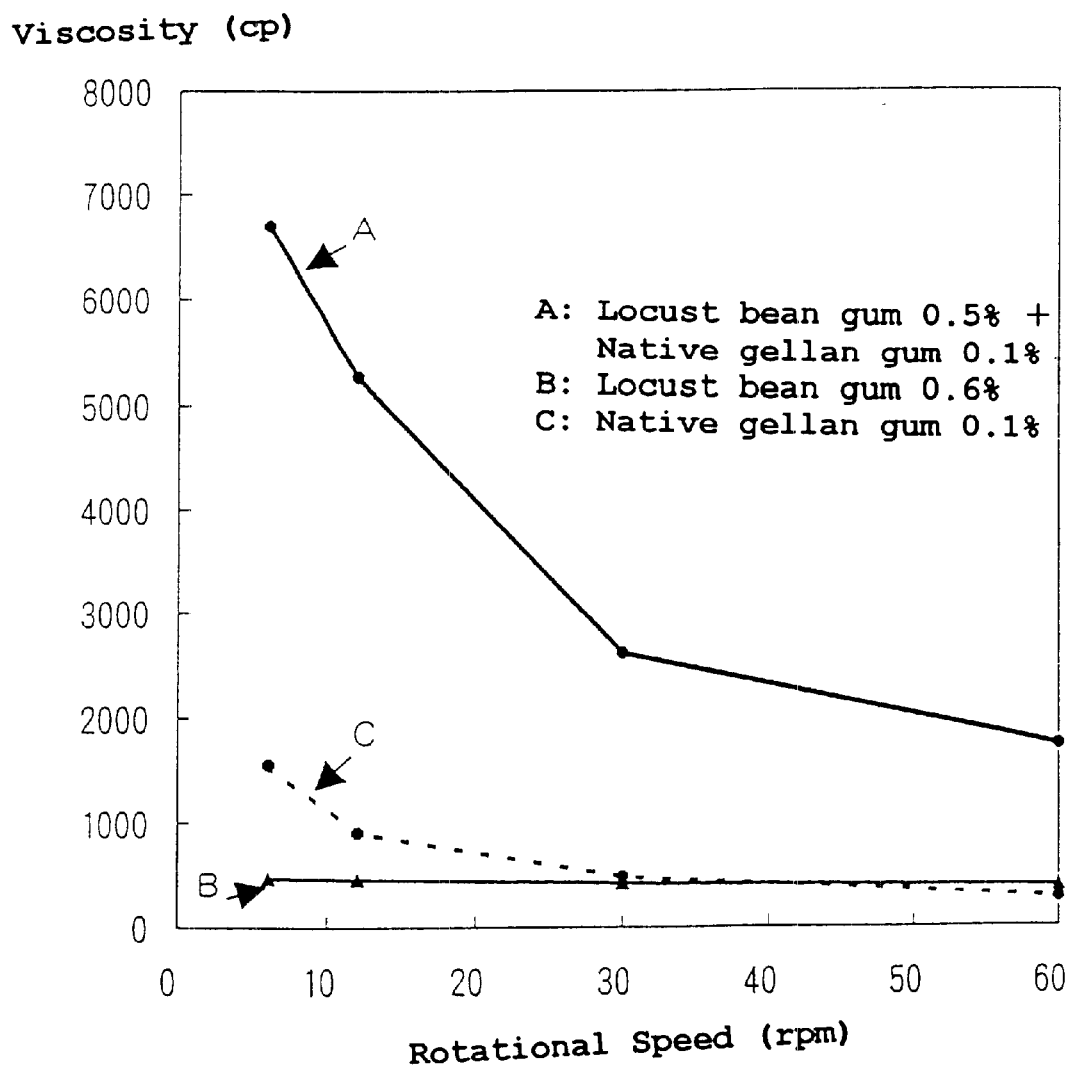

Furthermore, as in Experiment Example (7-2), the solutions adjusted to pH 3.5 in advance were admixed and the viscosity of the combined solution was measured. As shown in FIG. 11, the lower the rotational speed was, the higher was the viscosity reading, and a high viscosity of as high as 6700 cps was recorded at the rotational speed of 6 rpm. This solution showed no gelation at all.

As controls, in the respective cases mentioned above, the viscosity of a 0.1 wt. % solution of native gellan gum alone and that of a 0.6 wt. % solution of locust bean gum alone were respectively measured but neither showed sufficient viscosity.

Experiment Example (7-6)

Figure 12:
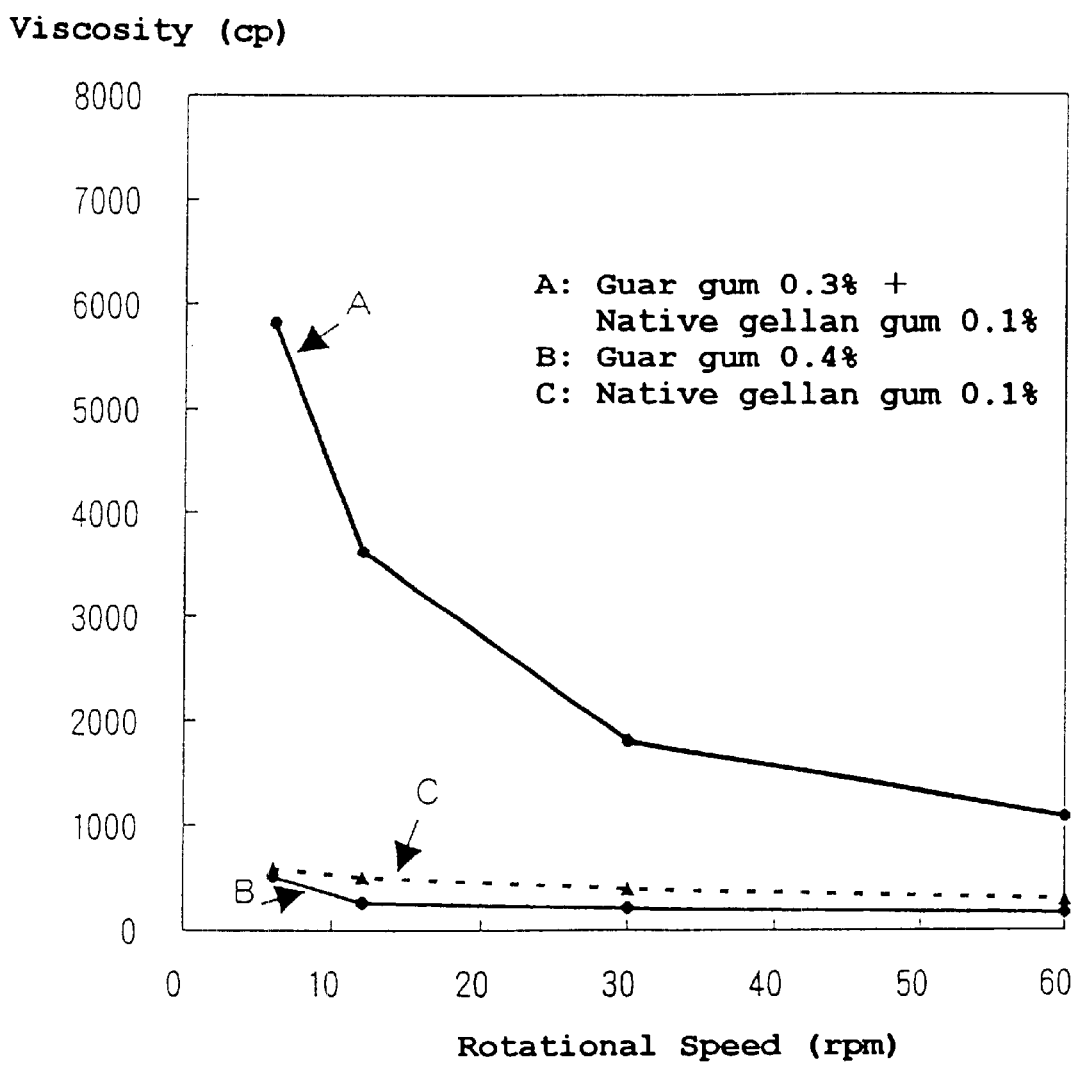

To 50 g of water was added 0.1 g of native gellan gum, and the mixture was heated for dissolving at 80° C. for 10 minutes. Separately, 0.3 g of guar gum was added to 50 g of water and heated for dissolving at 80° C. for 10 minutes. The viscosity of the combined solution was measured. As shown in FIG. 12, the lower the rotational speed was, the higher was the viscosity reading, and a high viscosity of 5820 cps was recorded at the rotational speed of 6 rpm. This solution showed no gelation at all.

Figure 13:
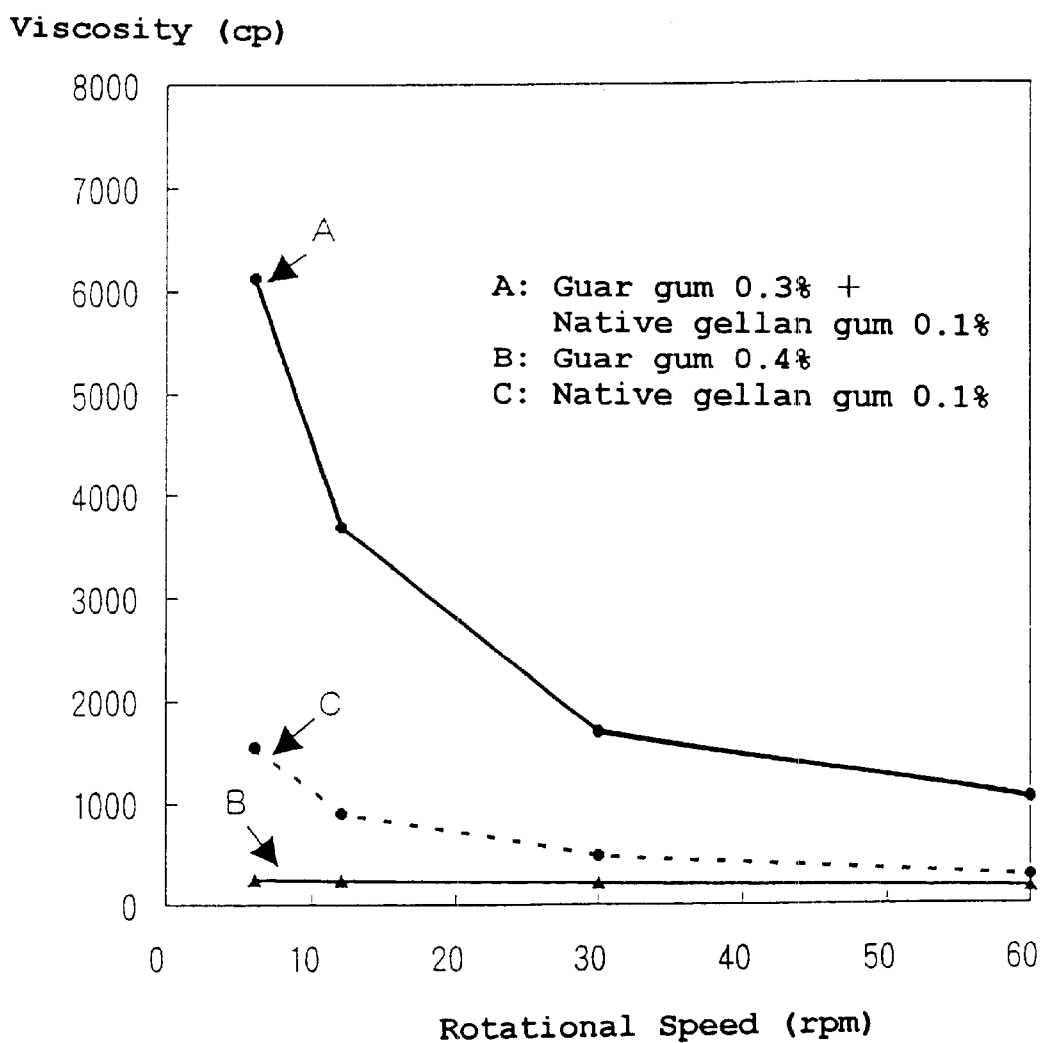

Moreover, as in Experiment Example (7-2), the solutions adjusted to pH 3.5 in advance were admixed and the viscosity of the combined solution was measured. As shown in FIG. 13, the lower the rotational speed was, the higher was the viscosity reading and a high viscosity of 6120 cps was recorded at the rotational speed of 6 rpm. This solution did not gel at all.

As controls, in the respective cases mentioned above, the viscosity of a 0.1 wt. % solution of native gellan gum alone and that of a 0.4 wt. % solution of guar gum alone were respectively measured but neither solution showed sufficient viscosity.

Experiment Example (7-7)

Figure 14:
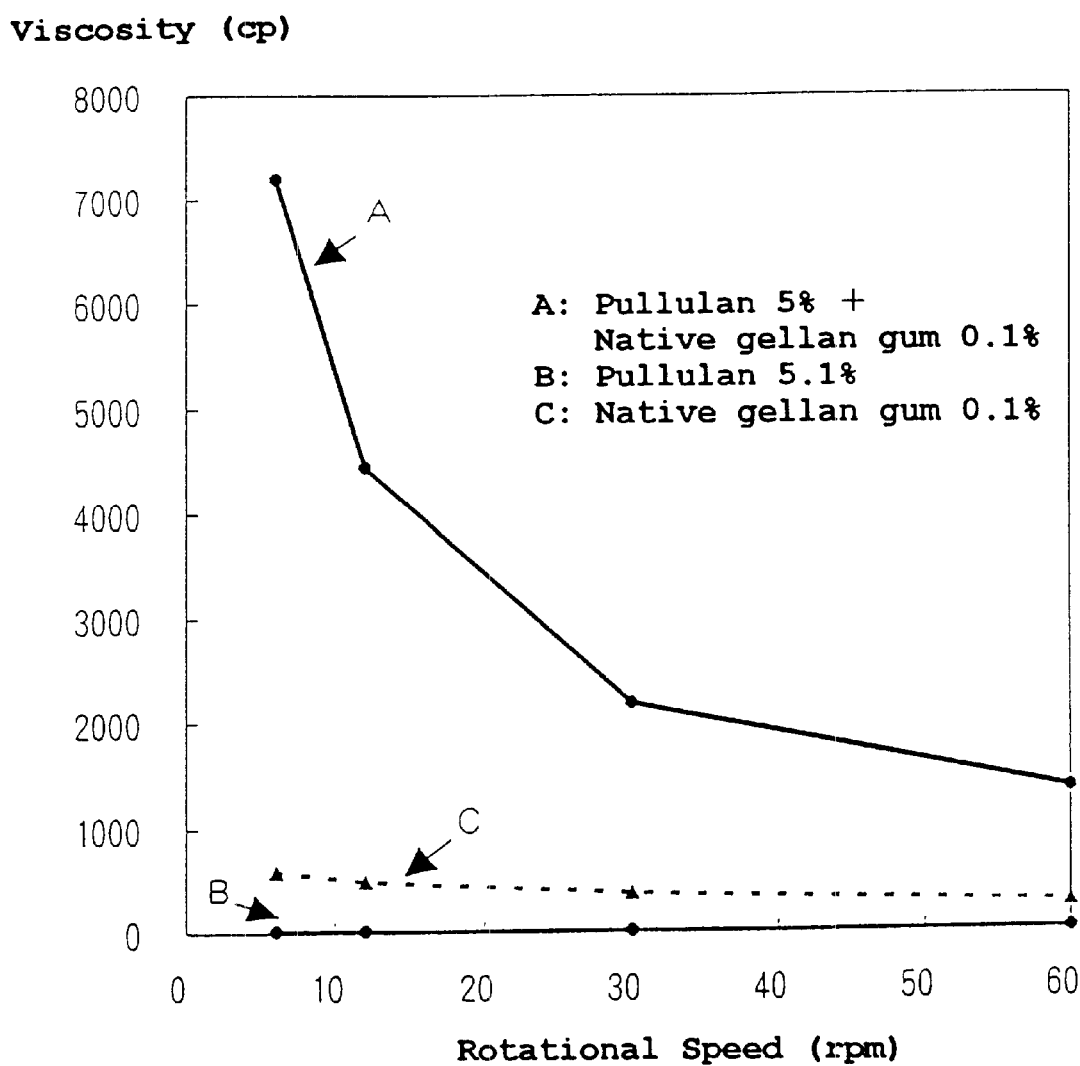

To 50 g of water was added 0.1 g of native gellan gum, and the mixture was heated for dissolving at 80° C. for 10 minutes. Separately, 5 g of pullulan was added to 50 g of water and heated for dissolving at 80° C. for 10 minutes. The viscosity of the combined solution was measured. As shown in FIG. 14, the lower the rotational speed was, the higher was the viscosity reading, and a high viscosity of 7020 cps was recorded at the rotational speed of 6 rpm. This solution showed no gelation at all.

Figure 15:
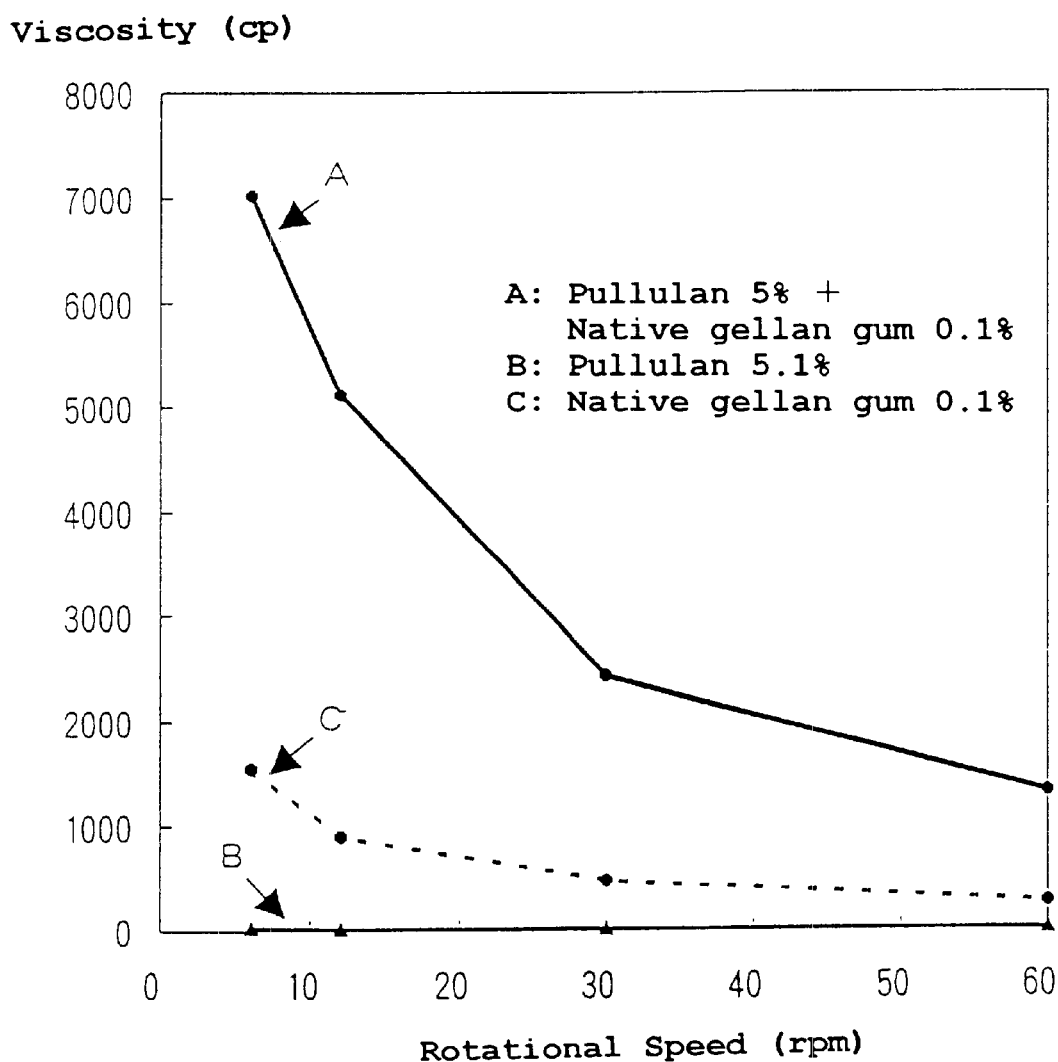

Moreover, as in Experiment Example (7-2), the solutions adjusted to pH 3.5 in advance were admixed and the viscosity of the combined solution was measured. As shown in FIG. 15, the lower the rotational speed was, the higher was the viscosity reading, and a high viscosity of 7200 cps was recorded at the rotational speed of 6 rpm. This solution did not gel at all.

As controls, in the respective cases mentioned above, the viscosity of a 0.1 wt. % solution of native gellan gum alone and that of a 5.1 wt. % solution of pullulan alone were respectively measured but neither solution showed sufficient viscosity.

Experiment Example (7-8)

Figure 16:
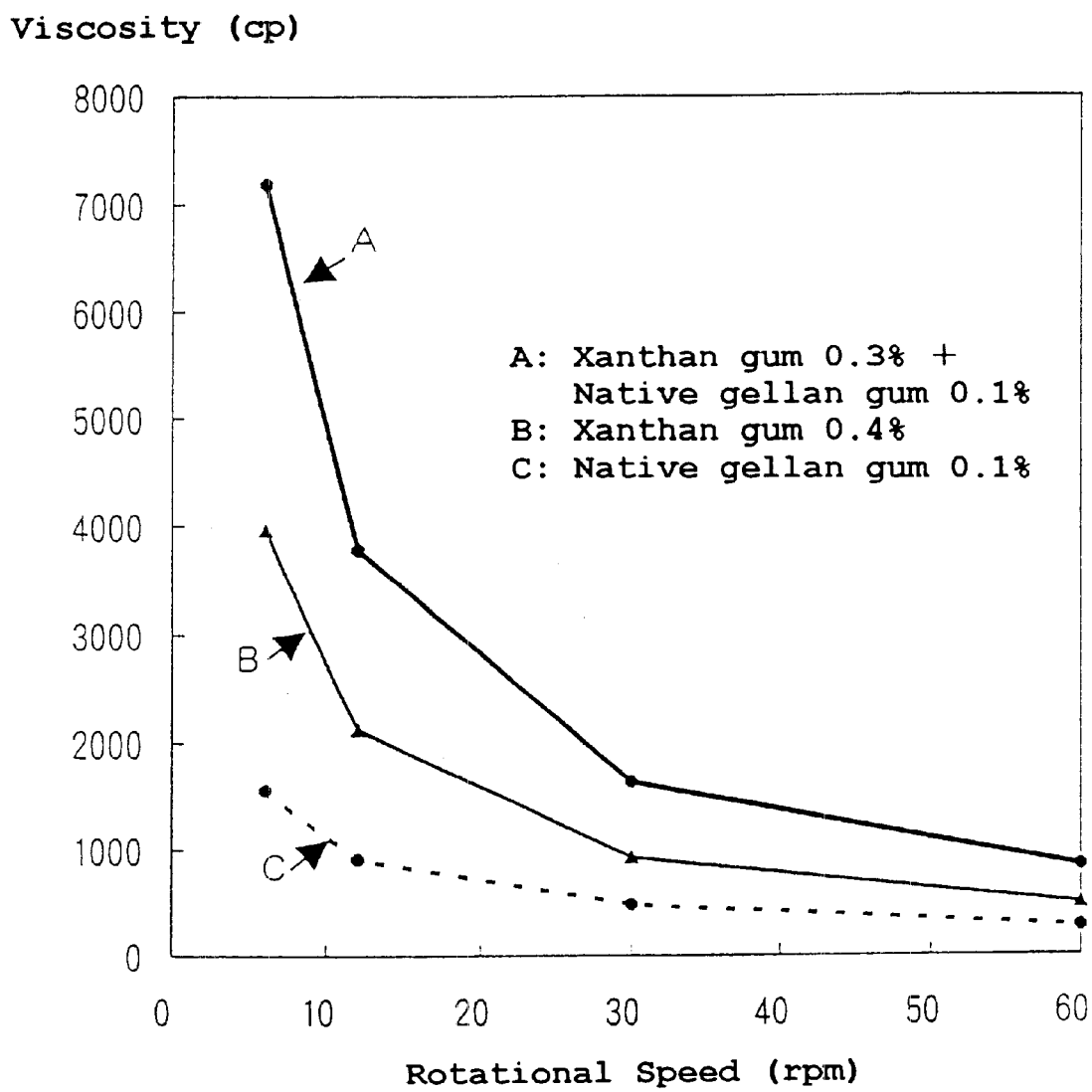

To 50 g of water was added 0.1 g of native gellan gum, and the mixture was heated for dissolving at 80° C. for 10 minutes and adjusted to pH 3.5. Separately, 0.3 g of xanthan gum was added to 50 g of water and heated for dissolving at 80° C. for 10 minutes and adjusted to pH 3.5. The two solutions were admixed and the viscosity of the combined solution was measured. As shown in FIG. 16, the lower the rotational speed was, the higher was the viscosity reading, and a high viscosity of 7180 cps was recorded at the rotational speed of 6 rpm. This solution showed no gelation at all.

As controls, in the respective cases mentioned above, the viscosity of a 0.1 wt. % solution of native gellan gum alone (pH 3.5) and that of a 0.4 wt. % solution of xanthan gum alone (pH 3.5) were respectively measured but neither solution showed sufficient viscosity.

Experiment Example (7-9)

Figure 17:
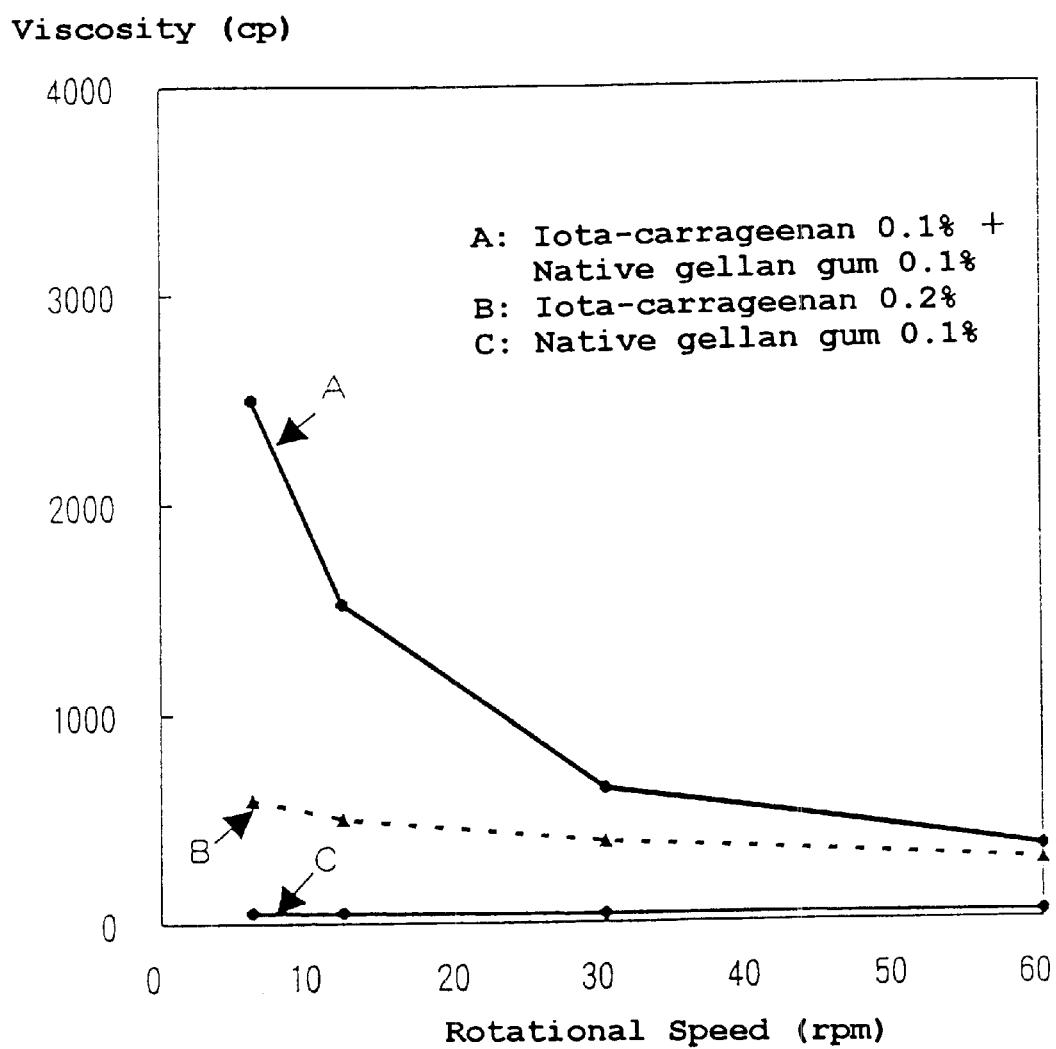

To 50 g of water was added 0.1 g of native gellan gum, and the mixture was heated for dissolving at 80° C. for 10 minutes. Separately, 0.1 g of iota-carrageenan was added to 50 g of water and heated for dissolving at 80° C. for 10 minutes. The viscosity of the combined solution was measured. As shown in FIG. 17, the lower the rotational speed was, the higher was the viscosity reading, and a-high viscosity of 2495 cps was recorded at the rotational speed of 6 rpm. This solution showed no gelation at all.

Figure 18:
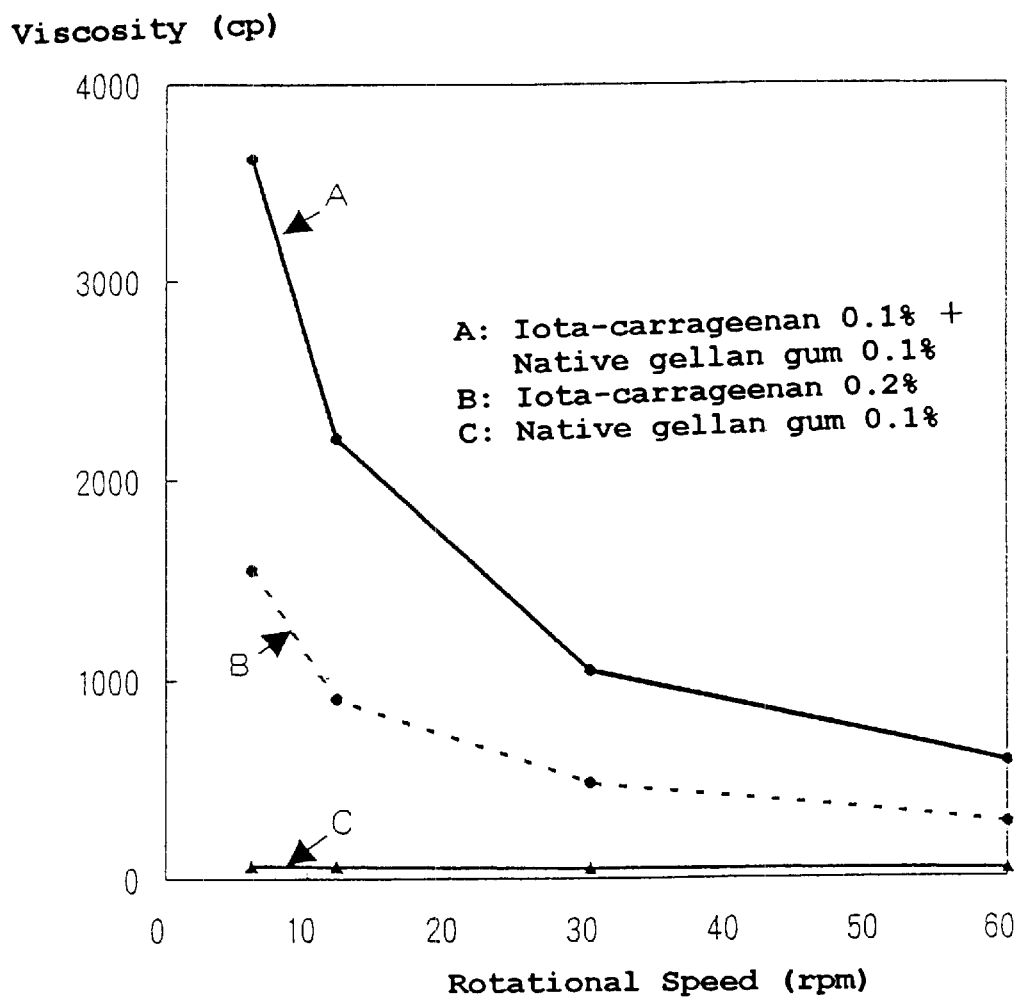

Moreover, as in Experiment Example (7-2), the solutions adjusted to pH 3.5 were prepared and admixed and the viscosity of the combined solution was measured. As shown in FIG. 18, the lower the rotational speed was, the higher was the viscosity reading, and a high viscosity of 3620 cps was recorded at the rotational speed of 6 rpm. This solution did not gel at all.

As controls, in the respective cases mentioned above, the viscosity of a 0.1 wt. % solution of native gellan gum alone and that of a 0.2 wt. % solution of iota-carrageenan alone were respectively measured but neither solution showed sufficient viscosity.

Experiment Example (7-10)

Figure 19:
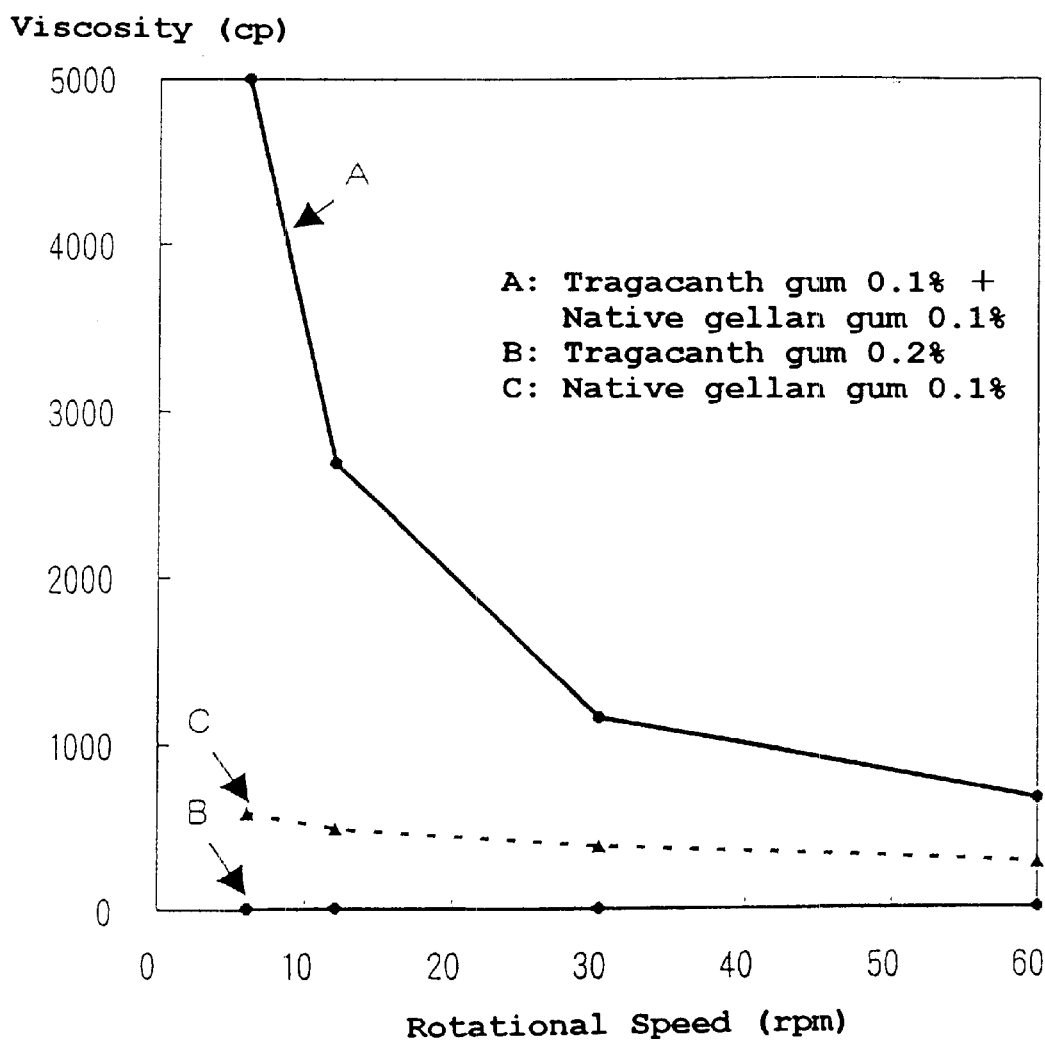

To 50 g of water was added 0.1 g of native gellan gum, and the mixture was heated for dissolving at 80° C. for 10 minutes. Separately, 0.1 g of tragacanth gum was added to 50 g of water and the mixture was heated for-dissolving at 80° C. for 10 minutes. The viscosity of the combined solution was measured. As shown in FIG. 19, the lower the rotational speed was, the higher was the viscosity reading, and a high viscosity of 5000 cps was recorded at the rotational speed of 6 rpm. This solution showed no gelation at all.

Figure 20:
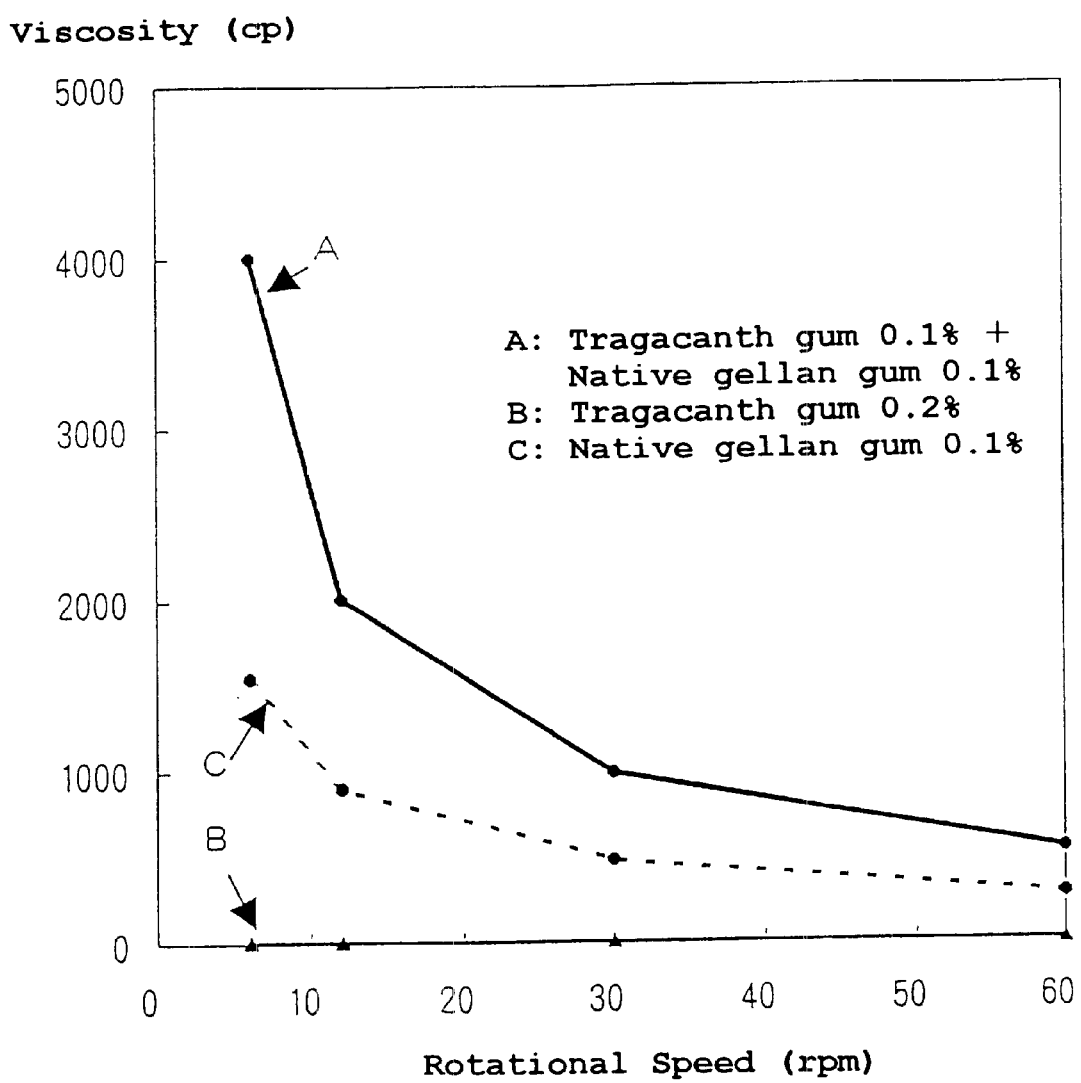

Moreover, as in Experiment Example (7-2), the solutions adjusted to pH 3.5 in advance were admixed and the viscosity of the combined solution was measured. As shown in FIG. 20, the lower the rotational speed was, the higher was the viscosity reading, and a high viscosity of 4000 cps was recorded at the rotational speed of 6 rpm. This solution did not gel at all.

As controls, in the respective cases mentioned above, the viscosity of a 0.1 wt. % solution of native gellan gum alone and that of a 0.2 wt. % solution of tragacanth gum alone were respectively measured but neither solution showed sufficient viscosity.

Experiment Example (7-11)

Figure 21:
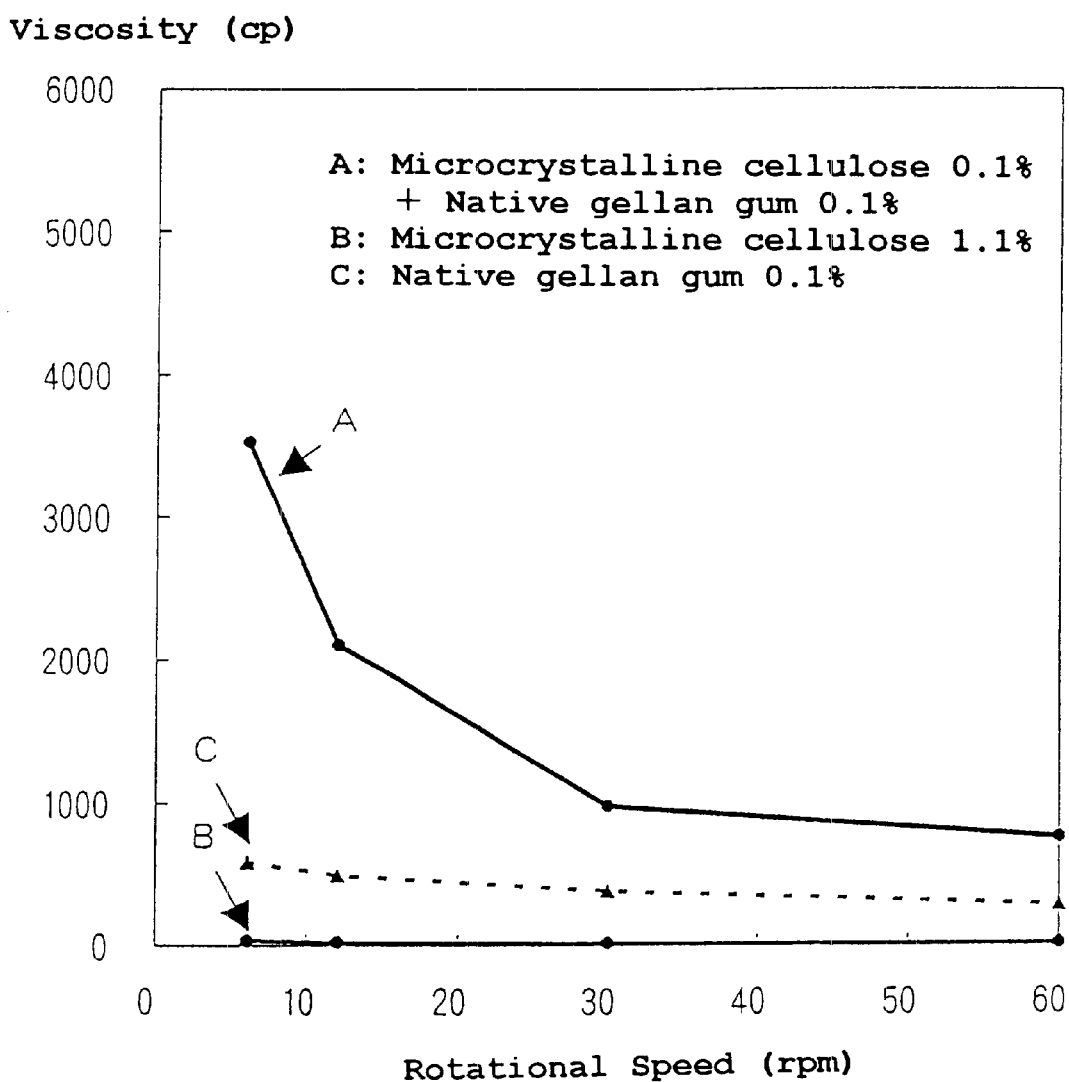

To 50 g of water was added 0.1 g of native gellan gum, and the mixture was heated at 80° C. for 10 minutes. Separately, 1 g of microcrystalline cellulose [Ceollus (trademark) SC-42, Asahi Chemical Industry] was added to 50 g of water and heated for dissolving at 80° C. for 10 minutes. The viscosity of the combined solution was measured. As shown in FIG. 21, the lower the rotational speed was, the higher was the viscosity reading, and a high viscosity of 3525 cps was recorded at the rotational speed of 6 rpm. This solution showed no gelation at all.

Figure 22:
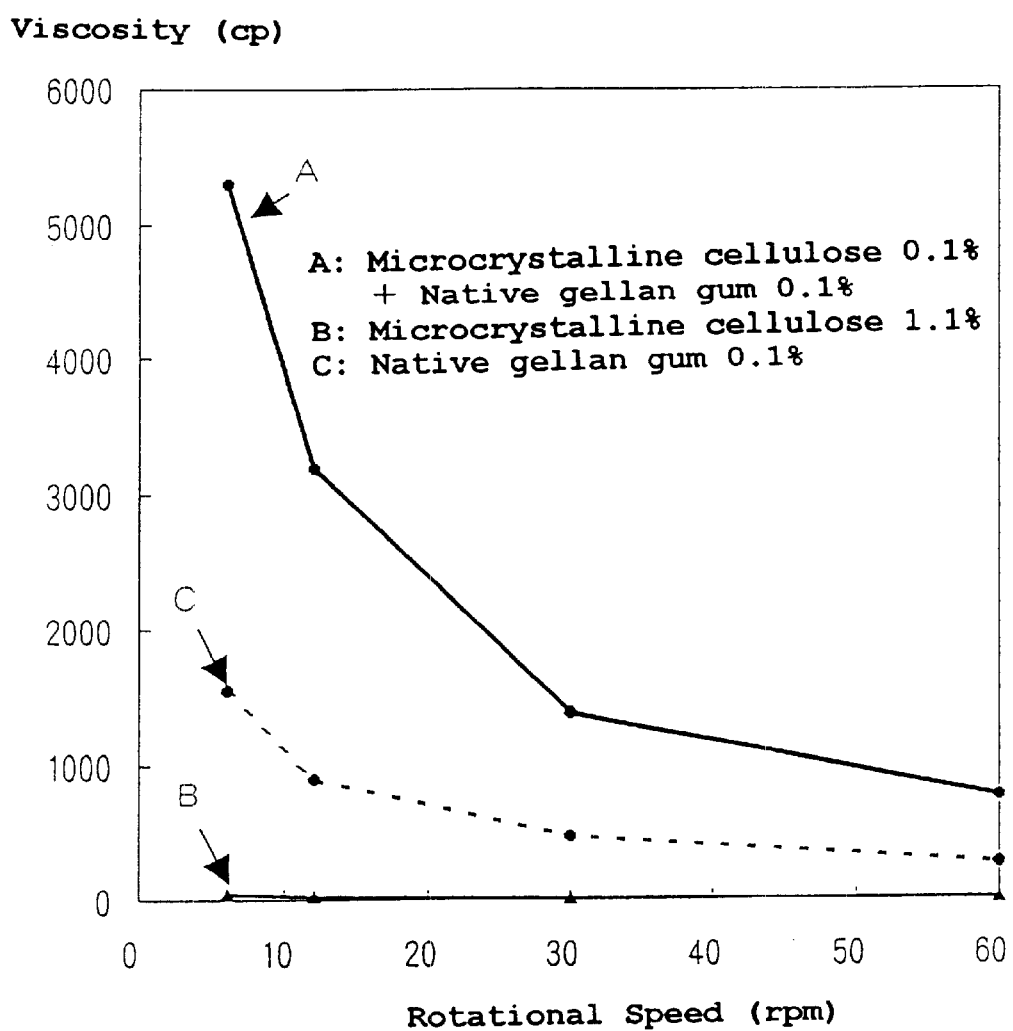

Moreover, as in Experiment Example (7-2), the corresponding solutions adjusted to pH 3.5 were prepared and admixed and the viscosity of the combined solution was measured. As shown in FIG. 22, the lower the rotational speed was, the higher was the viscosity reading, and a high viscosity of 5300 cps was recorded at the rotational speed of 6 rpm. This solution did not gel at all.

As controls, in the respective cases mentioned above, the viscosity of a 0.1 wt. % solution of native gellan gum alone and that of a 1.1 wt. % solution of microcrystalline cellulose alone were respectively measured but neither solution showed sufficient viscosity.

Experiment Example (7-12)

Figure 23:
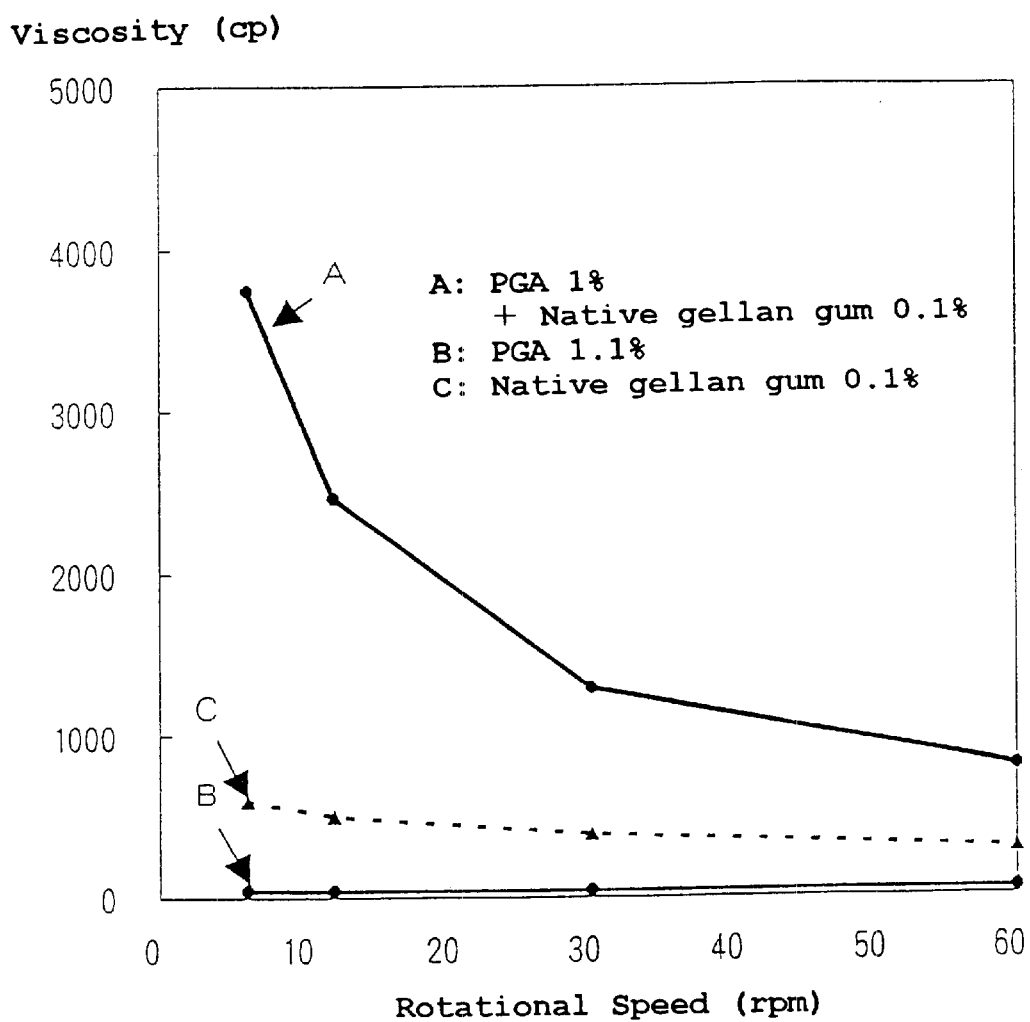

To 50 g of water was added 0.1 g of native gellan gum, and the mixture was heated for dissolving at 80° C. for 10 minutes. Separately, 1 g of PGA (propylene glycol alginate, Kibun Food-Chemifer) was added to 50 g of water and the mixture was heated for dissolving at 80° C. for 10 minutes and the viscosity of the combined solution was measured. As shown in FIG. 23, the lower the rotational speed was, the higher was the viscosity reading, and a high viscosity of 3750 cps was recorded at the rotational speed of 6 rpm. This solution showed no gelation at all.

Figure 24:
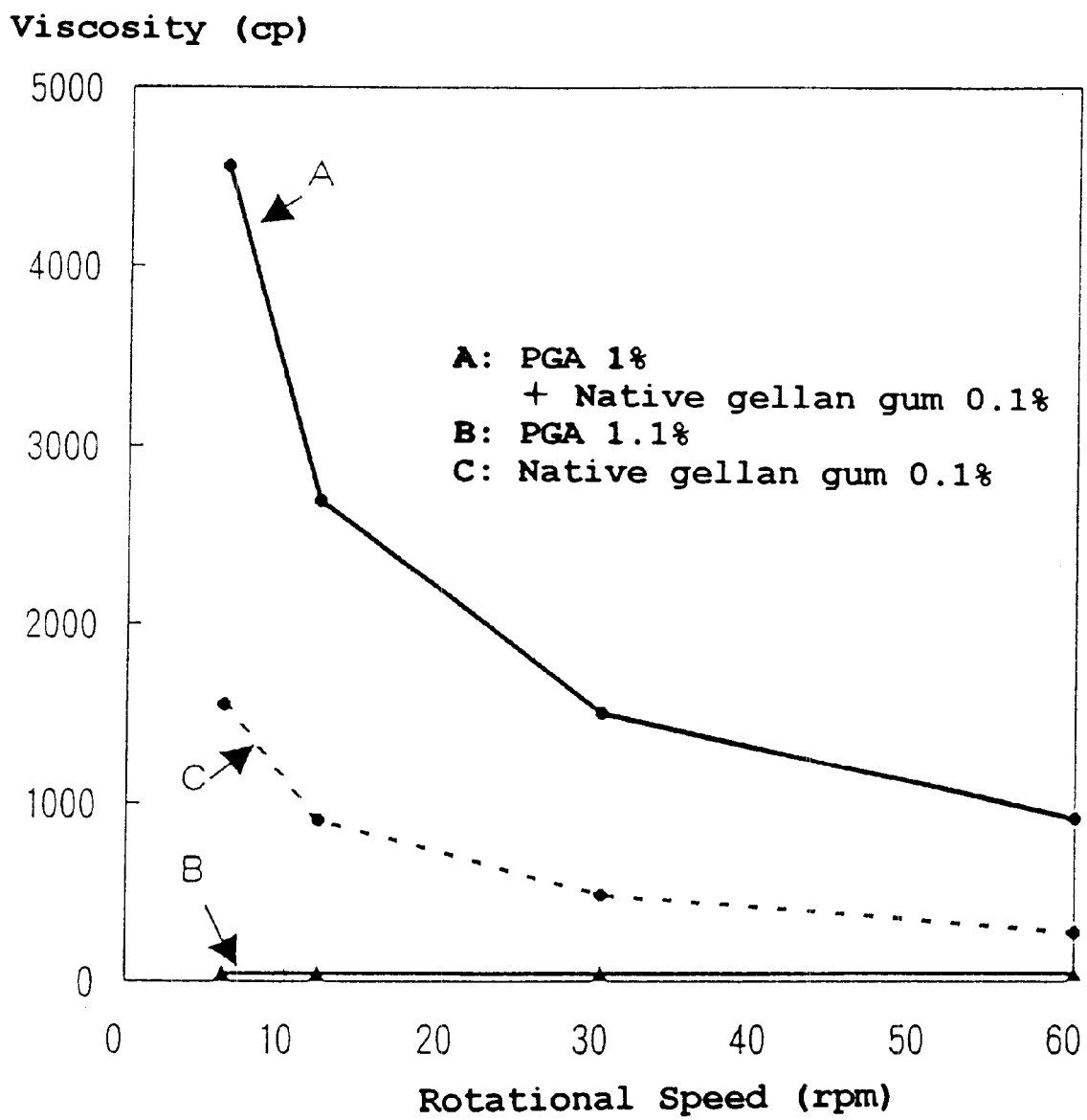

Moreover, as in Experiment Example (7-2), the solutions adjusted to pH 3.5 in advance were admixed and the viscosity of the combined solution was measured. As shown in FIG. 24, the lower the rotational speed was, the higher was the viscosity reading, and a high viscosity of 4560 cps was recorded at the rotational speed of 6 rpm. This solution did not gel at all.

As controls, in the respective cases mentioned above, the viscosity of a 0.1 wt. % solution of native gellan gum alone and that of a 1.1 wt. % solution of PGA alone were respectively measured but neither solution showed sufficient viscosity.

Experiment Example (7-13)

Figure 25:
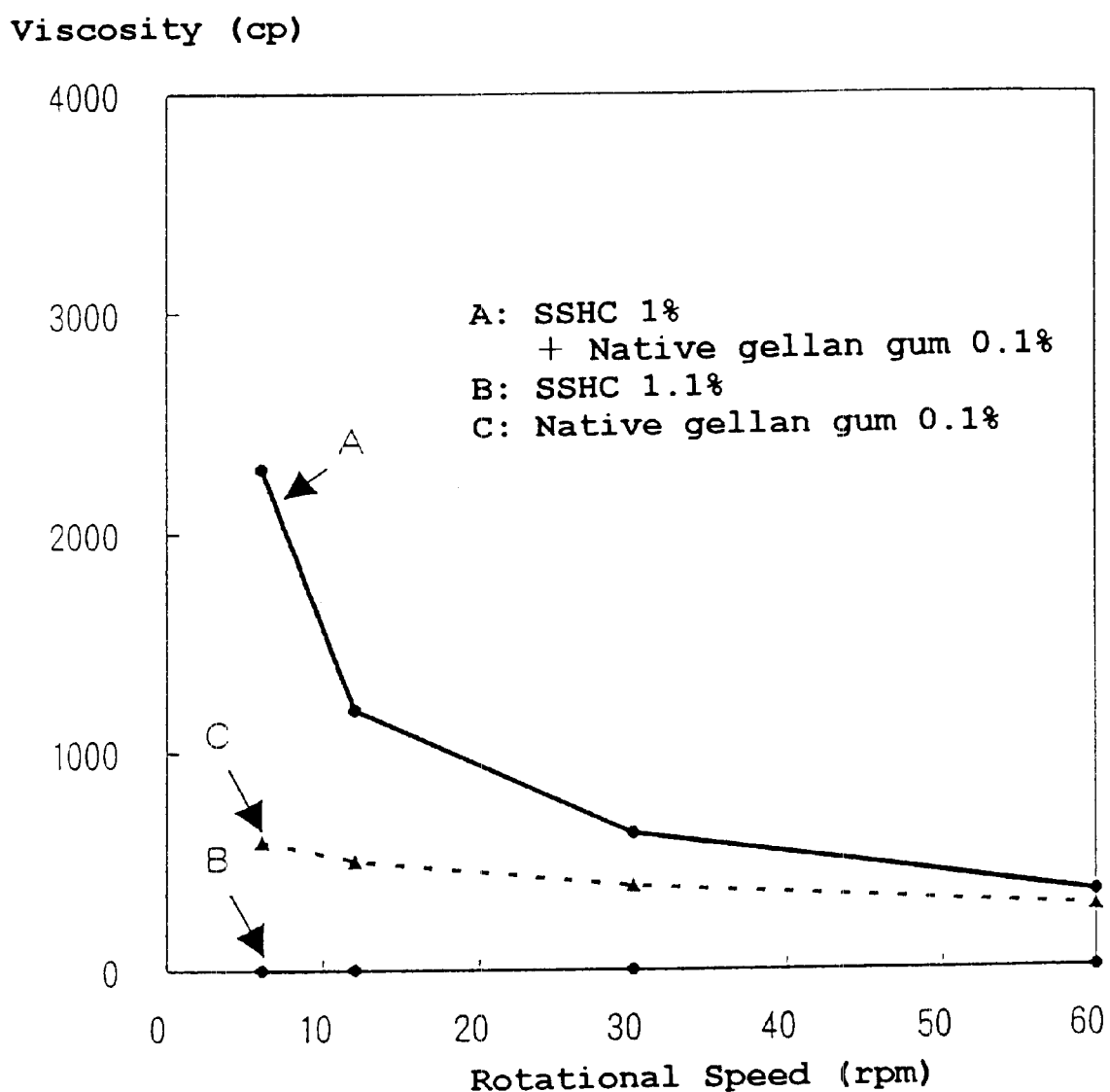

To 50 g of water was added 0.1 g of native gellan gum, and the mixture was heated for dissolving at 80 for 10 minutes. Separately, 1 g of SSHC (water-soluble soybean polysaccharide, Fuji Oil) was added to 50 g of water and heated for dissolving at 80° C. for 10 minutes. The viscosity of the combined solution was measured. As shown in FIG. 25, the lower the rotational speed was, the higher was the viscosity reading, and a high viscosity of 2295 cps was recorded at the rotational speed of 6 rpm. This solution showed no gelation at all.

Figure 26:
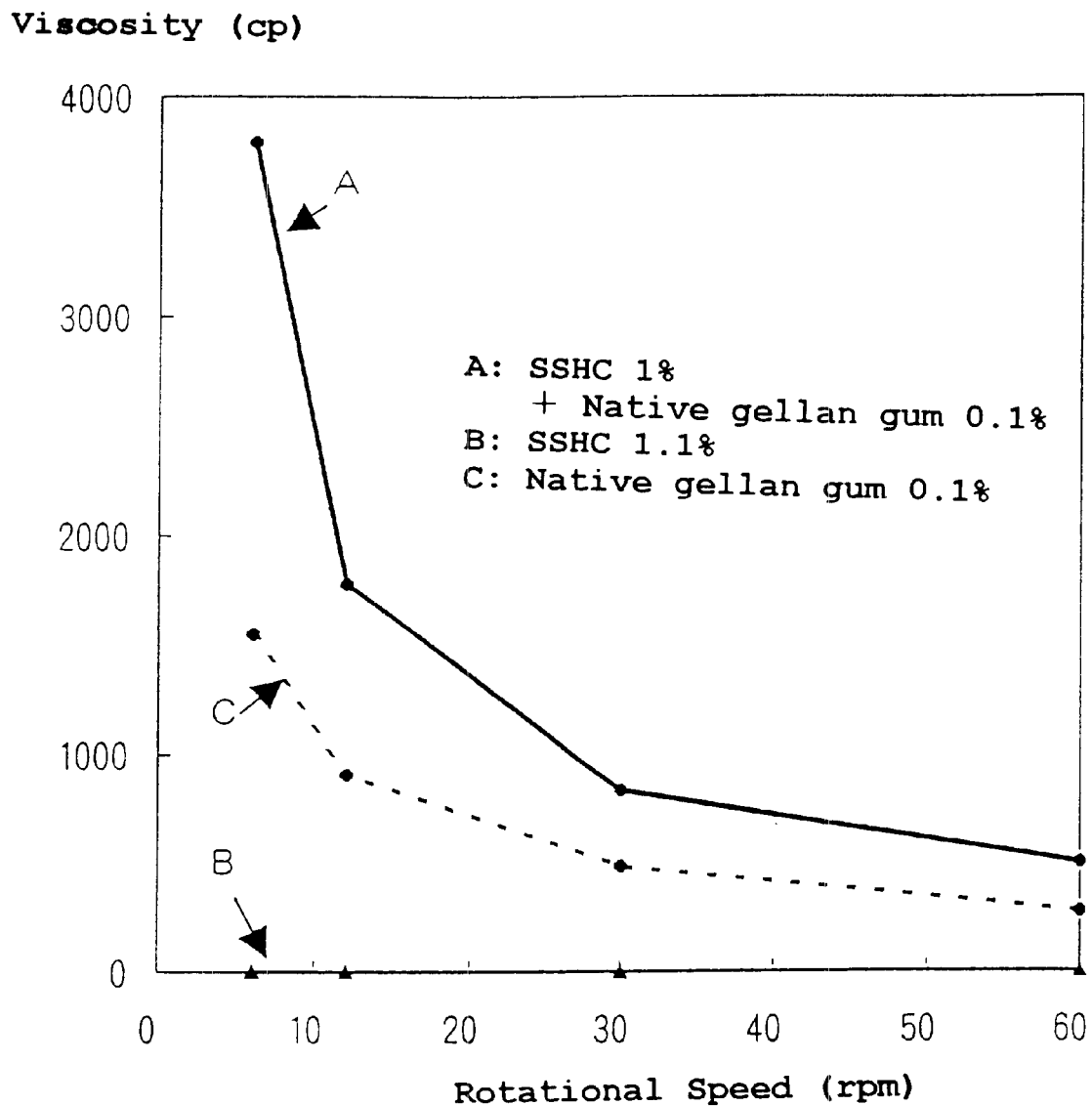

Moreover, as in Experiment Example (7-2), the solutions adjusted to pH 3.5 in advance were admixed and the viscosity of the combined solution was measured. As shown in FIG. 26, the lower the rotational speed was, the higher was the viscosity reading, and a high viscosity of 3790 cps was recorded at the rotational speed of 6 rpm. This solution did not gel at all.

As controls, in the respective cases mentioned above, the viscosity of a 0.1 wt. % solution of native gellan gum alone and that of a 1.1 wt. % solution of SSHC alone were respectively measured but neither solution showed sufficient viscosity.

Experiment Example (7-14)

Figure 27:
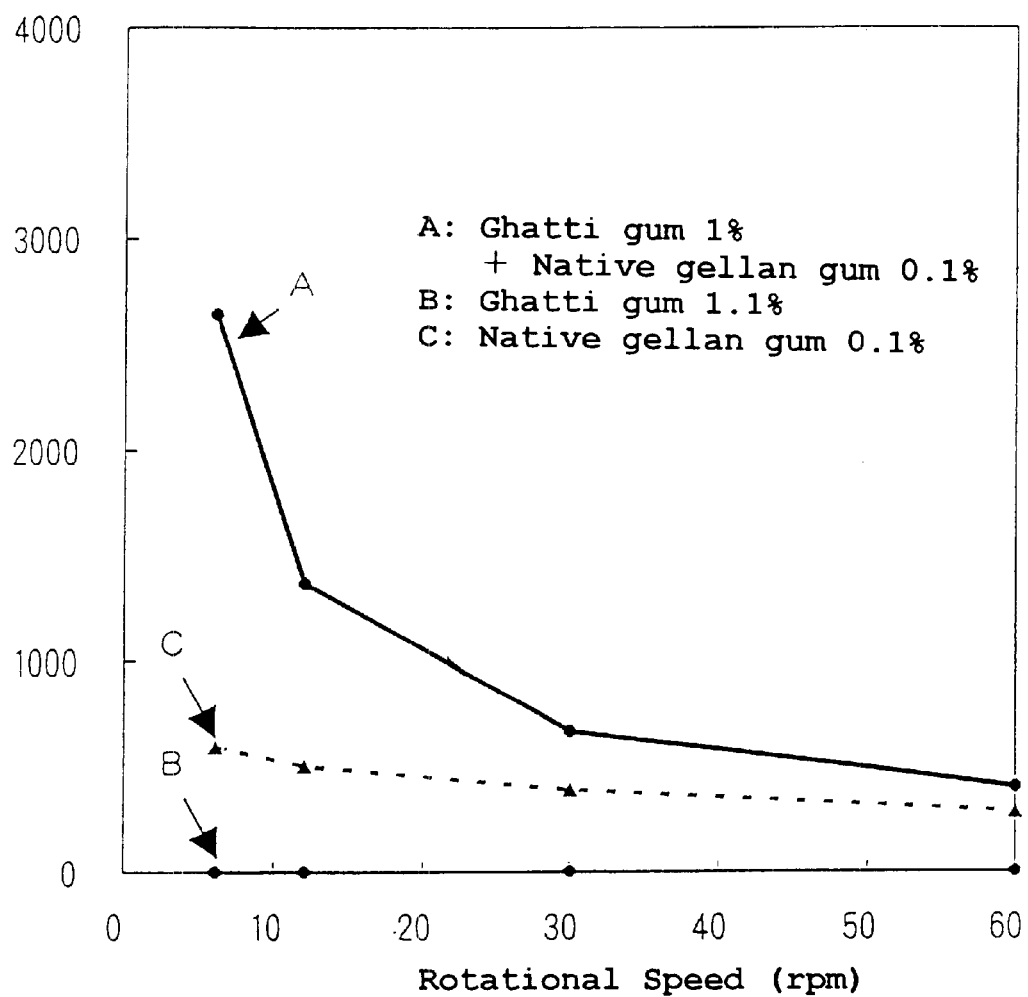

To 50 g of water was added 0.1 g of native gellan gum, and the mixture was heated for dissolving at 80° C. for 10 minutes. Separately, 1 g of ghatti gum was added to 50 g of water and heated for dissolving at 80° C. for 10 minutes, and the viscosity of the combined solution was measured. As shown in FIG. 27, the lower the rotational speed was, the higher was the viscosity reading, and a high viscosity of 2640 cps was recorded at the rotational speed of 6 rpm. This solution showed no gelation at all.

Figure 28:
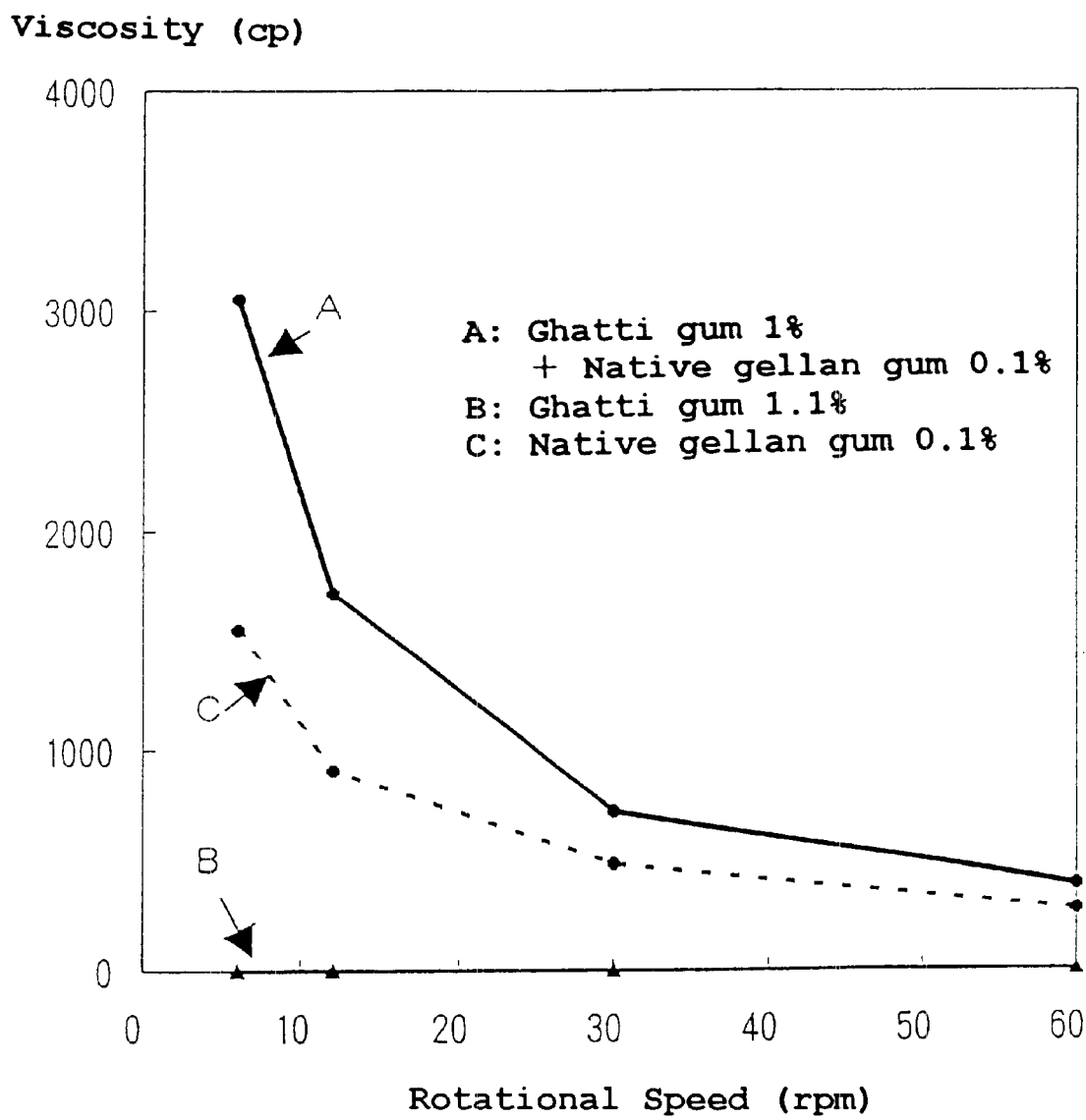

Moreover, as in Experiment Example (7-2), the solutions adjusted to pH 3.5 in advance were admixed and the viscosity of the combined solution was measured. As shown in FIG. 28, the lower the rotational speed was, the-higher was the viscosity reading, and a high viscosity of 3050 cps was recorded at the rotational speed of 6 rpm. This solution did not gel at all.

As controls, in the respective cases mentioned above, the viscosity of a 0.1 wt. % solution of native gellan gum alone and that of a 1.1 wt. % solution of ghatti gum alone were respectively measured but neither solution showed sufficient viscosity.

Experiment Example (7-15)

Figure 29:
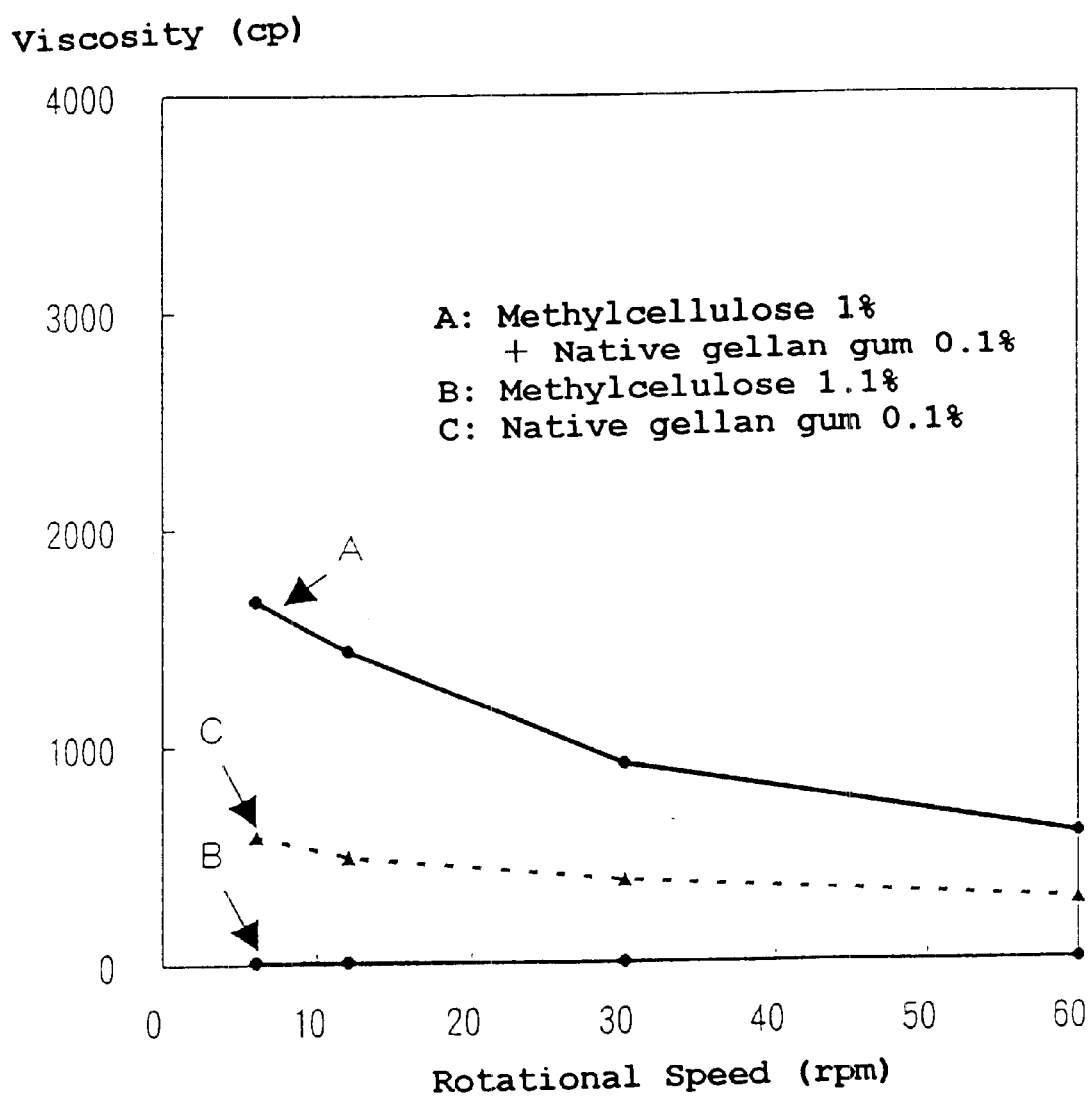

To 50 g of water was added 0.1 g of native gellan gum, and the mixture was heated for dissolving at 80° C. for 10 minutes. Separately, 1 g of methylcellulose (Sanshou) was added to 50 g of water and heated for dissolving at 80° C. for 10 minutes, and the viscosity of the combined solution was measured. As shown in FIG. 29, the lower the rotational speed was, the higher was the viscosity reading, and a high viscosity of 1675 cps was recorded at the rotational speed of 6 rpm. This solution showed no gelation at all.

Figure 30:
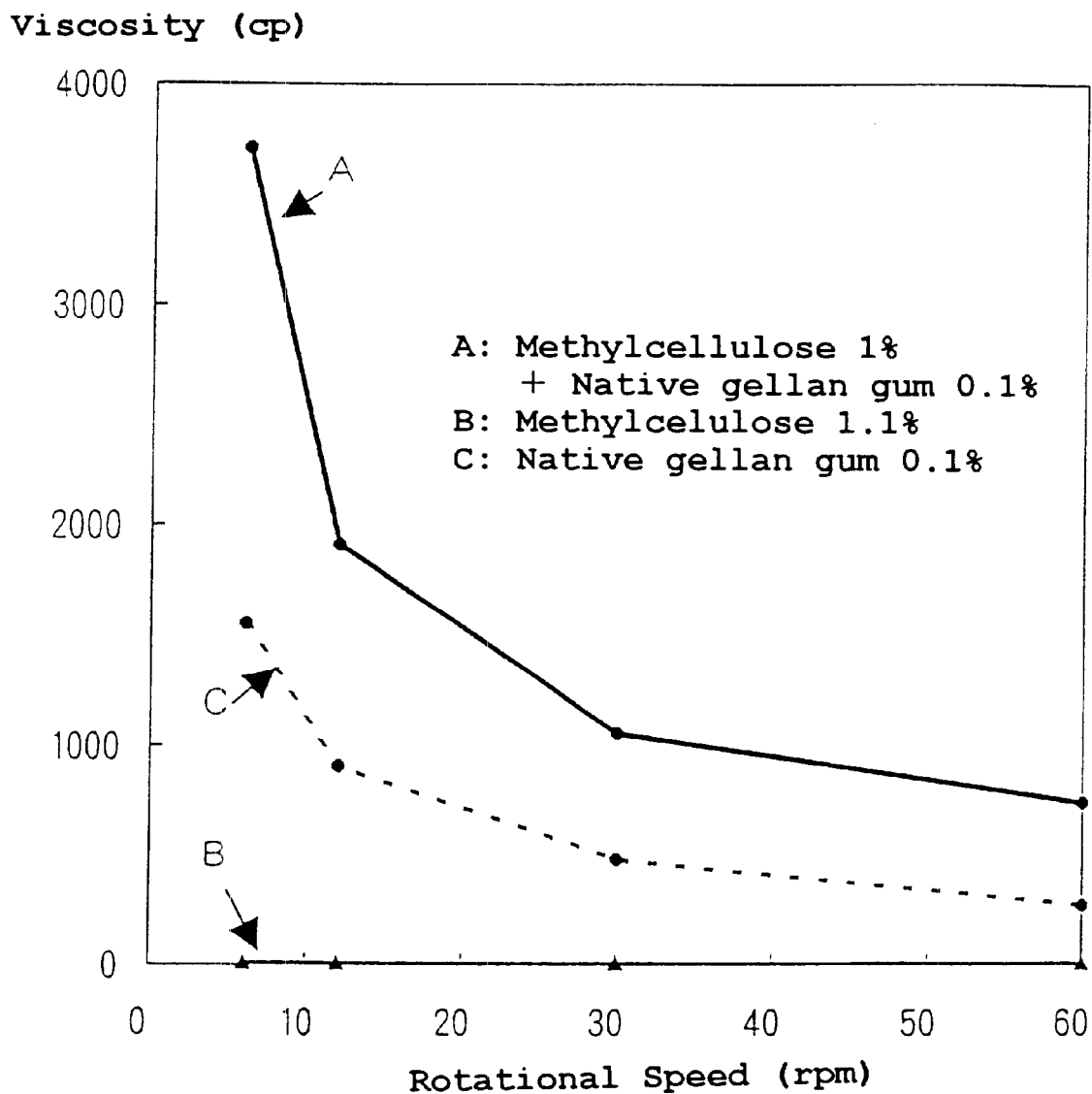

Moreover, as in Experiment Example (7-2), the solutions adjusted to pH 3.5 were prepared and admixed and the viscosity of the combined solution was measured. As shown in FIG. 30, the lower the rotational speed was, the higher was the viscosity reading and a high viscosity of 3710 cps was recorded at the rotational speed of 6 rpm. This solution did not gel at all.

As controls, in the respective cases mentioned above, the viscosity of a 0.1 wt. % solution of native gellan gum alone and that of a 1.1 wt. % solution of methylcellulose alone were respectively measured but neither solution showed sufficient viscosity.

Experiment Example (7-16)

Figure 31:
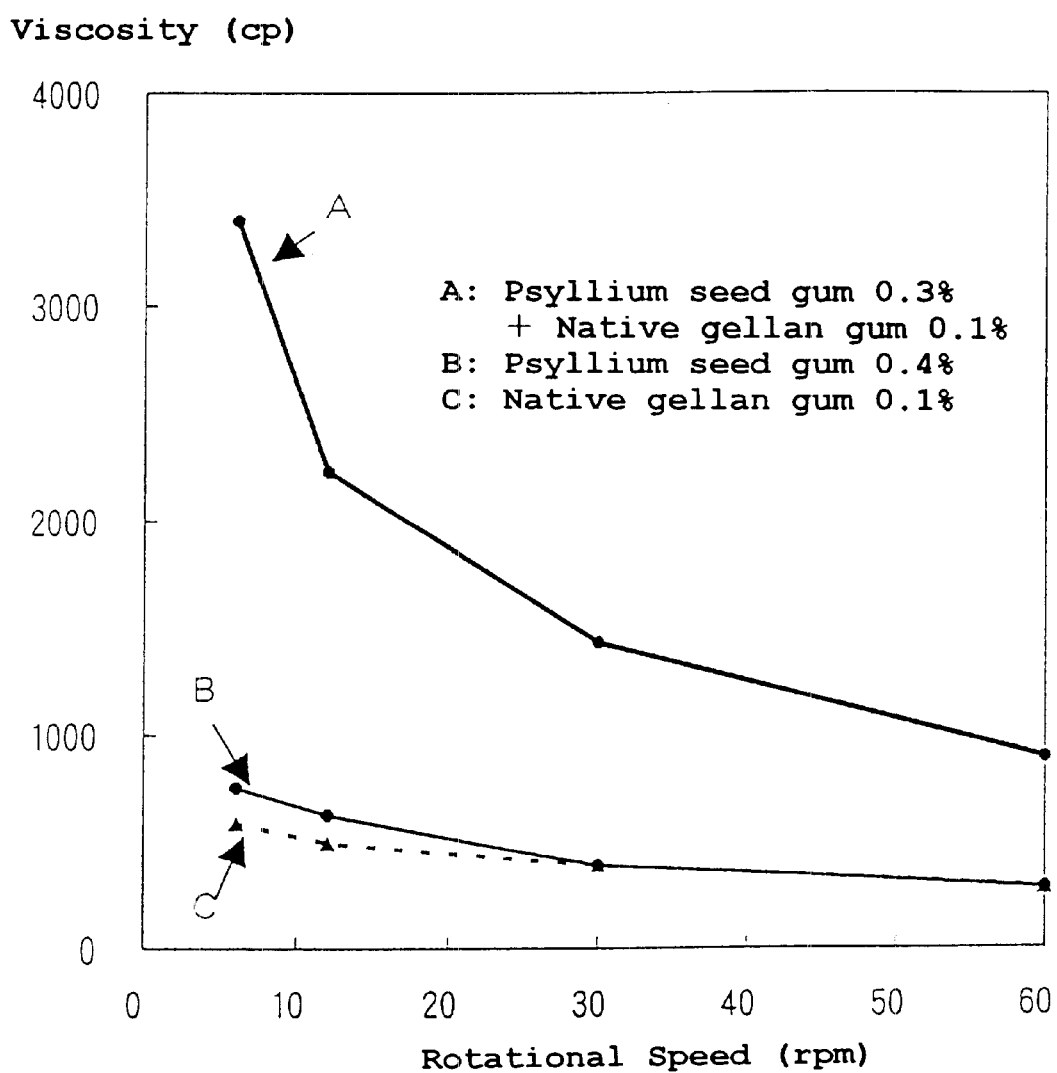

To 50 g of water was added 0.1 g of native gellan gum, and the mixture was heated for dissolving at 80° C. for 10 minutes. Separately, 0.3 g of psyllium seed gum was added to 50 g of water and heated for dissolving at 80° C. for 10 minutes, and the viscosity of the combined solution was measured. As shown in FIG. 31, the lower the rotational speed was, the higher was the viscosity reading, and a high viscosity of 3400 cps was recorded at the rotational speed of 6 rpm. This solution showed no gelation at all.

Figure 32:
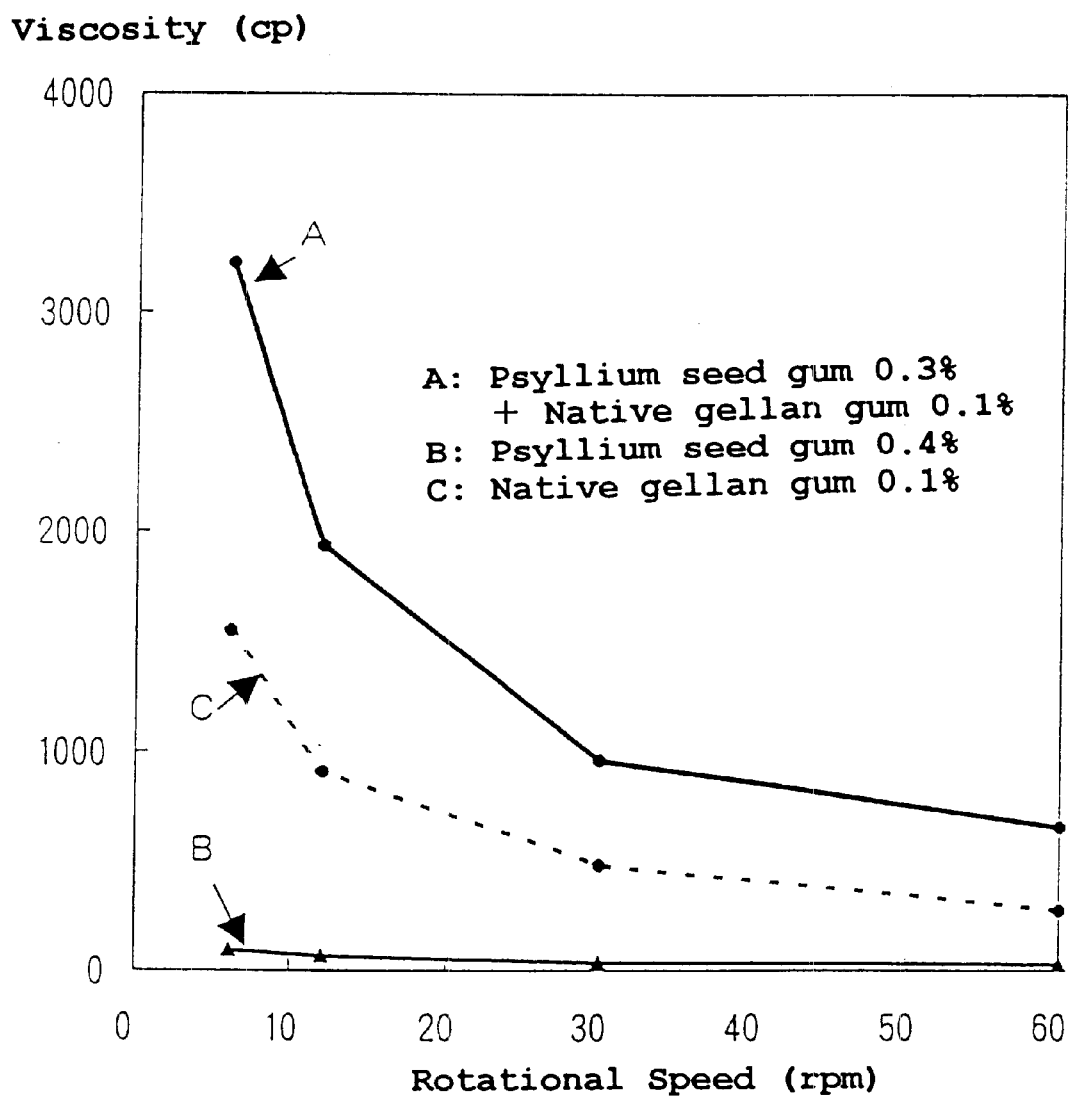

Moreover, as in Experiment Example (7-2), the solutions adjusted to pH 3.5 were prepared and admixed and the viscosity of the combined solution was measured. As shown in FIG. 32, the lower the rotational speed was, the higher was the viscosity reading, and a high viscosity of 3225 cps was recorded at the rotational speed of 6 rpm. This solution did not gel at all.

As controls, in the respective cases mentioned above the viscosity of a 0.1 wt. % solution of native gellan gum alone and that of a 0.4 wt. % solution of psyllium seed gum alone were respectively measured but neither solution showed sufficient viscosity.

Experiment Example (7-17)

Figure 33:
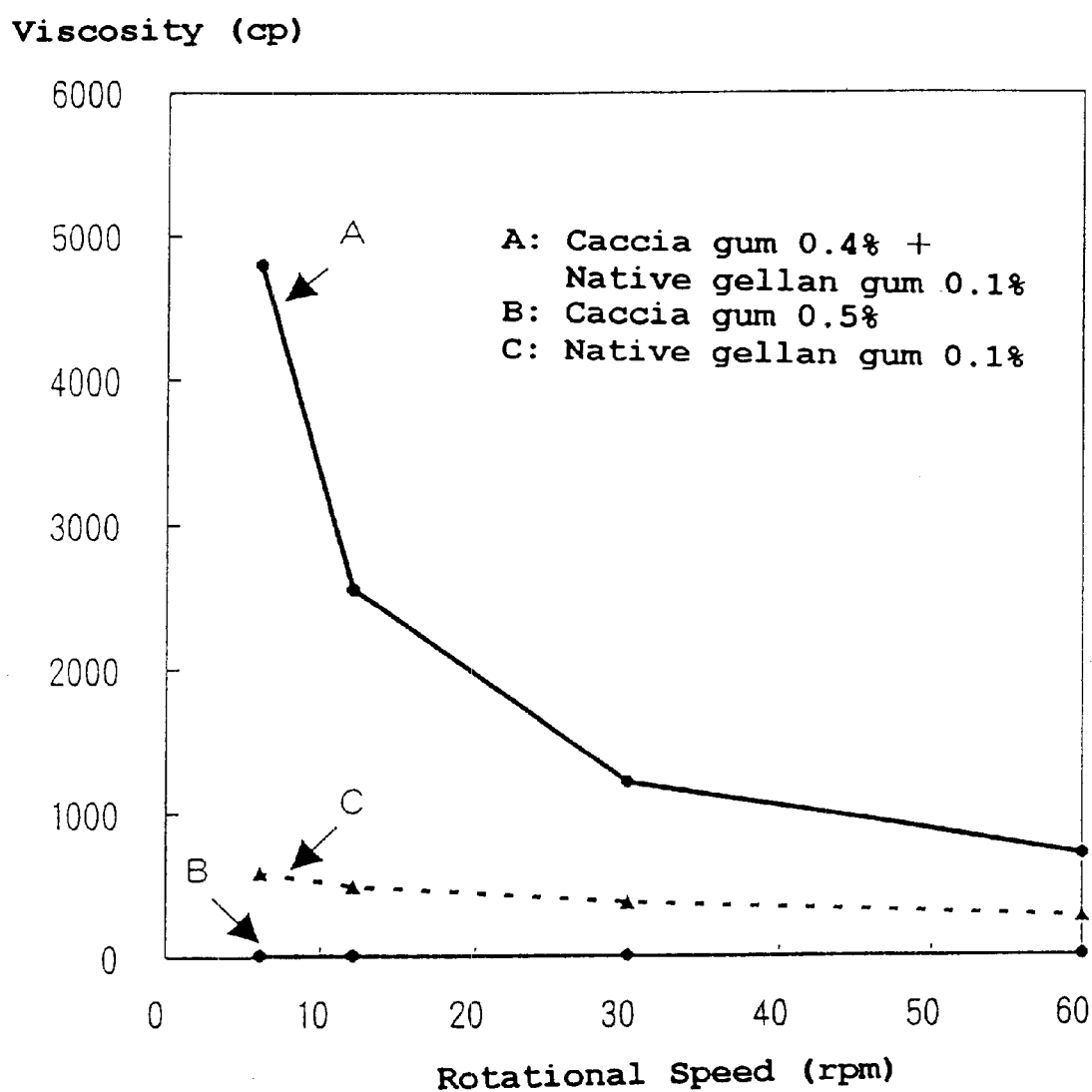

To 50 g of water was added 0.1 g of native gellan gum, and the mixture was heated for dissolving at 80° C. for 10 minutes. Separately, 0.4 g of caccia gum was added to 50 g of water and heated for dissolving at 80 for 10 minutes. The viscosity of the combined solution was measured. As shown in FIG. 33, the lower the rotational speed was, the higher was the viscosity reading, and a high viscosity of 4800 cps was recorded at the rotational speed of 6 rpm. This solution showed no gelation at all.

As controls, in the respective cases mentioned above, the viscosity of a 0.1 wt. % solution of native gellan gum alone and that of a 0.5 wt. % solution of caccia gum alone were respectively measured but neither solution showed sufficient viscosity.

It is clear from the above experiment examples that as is native gellan gum, each of tamarind seed gum, tara gum, glucomannan, xanthan gum, locust bean gum, pullulan, guar gum, iota-carrageenan, tragacanth gum, microcrystalline cellulose, propylene glycol alginate, water-soluble soybean polysaccharide (SSHC), methylcellulose, caccia gum, and psyllium seed gum shows low viscosity when used alone but when any of them is used in combination with native gellan gum, its viscosity is remarkably increased synergistically.

Experiment Example (7-18)

Figure 34:
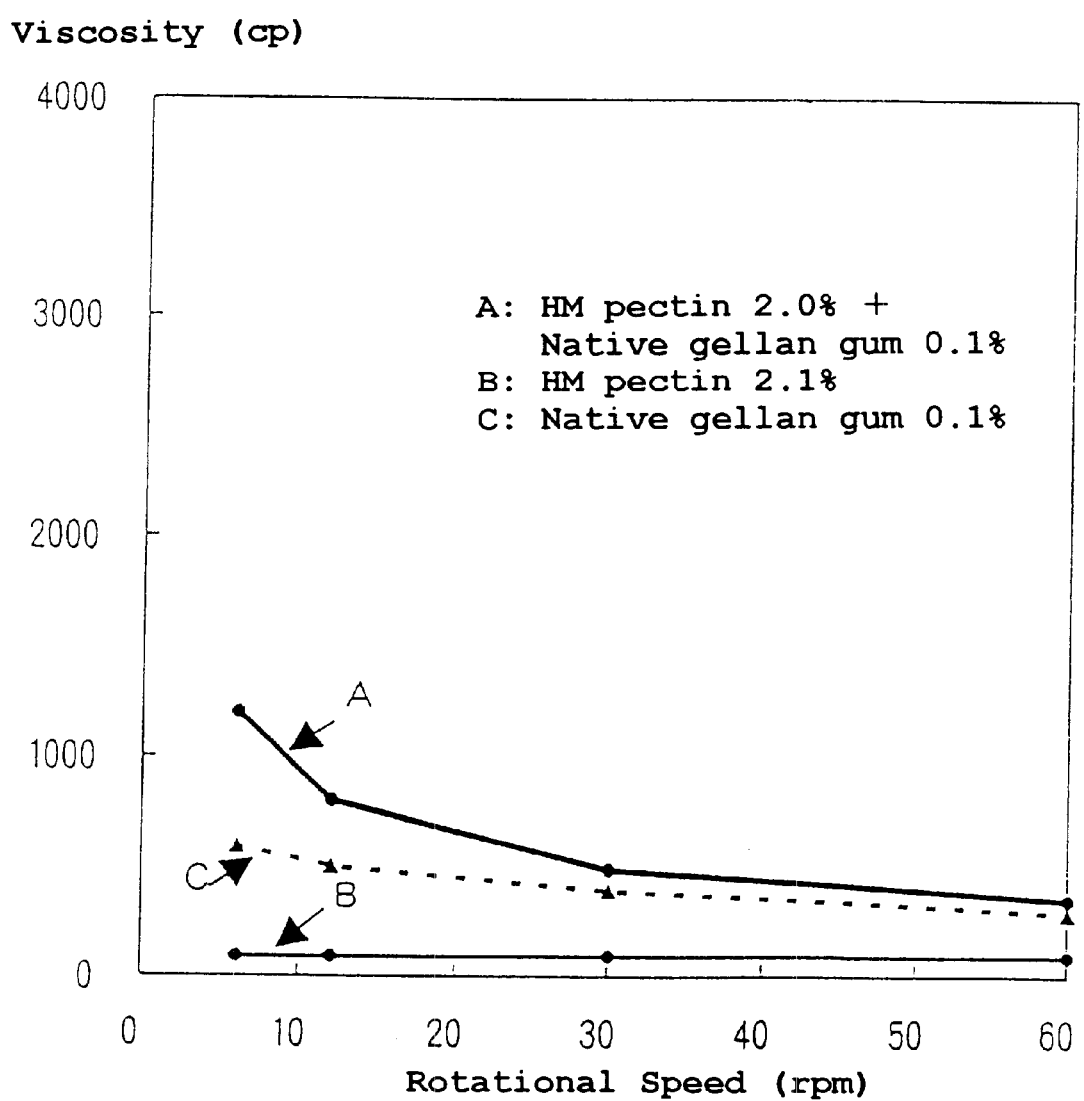
Figure 35:
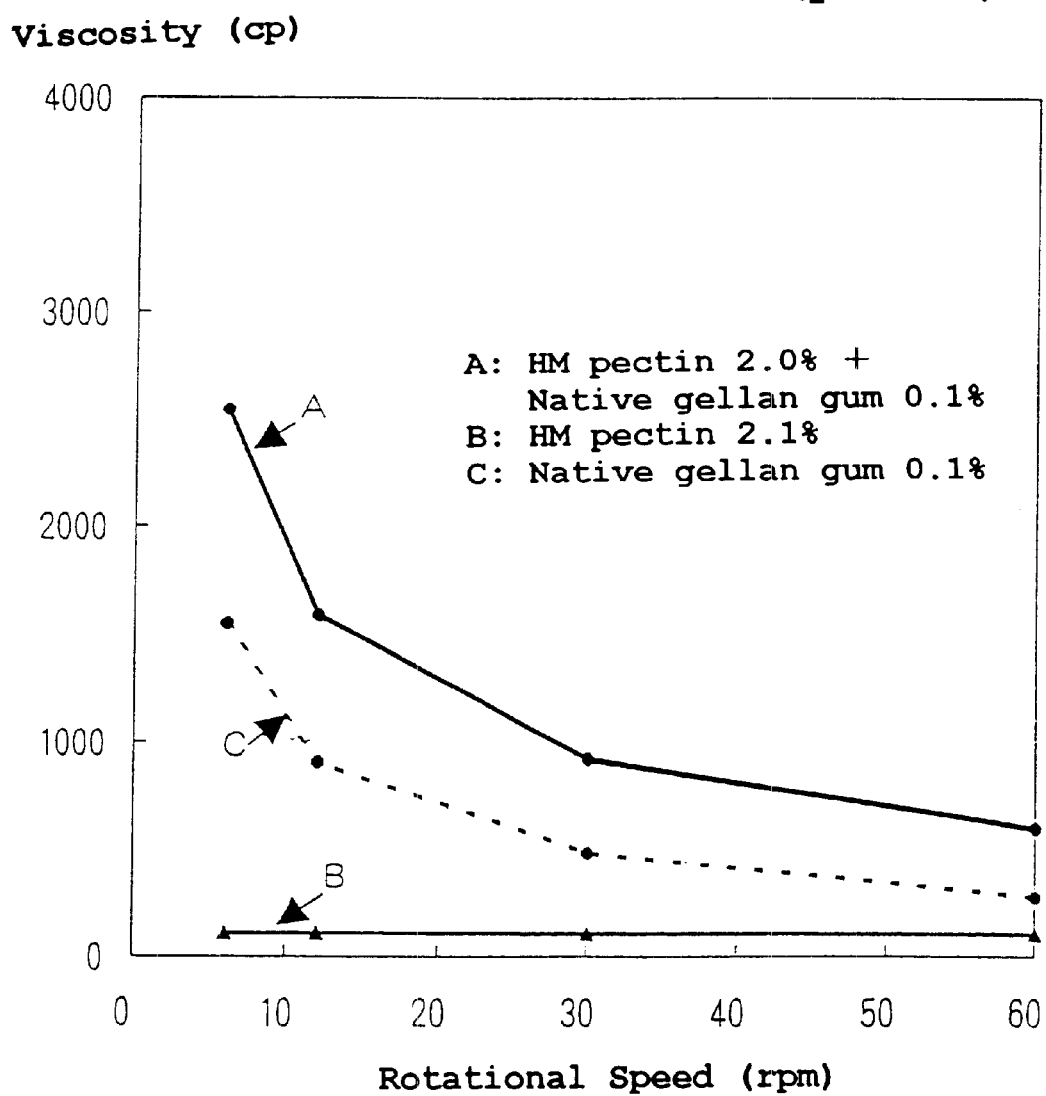

To 50 g of water was added 0.1 g of native gellan gum, and the mixture was heated for dissolving at 80° C. for 10 minutes. Separately, 2 g of HM pectin was placed in 50 g of water and the mixture was heated for dissolving at 80° C. for 10 minutes. The two solutions were admixed and the viscosity of the combined solution was measured (FIG. 34). Similarly, as in Experiment Example (7-2), the solutions adjusted to pH 3.5 were prepared and admixed and the viscosity of the combined solution was measured (FIG. 35).

Experiment Example (7-19)

Figure 36:
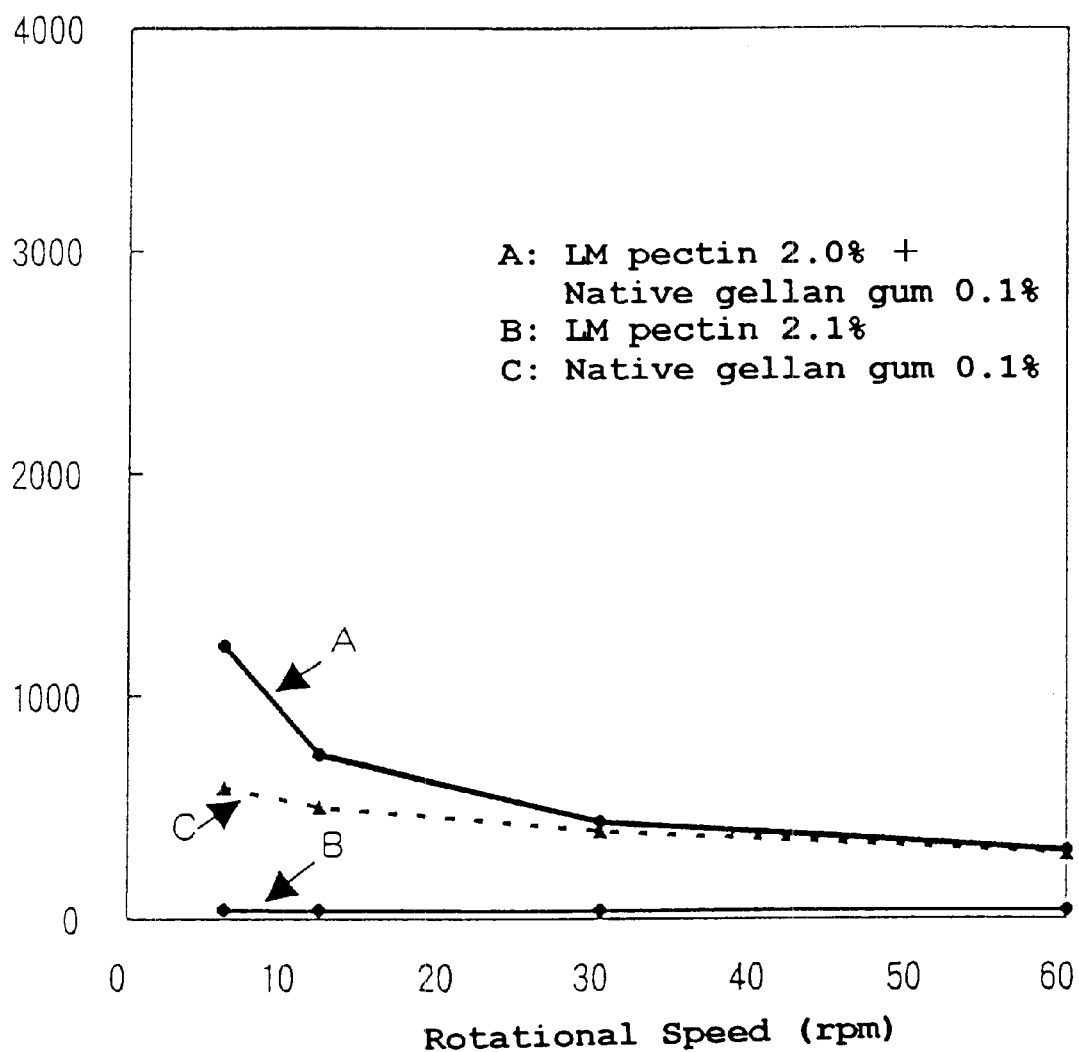
Figure 37:
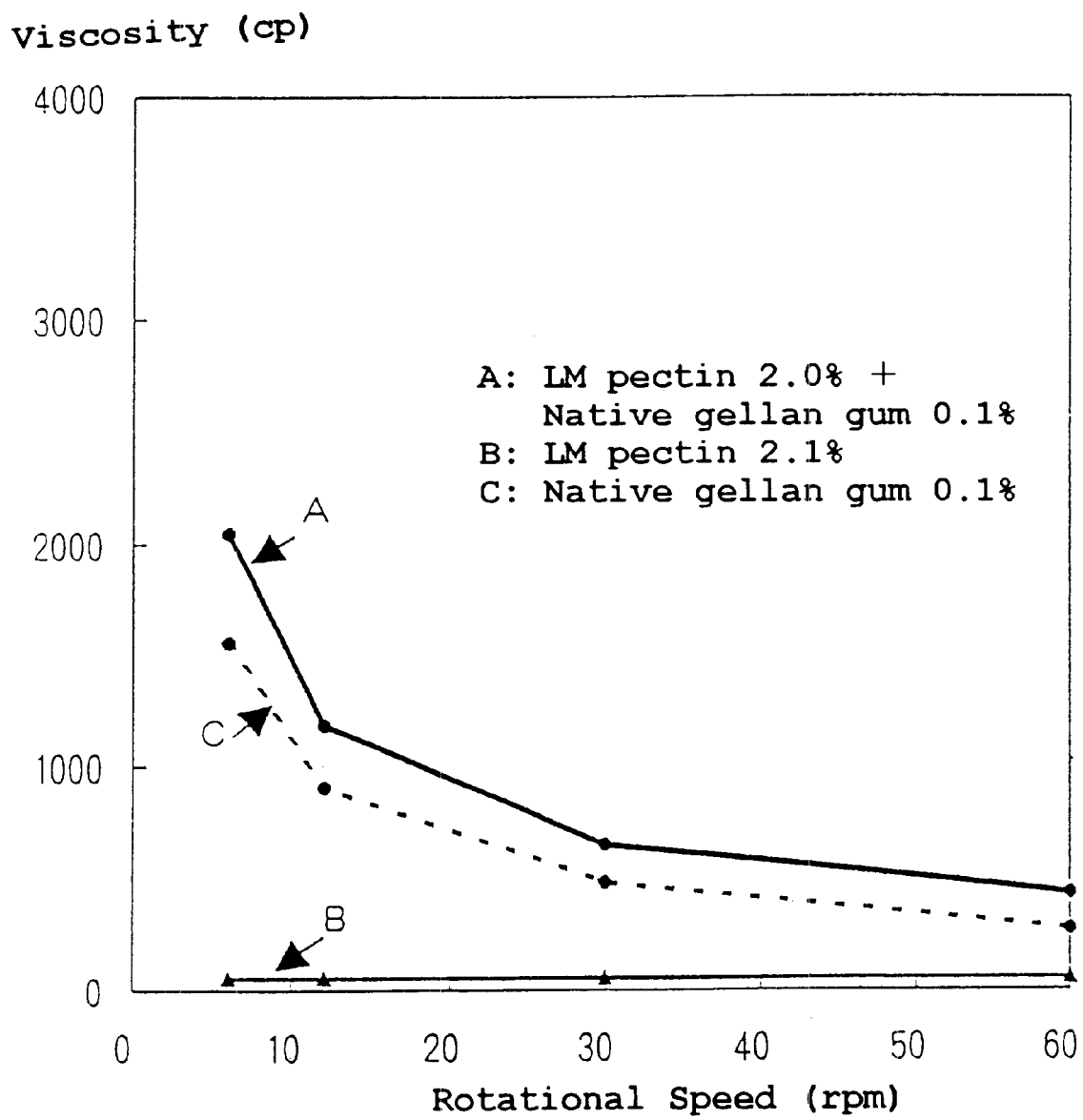

To 50 g of water was added 0.1 g of native gellan gum, and the mixture was heated for dissolving at 80° C. for 10 minutes. Separately, 2 g of LM pectin was placed in 50 g of water and the mixture was heated for dissolving at 80° C. for 10 minutes. The two solutions were admixed and the viscosity of the combined solution was measured (FIG. 36). Similarly, as in Experiment (7-2), the solutions adjusted to pH 3.5 were prepared and admixed and the viscosity of the combined solution was measured (FIG. 37).

As will be apparent from Experiment Examples (7-18) and (7-19), the synergism between native gellan gum and pectin in thickening was not remarkable.

Experiment Example (7-20)

Figure 38:
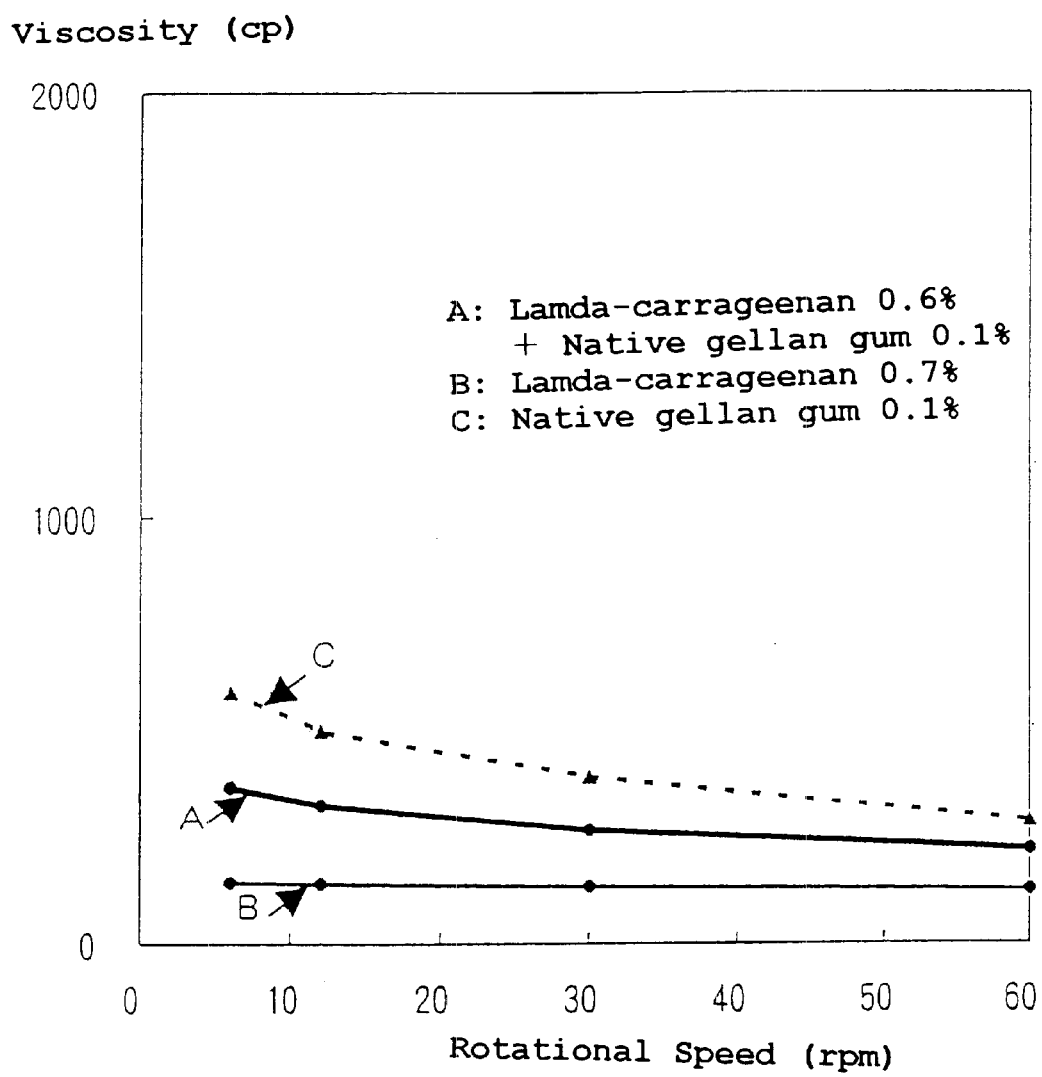
Figure 39:
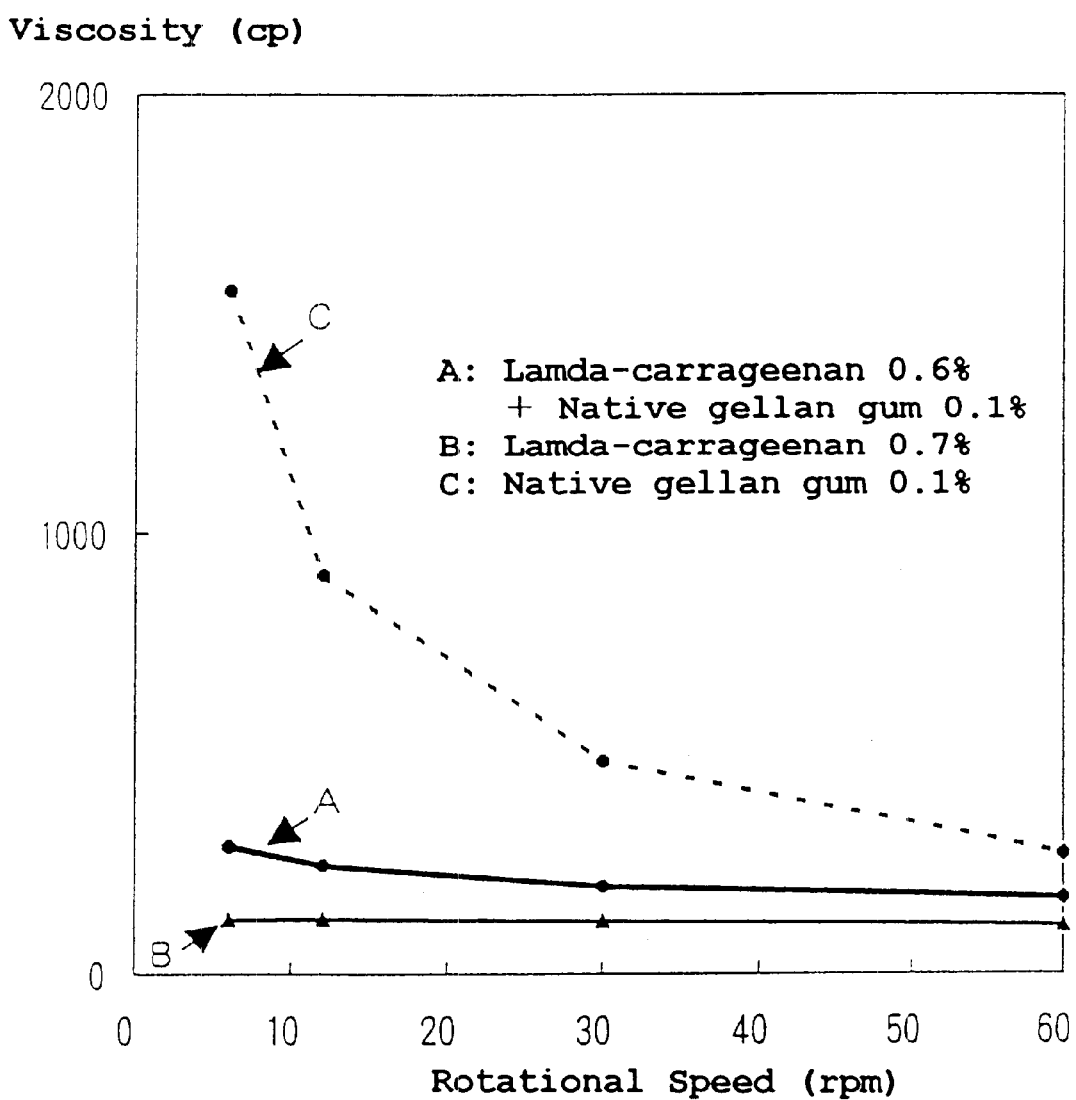

To 50 g of water was added 0.1 g of native gellan gum, and the mixture was heated for dissolving at 80 for 10 minutes. Separately, 0.6 g of lamda-carrageenan was placed in 50 g of water and heated for dissolving at 80° C. for 10 minutes. The two solutions were admixed and the viscosity of the combined solution was measured (FIG. 38). Similarly, as in Experiment Example (7-2), the solutions adjusted to pH 3.5 were prepared and admixed and the viscosity of the combined solution was measured (FIG. 39).

Experiment Example (7-21)

Figure 40:
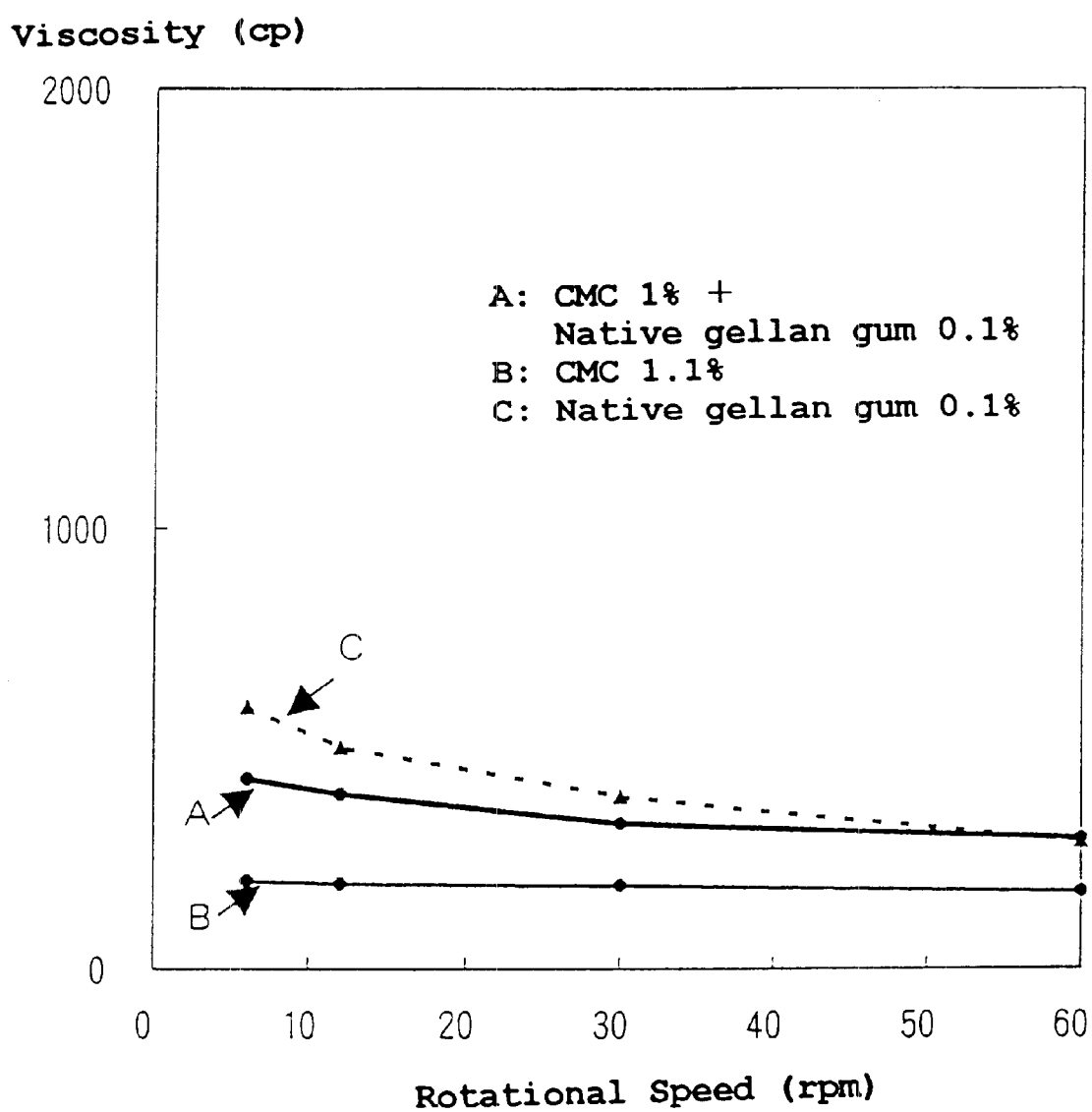
Figure 41:
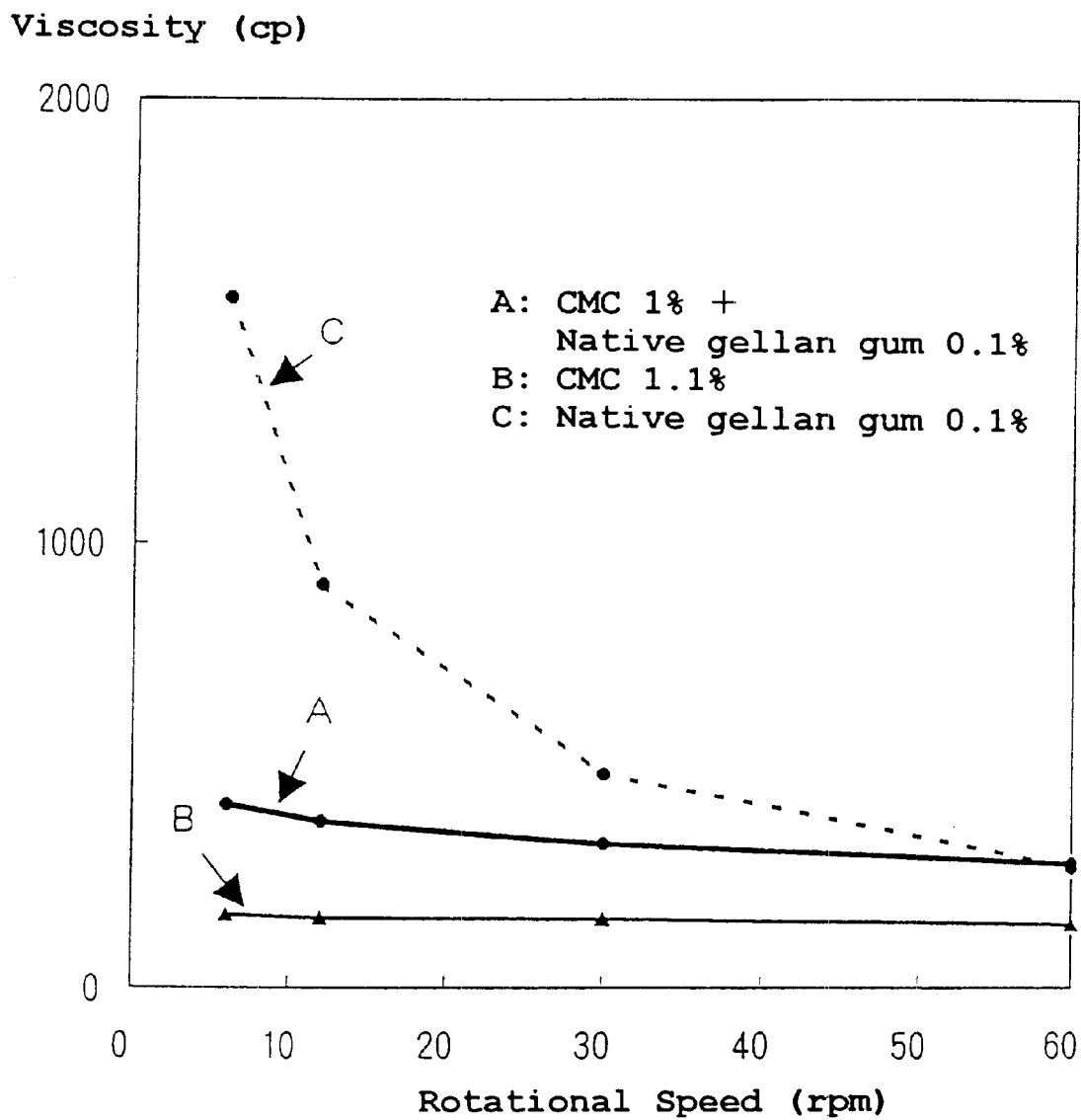

To 50 g of water was added 0.1 g of native gellan gum, and the mixture was heated for dissolving at 80° C. for 10 minutes. Separately, 1 g of CMC (carboxymethylcellulose) was placed in 50 g of water and heated for dissolving at 80° C. for 10 minutes. The two solutions were admixed and the viscosity of the combined solution was measured (FIG. 40). Similarly, as in Experiment Example (7-2), the solutions adjusted to pH 3.5 were prepared and admixed and the viscosity of the combined solution was measured (FIG. 41).

Experiment Example (7-22)

Figure 42:
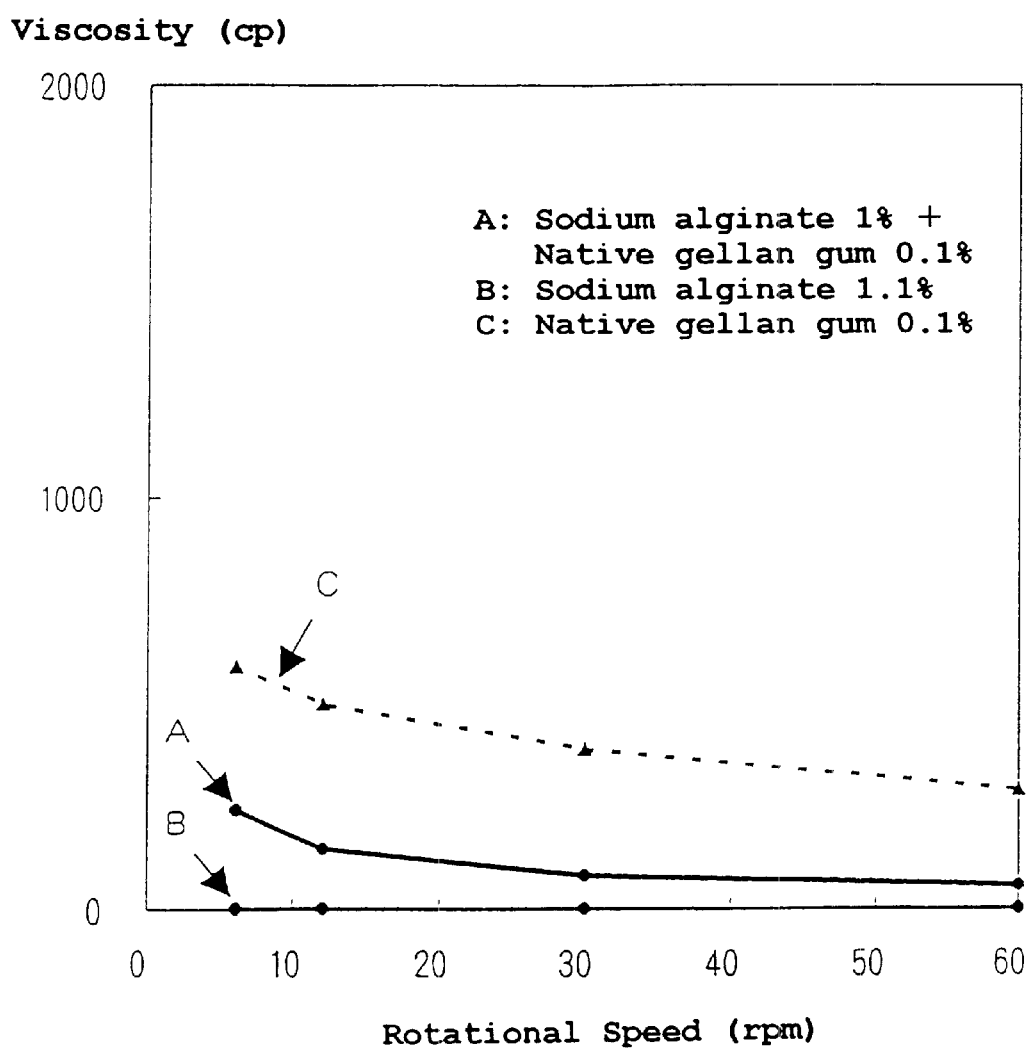
Figure 43:
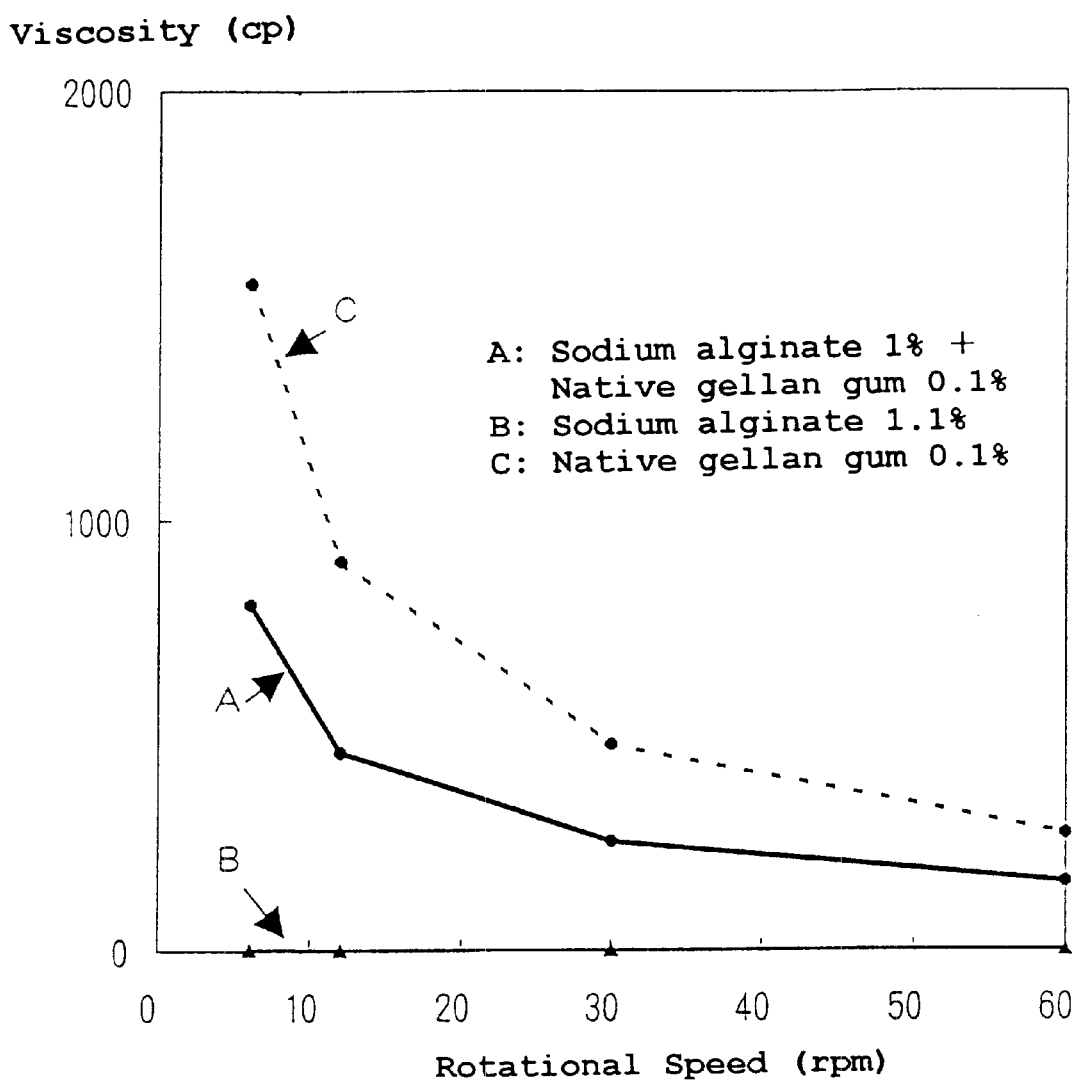

To 50 g of water was added 0.1 g of native gellan gum, and the mixture was heated for dissolving at 80° C. for 10 minutes. Separately, 1 g of sodium alginate was placed in 50 g of water and heated for dissolving at 80 for 10 minutes. The two solutions were admixed and the viscosity of the combined solution was measured (FIG. 42). Similarly, as in Experiment Example (7-2), the solutions adjusted to pH 3.5 were prepared and admixed and the viscosity of the combined solution was measured (FIG. 43).

Experiment Example (7-23)

Figure 44:
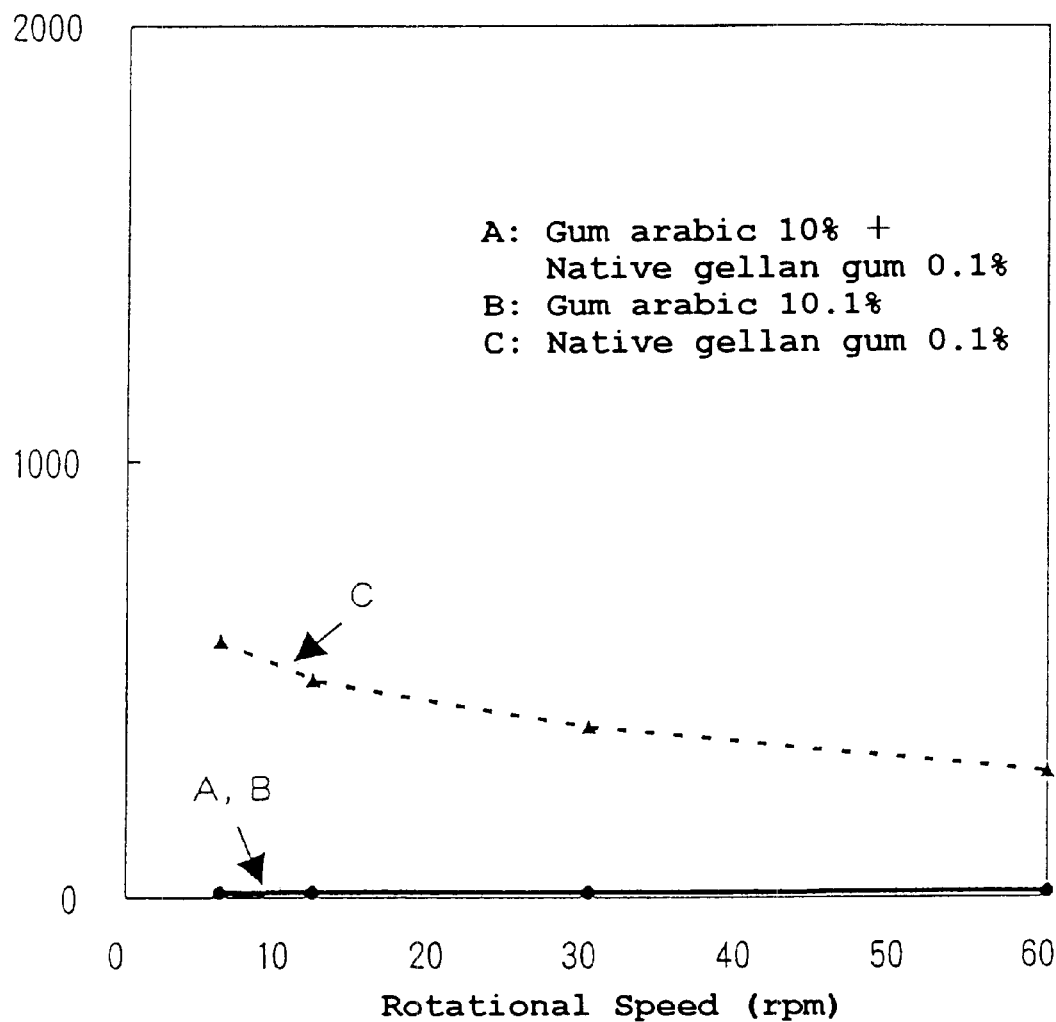
Figure 45:
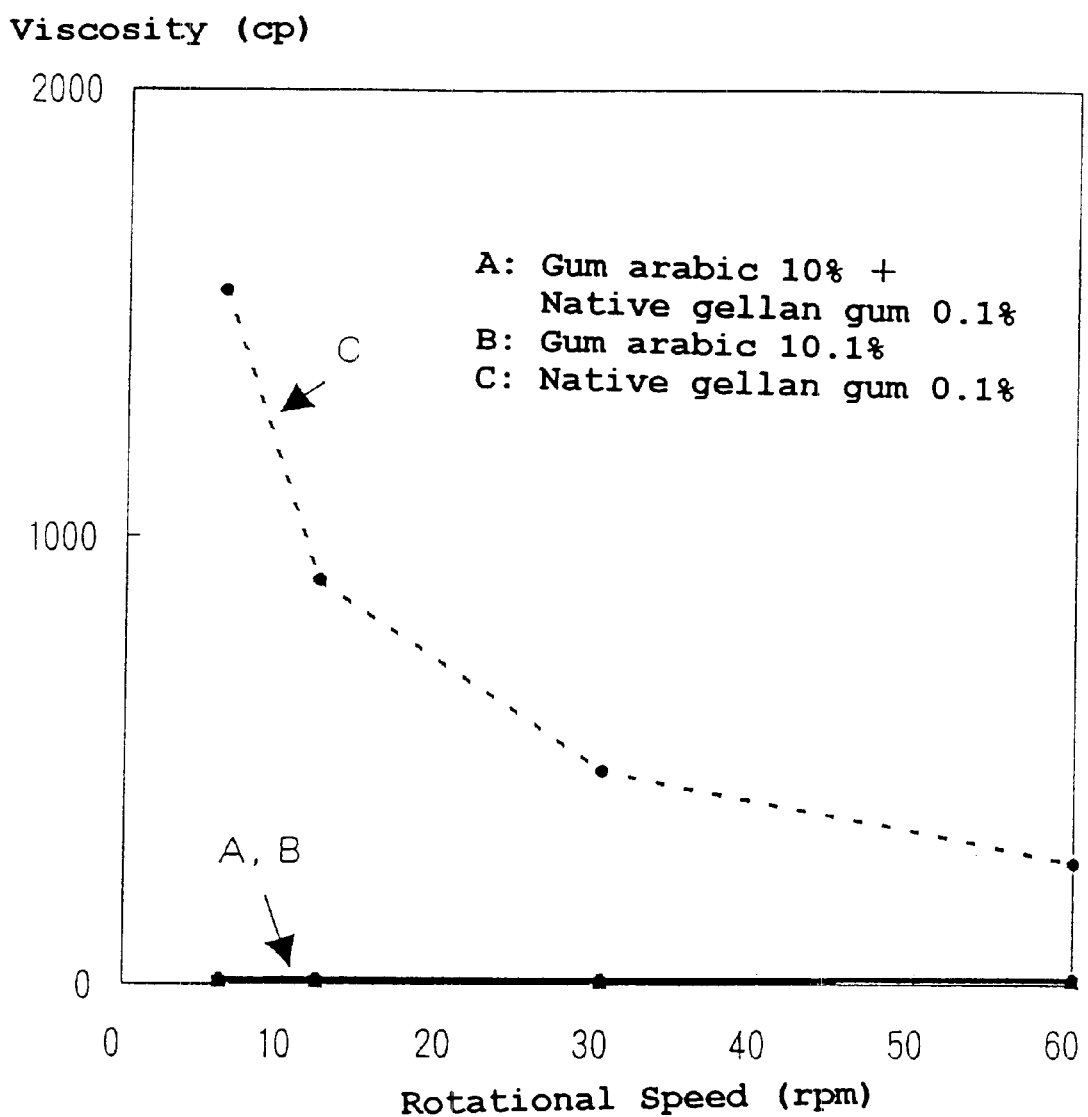

To 50 g of water was added 0.1 g of native gellan gum, and the mixture was heated for dissolving at 80° C. for 10 minutes. Separately, 10 g of gum arabic was placed in 50 g of water and heated for dissolving at 80° C. for 10 minutes. The two solutions were admixed and the viscosity of the combined solution was measured (FIG. 44). Similarly, as in Experiment Example (7-2), the solutions adjusted to pH 3.5 were prepared and admixed and the viscosity of the combined solution was measured (FIG. 45).

It will be apparent from Experiment Examples (7-20)~(7-23) that when native gellan gum is used in combination with lamda-carrageenan, carboxymethylcellulose, sodium alginate or gum arabic, no synergistic improvement in thickening effect was obtained but rather a decrease in viscosity was found.

Experiment Example (7-24)

To 50 g of water was added 0.1 g of gellan gum, and the mixture was heated for dissolving at 80° C. for 10 minutes. Separately, 0.5 g of tamarind seed gum was placed in 50 g of water and heated for dissolving at 80° C. for 10 minutes. The two solutions were admixed and the viscosity of the combined solution was measured. However, this solution underwent gelation so that no measured value could be obtained. Therefore, the concentration of gellan gum was increased gradually from a low level and the time course of viscosity gain from a solution state (little viscosity) to the onset of gelation was monitored.

Figure 46:
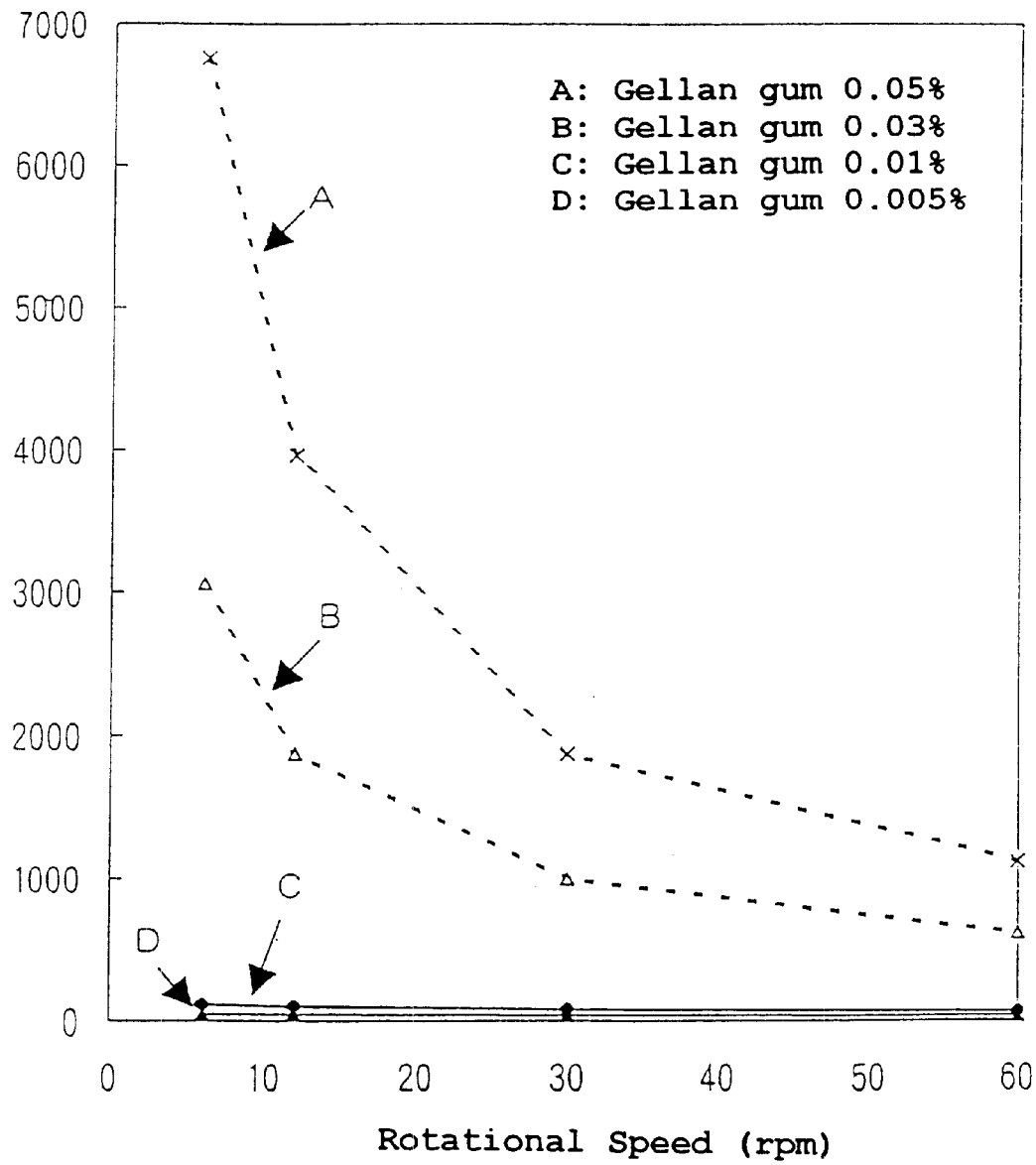

The results are shown in FIG. 46. Thus, whereas no viscosity was found up to 0.01% of gellan gum, the solution suddenly formed a gel as its concentration was increased to 0.03%, indicating a very narrow range of thickening effect.

Example 8

Heat Resistance-imparting Effect

Examples (8-1)~(8-3), Comparative Examples (8-1)~(8-5)

Bean curds (tofu) were prepared according to the recipes shown in Tables 4 and 5 (each value represents weight %)

and the condition of each bean cured was examined before and after retort treatment.

The protocol for the production of tofu was as follows.

To soya milk was added native gellan gum or, as control, gellan gum with stirring and the mixture was stirred for dissolving at 85° C. for 10 minutes. The temperature was then allowed to fall to 60% and the coagulant magnesium chloride was added, followed by stirring, filling in a vessel and quenching to 5° C.

The bean curds prepared as above were examined before and after retort treatment. The results are shown in Tables 4 and 5.

TABLE 4

|  | Comparative Example (8-1) | Example (8-1) | Example (8-2) | Example (8-3) |
|---|---|---|---|---|
| Native gellan gum | 0 | 0.02 | 0.05 | 0.1 |
| Gellan gum | 0 | 0 | 0 | 0 |
| Soya milk | 99.9 | 99.88 | 99.85 | 99.8 |
| Magnesium chloride | 0.1 | 0.1 | 0.1 | 0.1 |
| Before retort treatment | Regardless of addition or non-addition of native gellan gum, all tofu samples were smooth and well palatable. | | | |
| After retort treatment | Marked syneresis occurred and the tofu texture was disrupted to give a dry mouth-feel. No market value at all. | Compared with the non-addition sample, syneresis was remarkably inhibited and although the tofu texture was slightly roughened, the mouth-feel was still satisfactory. | | Substantially no syneresis was found. No case hardening or roughing occurred, and the texture was as delicate and smooth as the regular coarse-textured tofu. |

TABLE 5

|  | Comparative Example (8-2) | Comparative Example (8-3) | Comparative Example (8-4) | Comparative Example (8-5) |
|---|---|---|---|---|
| Native gellan gum | 0 | 0 | 0 | 0 |
| Gellan gum | 0.01 | 0.02 | 0.05 | 0.1 |
| Soya milk | 99.9 | 99.8 | 99.85 | 99.8 |
| Magnesium chloride | 0.1 | 0.1 | 0.1 | 0.1 |
| Before retort treatment | When the addition level of gellan gum was 0.02 or less, substantially no difference was found from non-addition samples. However, when it exceeded 0.02, remarkable water separation occurred with the progress of time, giving a hard and dry mouth-feel. | | | |
| After retort treatment | At any level of addition, the "roughening" of tofu texture due to retort treatment was not ameliorated. All samples gave dry mouth-feels and were different from the regular tofu in appearance and palatability. Particularly at 0.05 and higher levels, the samples tended to disintegrate and were far removed from the concept of tofu. | | | |

The retort treatment was carried out using the retort sterilizer RCS-40 RTG, manufactured by Nippan Seisakusho, at 121° C. for 20 minutes.

As shown in Tables 4 and 5, the bean curds according to the examples were invariably very palatable, being not different in texture from the regular bean curd, both before and after retort treatment. In contrast, the bean curds not containing native gellan gum were not tofu-like, with their curd structures having been disrupted by retort treatment. When gellan gum was added in lieu of native gellan gum, rather more considerable syneresis took place and the product had a hard and coarse mouth-feel, due to the failure to prevent degeneration of its texture by retort treatment.

Example 9

Syneresis Inhibitor

Examples (9-1) ~(9-4), Comparative Examples (9-1) ~(9-7)

Gels 1 containing kappa-carrageenan as a gelling agent [Example (9-1), Comparative Example (9-1), and Comparative Example (9-2)], gels 2 containing agar as a gelling agent [Example (9-2), Comparative Example (9-3), and Comparative Example (9-4)], gels 3 containing potato starch as a gelling agent [Example (9-3), Comparative Example (9-5), and Comparative Example (9-6)], and gels 4 containing gellan gum as a gelling agent [Example (9-4), Comparative Example (9-7)] were respectively prepared.

To be specific, gels 1 were prepared by dissolving 0.8% (weight %, the same applies hereinafter) of kappa-carrageenan and various syneresis inhibitors added at the levels (wt. %, the same applies hereinafter) indicated in Table 6 in water at 85° C. with constant stirring, adding 0.1% of potassium chloride, adjusting the mixture to pH 3.5, and cooling it to 5° C. Incidentally, kappa-carrageenan is the gelling agent most universally incorporated in jelly foods such as fruit jellies and the adjustment to pH 3.5 was made for alignment with its pH of 3.5.

Gels 2 were also prepared by dissolving 0.8% of agar (Ina Food) and the various syneresis inhibitors indicated in Table 7, in water at 85° C. with constant stirring and cooling the solution to 5° C.

Gels 3 were prepared by dissolving potato starch (Hokuren Sha) and the various syneresis inhibitors indicated in Table 8, in water at 85° C. with constant stirring and cooling the solution to 5%.

Gels 4 were prepared by dissolving 0.2% of gellan gum (San-eigen F. F. I.) and the various syneresis inhibitors indicated in Table 9, in water at 85° C. with constant stirring, then adding 0.1% of calcium lactate, and cooling the mixture to 5° C.

The gels 1 through 4 were compared for the rate of syneresis and gel characteristics.

The iota-carrageenan (San-eigen F. F. I.) used in the comparative examples is a substance known to be the most potent inhibitor of syneresis for use in gel compositions.

The results are shown in Tables 6 through 9.

TABLE 6

Gels 1

| syneresis inhibitor | Non-addition control | Example (9-1) Native gellan gum | | | Comparative Example (9-1) Iota-carrageenan | | | Comparative Example (9-2) Gellan gum | | |
|---|---|---|---|---|---|---|---|---|---|---|
| | | 0.05% | 0.10% | 0.15% | 0.05% | 0.10% | 0.15% | 0.05% | 0.10% | 0.15% |
| Rate of syneresis (%) | 6.6 | 4.0 | 2.4 | 1.1 | 5.2 | 4.0 | 4.1 | 7.8 | 4.9 | 2.2 |
| Gel condition | Considerable syneresis occurred and the gel became hard and fragile, losing the fresh eating quality. | At the 0.15% level, the rate of syneresis showed an extremely low value of 1.1%. Regardless of the level of addition, no change was found in gel characteristics such as elasticity and firmness or in palatability. | | | Compared with non-addition control, the rate of syneresis declined but the effect was insufficient. At 0.10% and higher levels, definite viscoelasticity developed in gels with consequent alteration of gel characteristics and palatability. | | | At the 0.15% level, the gum inhibited syneresis more effectively than iota-carrageenan. However, at 0.10% and higher levels, the gel became remarkably hard with consequent deterioration of gel characteristics. | | |

TABLE 7

Gels 2

| syneresis inhibitor | Non-addition control | Example (9-2) Native gellan gum | | | Comparative Example (9-3) Iota-carrageenan | | | Comparative Example (9-4) Gellan gum | | |
|---|---|---|---|---|---|---|---|---|---|---|
| | | 0.05% | 0.10% | 0.15% | 0.05% | 0.10% | 0.15% | 0.05% | 0.10% | 0.15% |
| Rate of syneresis (%) | 4.2 | 4.0 | 2.4 | 1.2 | 4.0 | 3.8 | 2.1 | 4.2 | 4.0 | 3.8 |
| Gel condition | Considerable syneresis was noted. | At the 0.15% level, the rate of syneresis was as low as 1.2%. Regardless of the level of addition, no change was found in gel characteristics such as elasticity and firmness or in palatability. | | | Compared with non-addition control, the rate of syneresis declined but the effect was insufficient. At 0.10% and higher levels, definite viscoelasticity developed in gels, resulting in alteration of gel characteristics and palatability. | | | There was no syneresis-inhibiting effect at all. Rather, at 0.10% and higher levels, the gels became considerably hard with complete loss of gel characteristics. | | |

TABLE 8

Gels 3

| syneresis inhibitor | Non-addition control | Example (9-3) Native gellan gum | | | Comparative Example (9-5) Iota-carrageenan | | | Comparative Example (9-6) Gellan gum | | |
|---|---|---|---|---|---|---|---|---|---|---|
| | | 0.05% | 0.10% | 0.15% | 0.05% | 0.10% | 0.15% | 0.05% | 0.10% | 0.15% |
| Rate of syneresis (%) | 3.1 | 1.3 | 0.5 | 0 | 1.8 | 1.3 | 1.1 | 1.4 | 0.8 | 0.4 |
| Gel condition | Considerable syneresis was noted. | At the 0.10% level, the rate of syneresis was as low as 0.5%. At the 0.15% level, the rate of syneresis declined | | | Compared with non-addition control, the rate of syneresis declined but the effect was still insufficient. At 0.10% and higher | | | Compared with non-addition control, the rate of syneresis declined but the effect was still insufficient. At 0.10% and higher | | |

TABLE 8-continued

Gels 3

| syneresis inhibitor | Non-addition control | Example (9-3) Native gellan gum | | | Comparative Example (9-5) Iota-carrageenan | | | Comparative Example (9-6) Gellan gum | | |
|---|---|---|---|---|---|---|---|---|---|---|
| | | 0.05% | 0.10% | 0.15% | 0.05% | 0.10% | 0.15% | 0.05% | 0.10% | 0.15% |
| | | to 0%, indicating an unprecedentedly remarkable inhibitory effect. Regardless of the level of addition, no change was found in gel characteristics such as elasticity and firmness or in palatability. | | | levels, definite viscoelasticity developed in gels, resulting in alteration of gel characteristics and palatability. | | | levels, gels were considerably hard with complete loss of gel characteristics. | | |

TABLE 9

Gels 4

| syneresis inhibitor | Non-addition control | Example (9-3) Native gellan gum | | | Comparative Example (9-5) Iota-carrageenan | | |
|---|---|---|---|---|---|---|---|
| | | 0.05% | 0.10% | 0.15% | 0.05% | 0.10% | 0.15% |
| Rate of syneresis (%) | 7.2 | 2.8 | 1.4 | 0.3 | 5.6 | 3.9 | 3.1 |
| Gel condition | Considerable syneresis occurred and the gel became hard and fragile, losing the fresh eating quality. | At the 0.10% level, the rate of syneresis was depressed to as low as 1.4%. At 0.15%, the rate of syneresis was as low as 0.3%. In each case, no change was noted in gel characteristics such as elasticity and firmness or in palatability. | | | Compared with non-addition control, the rate of syneresis was suppressed but the effect was insufficient. At 0.10% and higher levels, definite viscoelasticity developed in gels, with consequent alteration of gel characteristics and palatability. | | |

Example (9-5)

According to the following recipe, native gellan gum, pectin and trisodium citrate were added to water and heated for dissolving at 85° C. with stirring for 10 minutes. Then, frozen strawberries, crushed in advance, and citric acid (crystals) were added. The mixture was stirred for 1 minute and sugar was added. The whole mixture was stirred for another 5 minutes and then cooled to 5° C. to provide a strawberry jam.

Even when stored in the refrigerator for one month, this jam showed no separation of water.

<Recipe for strawberry jam>

| | |
|---|---|
| Native gellan gum | 0.15 wt. % |
| LM pectin | 1.2 |
| Trisodium citrate | 0.4 |
| Frozen strawberries | 40 |
| Citric acid (crystals) | 0.1 |
| Sugar | 35 |
| Water | Balance |
| Total | 100 wt. % |

Example (9-6)

According to the following recipe, native gellan gum, kappa-carrageenan, agar, fruit juice and sugar were added to water and the mixture was stirred for dissolving at 85° C. with stirring for 10 minutes. Then, citric acid (crystals) and flavor were added and after 1 minute's stirring, the mixture was held in a cooling water bath at 5° C. for 2 hours to provide a fruit jelly at pH 3.6.

Even when stored in the refrigerator, this fruit jelly showed substantially no syneresis.

<Recipe for fruit jelly>

| | |
|---|---|
| Native gellan gum | 0.15 wt. % |
| Kappa-carrageenan | 0.4 |
| Agar | 0.4 |
| Concentrated (1/5) orange juice | 4 |
| Sugar | 15 |
| Citric acid (crystals) | 0.2 |
| Flavor | 0.1 |
| Water | Balance |
| Total | 100 wt. % |

Example (9-7)

According to the following recipe, native gellan gum, gelatin and sugar were added to water and the mixture was stirred for dissolving at 85° C. for 10 minutes. Then, soy and salt were added and stirred for 5 minutes to provide a nikogori jelly (a frozen gelatinous food). This nikogori jelly was packed into a can filled with crab flesh (q.s.) and, after clinching, was allowed to stand at 5° C. overnight to provide a canned nikogori crab.

Whereas a control canned food not containing native gellan gum showed about 10% syneresis after one day at room temperature, the above canned nikogori crab food showed substantially no separation of water and remained quite savory without alteration of palatability.

| <Recipe for nikogori jelly> | |
|---|---|
| Native gellan gum | 0.1 wt. % |
| Gelatin | 1.5 |
| Sugar | 3 |
| Soy | 2 |
| Salt | 2 |
| Seasoning | 0.5 |
| Water | Balance |
| Total | 100 wt. % |

Example (9-8)

Using the following recipe, a hamburg steak was prepared in accordance with the usual culinary procedure.

This hamburg steak was frozen once and thawed in an electronic or microwave range. Whereas the control hamburg steak not containing native gellan gum released a large amount of water with the consequent roughening of the texture, the above product showed substantially no syneresis and was a juicy hamburg steak.

| <Recipe for hamburg steak> | |
|---|---|
| Native gellan gum | 1 Wt. % |
| Kappa-carrageenan | 0.1 |
| Minced pork | 45 |
| Lard | 10 |
| Powdery soya protein | 2 |
| Onion saute | 12 |
| Bread crumbs (home-made grade) | 7 |
| Whole egg | 5 |
| Salt | 0.5 |
| Sugar | 0.5 |
| Seasoning | 1 |
| Water | Balance |
| Total | 100 wt. % |

Example (9-9)

Using the following recipe, a toothpaste was prepared in accordance with the conventional protocol.

Whereas the control toothpaste not containing native gellan gum showed syneresis on 1-month-long use at room temperature, the above toothpaste showed no syneresis at all.

| <Recipe for toothpaste> | |
|---|---|
| Native gellan gum | 0.15 wt. % |
| Silicon dioxide | 17.6 |
| Aluminum hydroxide | 5 |
| Kappa-carrageenan | 0.4 |
| Trisodium phosphate | 1.3 |
| Sodium lauryl sulfate | 1 |
| Sodium fluoride | 0.2 |
| Titanium dioxide | 0.3 |
| Saccharin sodium | 0.2 |
| Flavor | 0.06 |
| Color | 0.15 |
| Water | Balance |
| Total | 100 wt. % |

Example (9-10)

According to the following recipe, native gellan gum, kappa-carrageenan, glycerin and preservative were added to water and the mixture was stirred at 85° C. for 10 minutes. Then, ethanol and flavor were added and the mixture was cast in a mould and cooled to 10° C., whereby a solid aromatic article was provided.

This aromatic article showed no syneresis even when left standing in an interior environment for 1 month. Thus, this article was free from the problem that separating water covers up the surface to interfere with emanation of the scent.

| <Recipe for a solid aromatic article> | |
|---|---|
| Native gellan gum | 0.5 wt. % |
| Kappa-carrageenan | 1 |
| Glycerin | 5 |
| Preservative | 0.5 |
| 75% Ethanol | 5 |
| Jasmine oil | 10 |
| Water | Balance |
| Total | 100 wt. % |

Example (9-11)

According to the following recipe, porous polymethacrylate beads (particle diameter range 0.1~100 $\mu$m, mean particle diameter 1~50 $\mu$m) and activator were added to lemon oil and the mixture was stirred to provide an aromatic powder. Separately, native gellan gum, kappa-carrageenan, glycerin and preservative were added to water and heated at 85° C. with stirring for 10 minutes, followed by cooling to about 60° C. to provide an aromatic body or matrix solution. The above aromatic powder was placed in said matrix solution and the mixture was uniformly dispersed by stirring and poured into a mold, followed by cooling to 10° C. to provide a solid aromatic product.

This aromatic article showed no syneresis even on 1-month-long standing in an interior environment. Therefore, the article was free from the trouble that separating water covers up the surface to interfere with emanation of the scent.

| <Recipe for a solid aromatic article> | |
| --- | --- |
| Lemon oil | 10 wt. % |
| Porous polymethacrylate beads | 0.5 |
| Activator | 0.2 |
| Native gellan gum | 0.5 |
| Kappa-carrageenan | 1 |
| Glycerin | 5 |
| Preservative | 0.5 |
| 75% Ethanol | 5 |
| Water | Balance |
| Total | 100 wt. % |

Example (9-12)

According to the following recipe, a canned raw-type pet food was prepared in the routine manner.

Even when stored for 1 month, this canned pet food showed substantially no syneresis, retaining the juicy palatability available immediately after preparation.

| <Recipe for pet food> | |
| --- | --- |
| Native gellan gum | 0.1 wt. % |
| Minced beef | 20 |
| Beef (lean) | 50 |
| Kappa-carrageenan | 0.2 |
| Seasoning | 1 |
| Salt | 1 |
| Casein sodium | 2 |
| Starch | 2 |
| Water | Balance |
| Total | 100 wt. % |

Example (9-13)

Mean Bun

Using the following recipe, the stuffing and skin of a meat bun were respectively prepared and a meat bun was then produced.

In preparing the meat bun stuffing, native gellan gum was used in the form of a 1% aqueous solution and the ingredients were roasted in a frypan and adjusted to a suitable water content.

| <Recipe for meat bun stuffing> | |
| --- | --- |
| Native gellan gum, 1% aq. sol. | 30 wt. % |
| Kudzu-ko (arrowroot flour) | 4 |
| Minced pork | 100 |
| Onion | 40 |
| Grated ginger | 1 |
| Bamboo shoot (strips) | 35 |
| Salt | 0.5 |
| Seasoning | 1 |
| | 211.5 wt. % |
| Water | q.s. |

| <Recipe for meat bun skin> | |
| --- | --- |
| Soft flour | 100 wt. % |
| Salt | 1 |
| Baking powder | 0.4 |
| Sugar | 12 |
| Dry yeast | 1 |
| Water | 40 |
| Lard | 3 |
| | 157.4 wt. % |

Example (9-14)

Meat Bun

Using the following recipe, the stuffing and skin for a meat bun were respectively prepared and a meat bun was produced in accordance with the conventional protocol.

In preparing the stuffing, native gellan gum was used in the form of a 1% aqueous solution and either xanthan gum or guar gum was additionally used in the form of a 1% aqueous solution. The ingredients for the stuffing were roasted in a frypan and adjusted to a suitable overall water content.

| <Recipe for meat bun stuffing> | |
| --- | --- |
| Native gellan gum, 1% aq. sol. | 30 wt. % |
| Xanthan gum, 1% (guar gum 1% aq. sol.) | 10 |
| Kudzu-ko (arrowroot flour) | 4 |
| Minced pork | 100 |
| Onion | 40 |
| Grated ginger | 1 |
| Bamboo shoot (strips) | 35 |
| Salt | 0.5 |
| Seasoning | 1 |
| | 221.5 wt. % |
| Water | q.s. |

| <Recipe for meat bun skin> | |
| --- | --- |
| Soft flour | 100 wt. % |
| Salt | 1 |
| Baking powder | 0.4 |
| Sugar | 12 |
| Dry yeast | 1 |
| Water | 40 |
| Lard | 3 |
| | 157.4 wt. % |

| Example of Recipe-1 (glazing agent) | |
| --- | --- |
| Native gellan gum | 0.03 wt. % |
| Tamarind seed gum | 0.15 |
| Guar gum | 0.25 |
| Sugar | 14 |
| Water | Balance |
| Total | 100 wt. % |

This glazing agent is used for the purpose of covering the surface of a frozen food with a thin coat of ice, and an ice candy can be produced by dipping a plain ice candy in the grazing agent and freezing it.

Example of Recipe-2

Glazing Agent

| Native gellan gum | 0.03 wt. % |
|---|---|
| Agar | 0.5 |
| Sugar | 18 |
| Water | Balance |
| Total | 100 wt. % |

This glazing agent is used for the purpose of covering the surface of a food, such as a fruit, to preserve its qualities inclusive of appearance (gloss, brightness) and quality (freshness, plumpness), and glazed strawberries can be provided by dipping cake-making strawberries in a bath of said glazing agent and cooling them.

Example 10

Foam Stabilizer

Example (10-1)

First, 150 kg of raw egg white was weighed into the bowl of a stirring mixer and, using a whipper, beated at 107 rpm for 30 seconds until a homogeneous foam had been obtained. Then, while the beating was continued at 216 rpm, the whole amount of a syrup prepared by stirring a mixture of 124.5 kg of sucrose and 0.15 kg of native gellan gum in 150 kg of water for dissolving at 80° C. for 10 minutes was added in small portions over 3 minutes at a temperature not below 75° C. After completion of addition, the mixture was beated at 216 rpm for a further 4 minutes to provide a meringue. This meringue had a lustrous and fine cellular structure and had been beaten so stiff that it did not drop even when the bowl was inverted.

The meringue thus prepared was placed in a bowl and left standing at room temperature and the time course of syneresis and foam stability was monitored. As a result, neither separation of water nor a change in fineness of the foam was observed even after an elapse of 48 hours.

The above meringue, 50 g, was placed on top of a lemon pie 20 cm in diameter and baked in an oven at 180° C. for 10 minutes. It was found that the topped cake could be baked with the meringue retaining the initial form without deforming.

A similar result was obtained when the white of raw eggs beaten without sugar was supplemented with an aqueous solution of native gellan gum in the same proportion as above to prepare a meringue.

Comparative Example (10-1)

Except that native gellan gum was omitted, a meringue was prepared according to otherwise the same recipe as used in Example (10-1).

When a lemon pie was toped with this meringue immediately after beating and baked, the meringue shrunk to about 50% of the initial height of the topping. Moreover, when the meringue just prepared was placed in a bowl and left standing at room temperature, the separation of water began after a lapse of 10 minutes and the foam disappeared mostly after 1 hour.

Comparative Example (10-2)

Except that 0.74 kg of potassium hydrogen L-tartrate and 0.37 kg of salt were used in lieu of native gellan gum, a meringue was prepared according to otherwise the same recipe and procedure as used in Example (10-1).

When this meringue was used to top a lemon pie and baked, the meringue shrunk to about 60% of its initial height. Moreover, when the meringue just prepared was placed in a bowl and left standing at room temperature, it began to release water at 60 minutes after-preparation and most of the cellular structure of the meringue had disappeared by 2 hours.

Comparative Example (10-3)

Except that 0.15 kg of gellan gum was used in lieu of native gellan gum, a meringue was prepared according to otherwise the same recipe and procedure as used in Example (10-1).

When this meringue was used to top a lemon pie immediately after beating and baked, the topping decreased to about 50% of its initial height. Moreover, when the meringue just prepared was placed in a bowl and left standing at room temperature, it began to release water at 10 minutes and most of the foam had disappeared by 1 hour after preparation.

Example (10-2)

The frozen white of eggs was thawed at room temperature and 20 kg of the thawed egg white was weighed into the bowl of a stirring mixer. Using the whipper, the egg white was beaten to homogeneity at 107 rpm for 30 seconds. Under further beating at 216 rpm, 0.1 kg of wheat flour protein hydrolysate was adcied and the mixture was further beaten for 4 minutes. Separately, a mixture of 27 kg of granulated sugar and 0.1 kg of native gellan gum was added to 20 kg of water and heated to 100° C. to prepare a syrup. This syrup was allowed to cool for 3 minutes and added to the above egg white preparation and the mixture was further beaten for 1 minute to provide a meringue. This meringue was placed in a bowl and kept standing at room temperature for 48 hours. As a result, the meringue was found to remain in the condition immediately after preparation without undergoing syneresis.

One-third of this meringue (33.6 kg) was uniformly added to a mixture of 4.3 kg of egg yolk and 3.5 kg of liquid oil. Then, a mixture of 8.2 kg of wheat flour and 0.1 kg of a baking powder was added, followed by thorough mixing. Thereafter, the remainder of the meringue was added and the mixture was gently stirred for use as a chiffon cake batter. This batter, 140 g, was filled into a chiffon cake No. 14 mould and baked at 180° C. for 30 minutes, whereby a chiffon cake having a delicate texture without evidence of oven shrinkage was obtained.

The conventional chiffon cake has a lower solid content than the regular sponge cake but in order to avoid oven shrinkage, wheat flour must be formulated in a proportion of at least 19% (in the recipe). However, the chiffon cake of this invention could be decreased in wheat flour content down to 14% and, yet, it had a soft, ready-to-melt texture which has never been obtained in the past.

Comparative Example (10-4)

The chiffon cake prepared by omitting native gellan gum from the recipe but otherwise in the same manner as Example (10-2) showed the oven shrinkage defect, i.e. shrinkage in height direction and deformation, with the loss of fluffy feel and melting quality in the mouth, so that it had no marketability as a chiffon cake.

Example (10-3)

The frozen white of eggs thawed at room temperature, 8 kg, was weighed into the bowl of a stirring mixer. Using the whipper, this egg white was beaten at 216 rpm and 8 kg of dry egg white powder was added under beating for 4 minutes. Separately, a mixture of 0.05 kg of native gellan gum, 0.2 kg of ι-carrageenan, 2 kg of soybean diet fiber, and 50 kg of refined sucrose was added to 57 kg of water and heated at 80° C. for 10 minutes. This mixture was added into the bowl at a temperature not below 75° C. to provide a meringue. One-third of the amount of this meringue was added to a mixture of 68 kg of egg yolk, 38 kg of liquid oil and 100 kg of refined sucrose, and the whole mixture was stirred well. Then, a mixture of 60 kg of wheat flour and 1 kg of baking powder was added evenly and the remainder of the meringue was Further added and gently admixed to prepare a chiffon cake batter. This batter, 140 g, was filled into a chiffon cake No. 14 mould and baked at 180° C. for 20 minutes, whereby a chiffon cake without oven shrinkage and possessing a delicate ready-to-melt texture was obtained.

Comparative Example (10-5)

The chiffon cake prepared by omitting native gellan gum but using otherwise the same recipe and same procedure as in Example (10-3) showed an oven shrinkage of 20% and its solid texture gave a poor mouth-feel.

Example 11

Palatability/Body Improving Agent-(1)

Example (11-1)

Milk Pudding

| | |
|---|---|
| Sugar | 10.0 wt. % |
| Skim milk powder | 6.5 |
| Coconut oil | 4.0 |
| Glycerin fatty acid ester | 0.1 |
| Carotene base | 0.1 |
| Pudding flavor | 0.1 |
| Carrageenan | 0.15 |
| Locust bean gum | 0.25 |
| Water | Balance |
| Total | 100 wt. % |

A basal pudding composition was prepared according to the above recipe and 0.05 wt. % of native gellan gum (Saneigen F. F. I.) was added. This mixture was stirred to provide a food composition. This food composition was pasteurized at 125° C. for 4 seconds, filled into a pudding cup, and allowed to cool at room temperature to provide a pudding.

Comparative Examples (11-1) ~(11-4)

Control puddings were prepared by omitting native gellan gum from the recipe used in Example (11-1) [Comparative Example (11-1)], a recipe including 0.05 wt. % of xanthan gum in lieu of native gellan gum [Comparative Example (11-2)], a recipe including 1 wt. % of starch in lieu of native gellan gum [Comparative example (11-3)], and a recipe including 0.1% of sodium metaphosphate in lieu of native gellan gum [Comparative Example (11-4)], respectively, in otherwise the same manner as in Example (11-1). The formulating amounts of those gums were their optimum amounts for addition to puddings.

The following experiment examples are intended to illustrate the invention relevant to embodiment (11) (a) in further detail.

Experiment Example 11

The pudding prepared in Example (11-1) and the puddings prepared in Comparative Examples (11-1) ~(11-4) were compared in regard to stabilizing effect and palatability. The results are shown in Table 10.

TABLE 10

| | Appearance | Palatability |
|---|---|---|
| Example (11-1) Native gellan gum 0.05% | No "roughening" was found at all. Marked improvement in syneresis. | A slick mouth-feel, ready-to-melt in the mouth; delicious. |
| Comparative Example (11-1) Not added | Marked "roughening" made the pudding hardly acceptable for marketing. Syneresis was also noted. | A grainy mouth-feel and a heterogeneous taste. |
| Comparative Example (11-2) Xanthan gum 0.05% | Compared with non-addition control, "roughening" was somewhat inhibited but the effect was insufficient. A high rate of syneresis was noted. | An elastic rubber-like mouth-feel, far removed from the mouth-feel of puddings. Poor meltability in the mouth. |
| Comparative Example (11-3) Starch 1.0% | Marked "roughening" made the pudding hardly acceptable for marketing. Syneresis was also noted. | A soft paste-like mouth-feel as well as a grainy texture; a heterogeneous taste. |
| Comparative Example (11-4) Sodium metaphosphate 0.1% | Marked "roughening" made the pudding hardly acceptable for marketing. Syneresis was also found. | A grainy texture; a heterogeneous taste. |

It is clear from Table 10 that native gellan gum is not only effective in preventing "roughness" but also useful for suppressing syneresis.

As Example (11-2), a pudding composition containing native gellan gum as prepared according to the same recipe as that used in Example (11-1) was pasteurized at 125° C. for 4 seconds, filled into a pudding cup, and quenched to provide a pudding. In this case, too, no "roughening" occurred and the pudding had a glossy appearance and a delicate texture which almost melted itself easily in the mouth.

Example (11-3)

Calcium-enriched Pudding

| | |
|---|---|
| Milk | 10 wt. % |
| Skim milk powder | 3 |
| Sweetened condensed whole milk | 4 |
| Sugar | 10 |
| Purified coconut oil | 4.5 |
| Egg yolk with 20% sugar | 1.2 |
| Carrageenan | 0.3 |
| Locust bean gum | 0.15 |
| Xanthan gum | 0.05 |
| Calcium carbonate | 0.43 |
| Glycerin fatty acid ester | 0.1 |

-continued

| | |
|---|---|
| Pudding flavor | 0.1 |
| Carotene base | 0.1 |
| Native gellan gum | 0.02 |
| Water | Balance |
| Total | 100 wt. % |

A food processing composition for calcium-enriched puddings was prepared according to the above recipe. This composition was pasteurized at 125° C. for 4 seconds, filled into a pudding cup, and allowed to cool at room temperature to provide a calcium-enriched pudding.

Example (11-4)

Black Tea Pudding

| | |
|---|---|
| Milk | 35 wt. % |
| Sugar | 10 |
| Skim milk powder | 5 |
| Carrageenan | 0.2 |
| Locust bean gum | 0.2 |
| Agar | 0.1 |
| Trisodium citrate | 0.1 |
| Glycerin fatty acid ester | 0.1 |
| Black tea extract | 6.0 |
| Black tea flavor | 0.1 |
| Milk flavor | 0.03 |
| Native gellan gum | 0.05 |
| Water | Balance |
| Total | 100 wt. % |

A food processing composition for black tea puddings was prepared according to the above recipe. This composition was pasteurized at 125° C. for 4 seconds, filled into a pudding cup, and cooled with wlalter at room temperature to provide a black tea pudding.

Example (11-5)

Green Tea Pudding

| | |
|---|---|
| Milk | 25 wt. % |
| Skim milk powder | 5 |
| Raw cream | 10 |
| Sweetened egg yolk | 4 |
| Sugar | 7 |
| Powdered starch syrup | 3 |
| Carrageenan | 0.25 |
| Locust bean gum | 0.2 |
| Xanthan gum | 0.2 |
| Milled green tea | 1 |
| Color | 0.1 |
| Green tea flavor | 0.15 |
| Milk cream base | 0.2 |
| Brandy | 1 |
| Native gellan gum | 0.02 |
| Water | Balance |
| Total | 100 wt. % |

A food processing composition for milled green tea puddings was prepared according to the above recipe. This composition was pasteurized at 125° C. for 4 seconds, filled into a pudding cup and allowed to cool at room temperature to provide a milled green tea pudding.

Example (11-6)

Coffee-milk Pudding

| | |
|---|---|
| Sweetened condensed whole milk | 12 wt. % |
| Skim milk powder | 3 |
| Purified coconut oil | 3 |
| Sugar | 4 |
| Powdered starch syrup | 4 |
| Carrageenan | 0.2 |
| Locust bean gum | 0.4 |
| Glycerin fatty acid ester | 0.2 |
| Coffee extract | 3 |
| Natural coffee essence | 0.1 |
| Milk cream base | 0.2 |
| Raw cream flavor | 0.05 |
| Brandy | 1 |
| Native gellan gum | 0.02 |
| Water | Balance |
| Total | 100 wt. % |

A food processing composition for coffee-milk puddings was prepared according to the above recipe. This composition was pasteurized at 125° C. for 4 seconds, filled into a pudding cup and allowed to cool at room temperature to provide a coffee-milk pudding.

Example (11-7)

Retort Chocolate Pudding

| | |
|---|---|
| Sweetened condensed whole milk | 10 wt. % |
| Skim milk powder | 6 |
| Purified coconut oil | 4 |
| Sugar | 5 |
| Sweetened whole egg | 2 |
| Cacao powder | 1 |
| Carrageenan | 0.15 |
| Locust bean gum | 0.15 |
| Guar gum | 0.05 |
| Trisodium citrate | 0.05 |
| Glycerin fatty acid ester | 0.2 |
| Black chocolate flavor | 0.15 |
| Native gellan gum | 0.3 |
| Water | Balance |
| Total | 100 wt. % |

A food processing composition for retort chocolate puddings was prepared according to the above recipe. This composition was filled into a retort pouch, pasteurized at 120° C. for 20 minutes, and cooled with water to provide a retort chocolate pudding.

Example (11-8)

Frozen Pudding

| | |
|---|---|
| Milk | 40 wt. % |
| Sweetened condensed whole milk | 10 |
| Raw cream | 5 |
| Sweetened yolk egg | 4 |
| Sugar | 5 |
| Powdered starch syrup | 5 |
| Carrageenan | 0.15 |
| Locust bean gum | 0.1 |

-continued

| | |
|---|---|
| Xanthan gum | 0.1 |
| Glycerin fatty acid ester | 0.1 |
| Carotene base | 0.1 |
| Milk cream base | 0.2 |
| Pudding essence | 0.15 |
| Native gellan gum | 0.05 |
| Water | Balance |
| Total | 100 wt. % |

A food processing composition for frozen puddings was prepared according to the above recipe. This composition was pasteurized at 125° C. for 4 seconds, filled into a pudding cup, cooled with water, and frozen at −20° C. to provide a frozen pudding.

Example (11-9)

Chocolate Mousse

| | |
|---|---|
| Sugar | 7 wt. % |
| Skim milk powder | 3 |
| Milk | 30 |
| Raw cream | 20 |
| Cacao powder | 1 |
| Corn starch | 1 |
| Carrageenan | 0.5 |
| Glycerin fatty acid ester | 0.1 |
| Flavor | 0.15 |
| Brandy | 1 |
| Native gellan gum | 0.1 |
| Water | Balance |
| Total | 100 wt. % |

A food processing composition for chocolate mousse was prepared according to the above recipe. This composition was filled into a retort pouch, pasteurized at 120° C. for 20 minutes, and cooled with water at 10° C. to provide a chocolate mousse.

Example (11-10)

Annin-tofu Dessert

| | |
|---|---|
| Sugar | 5 wt. % |
| Milk | 10 |
| Carrageenan | 0.2 |
| Locust bean gum | 0.3 |
| Xanthan gum | 0.3 |
| trisodium citrate | 0.1 |
| Potassium chloride | 0.05 |
| Flavor | 0.15 |
| Native gellan gum | 0.02 |
| Water | Balance |
| Total | 100 wt. % |

A food processing composition for annin-tofu desserts was prepared according to the above recipe. This composition was heated at 90° C. for 10 minutes, poured into a mould, and allowed to cool and solidify at room temperature to provide dice of annin-tofu measuring 13 mm cube. Then, the annin-tofu dice, mandarin orange cuttings and pineapple cuttings, both of suitable size, were placed in a dessert cup. After the filling of a syrup, the product was pasteurized at 85° C. for 30 minutes and cooled with water to provide an annin-tofu dessert.

Example (11-11)

Columnar Tricolor Pudding

| <Black tea pudding component> | |
|---|---|
| Sugar | 10 wt. % |
| Milk | 30 |
| Skim milk powder | 5 |
| Carrageenan | 0.2 |
| Locust bean gum | 0.1 |
| Glycerin fatty acid ester | 0.1 |
| Black tea extract | 6 |
| Flavor | 0.1 |
| Native gellan gum | 0.1 |
| Water | Balance |
| Total | 100 wt. % |
| <Milk pudding component> | |
| Sugar | 10 wt. % |
| Milk | 30 |
| Skim milk powder | 5 |
| Butter | 3 |
| Carrageenan | 0.1 |
| Locust bean gum | 0.2 |
| Glycerin fatty acid ester | 0.1 |
| Flavor | 0.1 |
| Native gellan gum | 0.1 |
| Water | Balance |
| Total | 100 wt. % |
| <Coffee pudding component> | |
| Sugar | 10 wt. % |
| Milk | 30 |
| Skim milk powder | 5 |
| Carrageenan | 0.1 |
| Locust bean gum | 0.1 |
| Gellan gum | 0.05 |
| Glycerin fatty acid ester | 0.1 |
| Coffee extract | 5 |
| Flavor | 0.1 |
| Native gellan gum | 0.1 |
| Water | Balance |
| Total | 100 wt. % |

According to the above recipes, black tea, milk, and coffee pudding components were respectively prepared by the routine procedure, pasteurized at 125° C. for 4 seconds and allowed to cool at room temperature When the temperature had fallen to 65° C., the respective components were concurrently dispensed, in equal amounts, into a pudding cup to provide a tricolor pudding consisting of 3 columns of different colors.

Although this tricolor pudding contained black tea and coffee extracts, neither roughening nor syneresis was observed in the respective components as well as across the interfaces. This pudding showed well-defined intercolumn borders, too. Moreover, the respective pudding components retained their characteristic flavors and were invariably delicious.

It is apparent from the above examples that despite its procedural simplicity, this invention provides a high-quality tricolor pudding having well-defined interfaces and free from roughness and cohesion defects.

Example 12

Palatability/Body-improving Agent-(2)

Example (12-1)

Fried Batter Sheet

To 1 weight % of tenkasu (fried batter fragments) (the diameter of individual fragments: 3~10 mm) was added 1 weight % of a cold water-swollen preparation containing 0.2 wt. % native gellan gum which was separately prepared in advance. This mixture was gently stirred, filled into a mould, and immediately immersed in oil at 160° C. for 90 seconds to provide a fried batter sheet.

Example (12-2)

Uncoated Fry of Shrimps

To 1 wt. % of shrimps (about 3 cm from head to anus) was added 1 wt. % of a cold water-swollen preparation containing 0.2 wt. % native gellan gum, and 0.2 wt. % xanthan gum which was separately prepared in advance. The mixture was gently stirred, filled into a mould, and dipped in oil at 160% for 90 seconds to provide a shrimp uncoated fry sheet.

Example (12-3)

Uncoated Fry of Shrimps

To 1 wt. % of shrimps (about 3 cm from head to anus) was added 1 wt. % of a cold water-swollen preparation containing 0.002 wt. % of native gellan gum, followed by mixing. This mixture was placed in a mould and dipped in oil at 160° C. for 90 seconds to provide a shrimp uncoated fry sheet.

Example (12-4)

Mixed Fry

To 1 wt. % of a mixture of onion, potato and carrot strips was added 1 wt. % of a cold water-swollen preparation containing 0.2 wt. % native gellan gum which was separately prepared in advance, and after light blending, the mixture was placed in a mould and dipped in oil at 160° C. for 90 seconds to provide kakiage (a mixed fry).

Example (12-5)

Hamburg Steak

To 1 wt. % of a well-roasted mixture of minced meat and onion cuttings as prepared using a frypan was added 1 wt. % of a cold water-swollen preparation containing 0.2 wt. % native gellan gum and 0.2 wt. % xanthan gum as separately prepared in advance. After light blending, the mixture was placed in a mould and dipped in oil at 160° C. for 90 seconds to provide a hamburg steak.

Example (12-6)

Tsumire (Dumpling) (Fish Ball)

To 1 wt. % of a well-roasted mixture of minced fish meat, leeks and other vegetables was added 1 wt. % of a cold water-swollen preparation containing 0.2 wt. % native gellan gum as separately prepared in advance. After light blending, the mixture was placed in a mould and dipped in oil at 160° C. for 90 seconds to provide a tsumire dumpling (fish ball).

Example (12-7)

Croquette

An ingredient mixture of 200 wt. % of steamed and mashed potato, 15 wt. % of roasted minced meat, 20 wt. % of onion, 10 wt. % of carrot, 15 wt. % of corn, 3 wt. % of salt, 6 wt. % of sugar, 5 wt. % of margarine and 2 wt. % of seasoning was prepared. To 1 weight % of the above mixture was added 1 wt. % of a cold water-swollen preparation containing 0.2 wt. % native gellan gum as separately prepared in advance. After blending, the whole mixture was molded. The surface of the molding was serially coated with wheat flour and whisked egg in the order mentioned, further covered with bread crumbs, and fried in oil at 160° C. to provide a croquette.

Example (12-8)

Croquette

To a mixture of 289.3 wt. % of wheat flour, 29 wt. % of sugar, 5.6 wt. % of salt, and 0.7 wt. % of native gellan gum was added 172 wt. % of water, and using 4 wt. % of baker's yeast, bread crumbs were prepared in accordance with the conventional sequence of fermentation, baking, crushing and drying.

An ingredient mixture of 200 wt. % of-steamed and mashed potato, 15 weight % of roasted minced meat, 20 wt. % of onion, 10 wt. % of carrot, 15 wt. % of corn, 3 wt. % of salt, 6 wt. % of sugar, 5 wt. % of margarine and 2 wt. % of other seasonings was prepared. To 1 wt. % of this ingredient mixture was added 1 wt. % of a cold water-swollen preparation containing 0.2 wt. % native gellan gum which was separately prepared in advance. After blending, the mixture was molded and the molding was serially coated with wheat flour and whisked egg, further covered with the bread crumbs prepared above and fried in oil at 160° C. to provide a croquette.

Comparative Example (12-1)

Tenkasu (fried batter) sheets were prepared by using
(1) 1 wt. % of a cold water-swollen preparation containing 0.3 wt. % gellan gum,
(2) 1 wt. % of a cold water-swollen preparation containing 0.3 wt. % of xanthan gum, or
(3) 1 wt. % of a cold water-swollen preparation containing 1 wt. % pullulan in lieu of 1 wt. % of a cold water-swollen preparation containing 0.2 wt. % native gellan gum in otherwise the same manner as in Example (12-1).

As a result, whereas the fried batter sheet obtained in Example (12-1) had a good bulk and a corrugated surface texture which was appetizing, the fried batter sheets (1) and (2) were flat sheets with a poor appearance. In the case of (3), the composition could not be molded into a sheet but rather consisted of discrete fragments of the fried batter and was unsuited for ingestion.

The palatability of these sheets was also evaluated. The fried batter sheet according to Example (12-1) was crispy, not oily, and savory, retaining the initial palatability even at 5 hours after frying. In contrast, the sheets (1) and (2) were less crispy and somewhat oily and particularly this oily mouth-feel became more and more prominent as time passed by after frying.

Then, those fried batter sheets were preserved at −20° C. overnight and, then, thawed at 4° C. and ingested. As a result, whereas the fried batter sheet of Example (12-1) was still crispy and savory, both sheets (1) and (2) were wet with water and oil and unsavory.

Example 13

Palatability/Body-improving Agent-(3)

Example (13-1)

Shaved Ice with Syrup

To 50 wt. % of water was added 26 wt. % of high fructose corn syrup, and the mixture was stirred. To this mixture were added 0.03 wt. % of native gellan gum, 20 wt. 5% of sugar, 0.05 wt. % of carrageenan, 0.1 wt. % of locust bean gum and 0.2 wt. % of starch, and the whole mixture was stirred for dissolving at 80° C. for 10 minutes. This solution was cooled to 20° C. and 0.2 wt. % of citric acid (crystals), 0.3 wt. % of color and 0.2 wt. % of flavor were added. The mixture was stirred, adjusted with water to 100 wt. %, and cooled to 5° C. to provide a syrup for shaved ice.

Separately, "ice flakes" prepared by shaving ice thin in the routine manner were placed in a vessel, and based on 3 wt. % of the ice flakes, 2 wt. % of the above syrup for shaved ice was added and the mixture was quickly frozen to provide a shaved ice with syrup. As demonstrated below in Experiment Example (13-1), the shaved ice thus obtained could be easily spooned.

Comparative Example (13-1)

Except that 0.03 wt. % of native gellan gum was omitted, the procedure of Example (13-1) was otherwise repeated to prepare a shaved ice with syrup (conventional product). The shaved ice thus prepared is one of the products which are currently known to be the most easy to pierce through with a spoon, indicating the limit of the state of the art.

Experiment Example (13-1)

Confirmation of the Ease of Spooning

A cylindrical vessel 40 mm in diameter was filled with the syrup-containing shaved ice of Example (13-1) (invention product) or the conventional product up to 40 mm in height. Using Instron (a universal material tester, Instron), the crush strength of shaved ice was measured with a blade 20 mm wide and 1.2 mm thick at a speed of 60 mm/minute.

Figure 47:
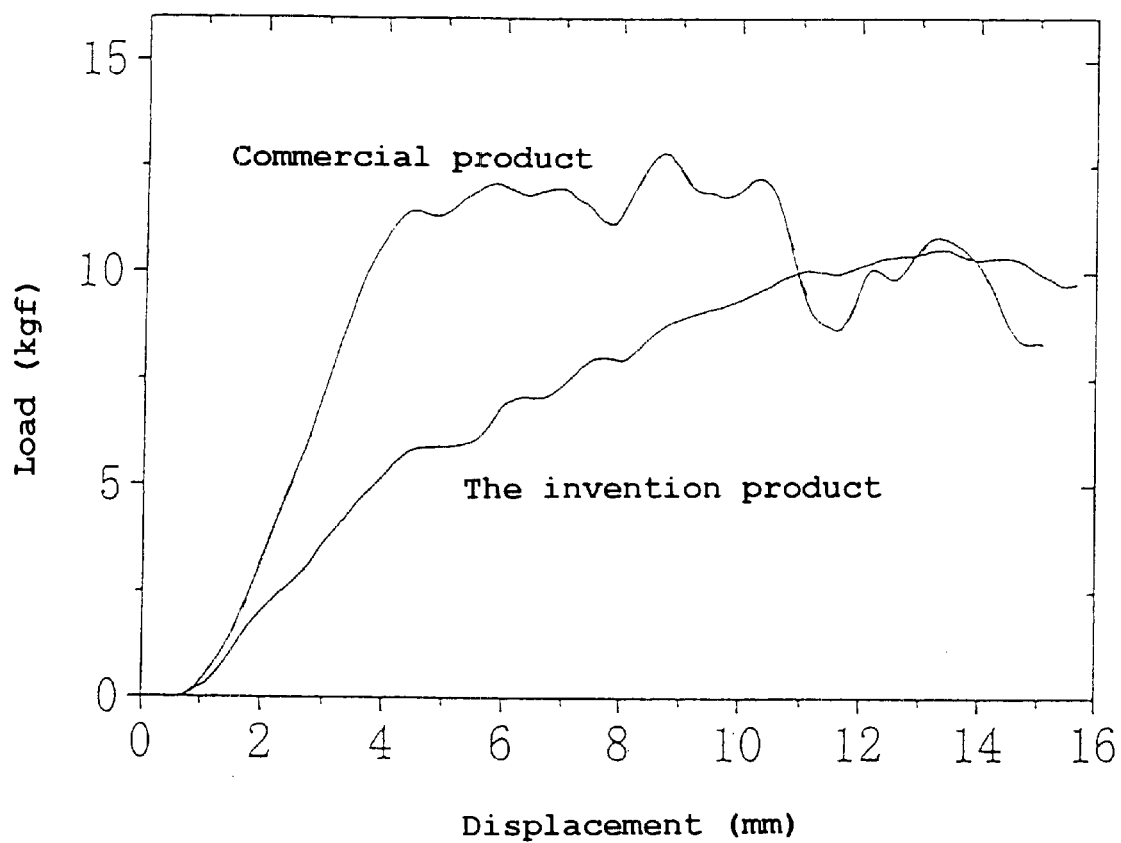
FIG. 47 is a diagram showing the results of measurement (Instron, a universal material measuring apparatus) and comparison of the ice crush strength of the sherbet (ice flakes) obtained in Experiment Example (13-1) and the conventional sherbet not containing native gellan gum.

The results are shown in FIG. 47. Thus, the shaved ice of the invention began to disintegrate under a smaller load than the most spoonable commercial product and gave a substantially linear relation between the load and the degree of crush (displacement), thus endorsing the result of the organoleptic evaluation that the spoonability of the product of this invention is extremely high.

Experiment Example (13-2)

Of the shaved ice product obtained in Example (13-1), the top layer down to ½ of vessel capacity was removed as if the ice had been half consumed. The remainder of the ice was allowed to melt gradually at room temperature and the resulting liquid was examined. The shaved ice prepared in Comparative Example (13-1) was similarly monitored in the same manner.

As a result, the shaved ice according to Example (13-1) showed no difference in taste or appearance between the top layer and the bottom layer, with all the liquid being uniform in composition from the beginning of melting to the end. In contrast, the shaved ice according to Comparative Example (13-1) gave the impression that frozen pure water had been segregated from the remainder of the system and, moreover, was uneven throughout, with the liquid from the bottom layer being more intense in taste and appearance, particularly in color.

Example 14

Palatability/Body Improving Agent-(4) Crispy Hard Candy

To 20 wt. % of water was added 0.05 wt. % of native gellan gum, and 60 wt. % of granulated sugar and 40 wt. % of starch syrup were added under heating. The mixture was boiled down at an ultimate temperature of 150° C., followed by cooling to 130° C. Then, 0.6 wt. % of tartaric acid, 2 wt. % of concentrated (⅕) grape juice, 0.2 wt. % of flavor and 0.02 wt. % of color were added. After blending, the mixture was then molded with a candy-making machine to provide a crispy hard candy.

Example 15

Palatability/Body-improving Agent-(5)

Example (15-1)

Noodle with Increased Body

A universal mixer was charged with a mixture of 0.2 wt. % of native gellan gum and 300 wt. % of soft flour. Then, a solution of 12 wt. % of salt in 115 wt. % of water was added, and the whole mixture was stirred for 10 minutes. Using a noodle-making machine, the mixture was subjected to one pre-compounding cycle, 2 compounding cycles, and 3 rolling cycles to provide a noodle 2.5 mm in thickness.

Example (15-2)

Dehydrated Noodle with Increased Body

The noodle obtained in Example (15-1) was dried at 95° C. for 1 hour to provide a dehydrated noodle. This dehydrated noodle reconstitutes itself in boiling water in a short time and the reconstituted noodle had a strong body.

INDUSTRIAL APPLICABILITY

The present invention provides novel uses of native gellan gum. Those uses encompass a broad range inclusive of food and other industrial products.

The freeze-thaw resistant jelly according to the invention, if frozen and thawed, retains its elasticity and shape-retaining properties substantially without separation of water after thawing. However, it has a well-acceptable palatability and the property to recover the pre-freezing mouth-feel on thawing. Therefore, in accordance with this invention, there can be provided a jelly having a long shelf-life necessary for shipment and distribution in frozen condition and providing a multi-faceted palatability.

The dehydrated gel according to the invention is compact and easy to carry about and withstands long-term storage regardless of storage conditions. Moreover, this product regains the initial characteristic (elasticity) and form of a hydrogel upon addition of water, thus enabling ingestion. Therefore, in accordance with this invention, there can be provided a dehydrated gel, particularly an edible dehydrated gel, which is of convenience in storage and distribution.

The rice cake-like gel according to the invention is a gel having lasting rice cake-like viscoelasticity and heat resistance. More particularly, this product has been inhibited against aging in quality to persistently exhibit a sustained rice cake-like viscoelasticity and is so resistant to heat that it does not easily dissolve out or become macerated in a heat treatment in water or in an hydrous environment, such as pasteurization or retort treatment. Therefore, in accordance with this invention, there can be provided a substitute rice cake which is resistant to heat and aging and a retort food containing such a substitute rice cake.

The copy food according to this invention is a non-calorie, non-cholesterol food endowed with a broadly variable palatability by using native gellan gum. As a result, the invention provides a variety of foods which enable a variegated dietary life. Furthermore, the artificial bait provided by this invention contributes to protection of the earth's ecology.

The method of this invention for the production of native gellan gum-containing gel compositions makes it possible to prepare compositions containing high levels of native gellan gum which has heretofore been almost impossible to achieve. This method is useful in that it enables production of gel compositions of high viscosity and body, thus enlarging the scope of usefulness of gel compositions.

The cold retention composition and cooling agent according to this invention not only have cold retention and cold storage properties but are adhesive by themselves so that they can be handled and used with convenience. Moreover, they have an adequate degree of moisture permeability. This invention has a great application potential in that the product can be safely and expediently applied to the human body without risks for adverse effects and, even when directly applied in a sheet form to the human skin or like substrate, can be removed without residues on the substrate surface.

The present invention further provides the use of native gellan gum as an additive.

In the first embodiment of said additive, the invention provides the use of native gellan gum as a dispersion stabilizer and the application thereof. The dispersion stabilizer comprising native gellan gum either alone or in combination with microcrystalline cellulose or pectin is not only capable of maintaining a homogeneous distribution of solids in a liquid system but also capable of inhibiting phase separation of a liquid composition comprising non-compatible or immiscible liquid components to thereby insure a sustainedly dispersed or homogeneous coexistence of immiscible liquids. Particularly a dispersion stabilizer comprising native gellan gum and pectin is capable of imparting high dispersibility even in the presence of comparatively high levels of salt. In accordance with this invention, there can be provided food and industrial products reflecting improved dispersibility and improved homogeneity of ingredients or components.

In the second embodiment of said additive, the invention provides the use of native gellan gum as an additive for thickened compositions, the application thereof, and a thickening method which can be expediently reduced to practice. In the presence of a polysaccharide such as tamarind seed gum or the like, native gellan gum in the form of a low-concentration, low-viscosity solution in a small volume is capable of thickening a substrate composition to a high degree of viscosity without inducing gelation. Therefore, the thickened composition additive of the invention is useful as a thickening agent which does not affect the composition of a substrate, which includes a variety of food and other items, and which is easy to handle and capable of thickening the substrate with convenience in industrial production.

In the third embodiment of said additive, the invention provides the use of native gellan gum as a heat resistance-imparting agent, particularly a retort resistance-imparting agent, and the application thereof. The retort resistance-imparting agent comprising native gellan gum according to this invention can be used for the purpose of imparting retort resistance to bean curds and other foods. Therefore, the foods prepared in accordance with this invention withstand long-term storage and/or room temperature storage without being altered in palatability, properties and form even by retort treatment. Therefore, this invention is of value as a method for prolonging the shelf-lives of foods.

In the fourth embodiment of said additive, the invention provides the use of native gellan gum as a syneresis inhibitor and the application thereof. The syneresis inhibitor comprising native gellan gum in accordance with this invention is capable of causing the liquid component of a gel composition to be securely entrapped within the composition without interfering with the inherent elasticity, strength, taste and flavor of the gel composition. Therefore, in accordance with this invention, there can be provided foods the quality of which is long-sustained owing to significant suppression of syneresis, for example during storage.

In the fifth embodiment of said additive, the invention provides the use of native gellan gum as a foam stabilizer and the application thereof. The foam stabilizer comprising native gellan gum in accordance with this invention stabilizes foams derived from protein, particularly from eggs, to maintain their cellular structures. Therefore, in the production of foods using a meringue, the invention enables preparation of a meringue which can be left standing until used. Furthermore, in accordance with this invention, by exploiting the high stability of meringues, cakes having delicate and soft mouth-feels can be produced without the risk for oven shrinkage even when the production process involves use of compositions of low solid content.

In the sixth embodiment of said additive, the invention provides the use of native gellan gum as a palatability/body-improving agent and the application thereof. The palatability/body-improving agent of the invention has a multi-pronged functionality dependent on the kind of food to which it is applied so that, for example, it can be used for preventing the in-process "roughening" trouble in the production of foods containing milk components and gelling agents to thereby insure slick and delicate mouth-feels, adding bulk to fried foods and, through improved oil drainage, imparting a crisp biting quality to such foods, providing ice cakes with improved spoonability and crisp palatability, providing hard candies with adequate biting resistance and a crispy consistency not requiring undue exertions in ingestion, and providing noodles with strong body and ease of reconstitution with water.

Thus, in accordance with the present invention, there can be provided foods with improved palatability and/or body and improved quality.

What is claimed is:

1. A dehydrated gel composition which is produced by dehydrating a hydrated gel composition comprising an isolated acetylated gellan gum.

2. The dehydrated gel composition according to claim 1, wherein the hydrated gel composition comprises from 0.1 to 3% wt./wt. of the isolated acetylated gellan gum.

3. The dehydrated gel composition according to claim 1, wherein the hydrated gel composition further comprises at least one member selected from the group consisting of sugar, high-performance sweetener, fruit pulp, boiled adzuki bean and oily flavor.

4. The dehydrated gel composition according to claim 1, wherein the hydrated gel composition is produced by dispersing the isolated acetylated gellan gum in an aqueous medium, heating the dispersion for dissolving and cooling the dissolved solution.

5. A method of preparing a hydrated get composition containing an isolated acetylated gellan gum, comprising re-hydrating the dehydrated gel composition of claim 1.

6. The method of preparing a hydrated gel composition according to claim 5, wherein the hydrated gel composition is a jelly.

7. The method of preparing a hydrated gel composition according to claim 5, further comprising allowing the dehydrated gel composition to absorb water containing an alcohol, a sweetener, an acidulant or a flavor.

8. A dehydrated gel composition which is produced by dehydrating a hydrated gel composition comprising an isolated acetylated gellan gum, the dehydrated get composition being capable of reconstitution with water to reproduce the original elasticity and form of the hydrated get composition.

* * * * *